(12) United States Patent
Desai

(10) Patent No.: US 10,744,110 B2
(45) Date of Patent: Aug. 18, 2020

(54) METHODS OF TREATING LUNG CANCER

(71) Applicant: Abraxis BioScience, LLC, Summit, NJ (US)

(72) Inventor: Neil P. Desai, Pacific Palisades, CA (US)

(73) Assignee: Abraxis BioScience, LLC, Summit, NJ (US)

( * ) Notice: Subject to any disclaimer, the term of this patent is extended or adjusted under 35 U.S.C. 154(b) by 0 days.

(21) Appl. No.: 14/772,335

(22) PCT Filed: Mar. 10, 2014

(86) PCT No.: PCT/US2014/022341
§ 371 (c)(1),
(2) Date: Sep. 2, 2015

(87) PCT Pub. No.: WO2014/159171
PCT Pub. Date: Oct. 2, 2014

(65) Prior Publication Data
US 2016/0015681 A1    Jan. 21, 2016

Related U.S. Application Data

(60) Provisional application No. 61/778,299, filed on Mar. 12, 2013.

(51) Int. Cl.
| | | |
|---|---|---|
| *A61K 31/337* | (2006.01) | |
| *A61K 47/69* | (2017.01) | |
| *A61K 47/64* | (2017.01) | |
| *A61K 9/14* | (2006.01) | |
| *A61K 9/51* | (2006.01) | |
| *A61K 31/555* | (2006.01) | |
| *A61K 33/24* | (2019.01) | |
| *A61K 47/42* | (2017.01) | |

(52) U.S. Cl.
CPC .............. *A61K 31/337* (2013.01); *A61K 9/14* (2013.01); *A61K 9/5169* (2013.01); *A61K 31/555* (2013.01); *A61K 33/24* (2013.01); *A61K 47/42* (2013.01); *A61K 47/643* (2017.08); *A61K 47/6929* (2017.08)

(58) Field of Classification Search
CPC .............. A61K 2300/00; A61K 31/337; A61K 31/555; A61K 33/24; A61K 47/42; A61K 47/643; A61K 47/6929; A61K 9/14; A61K 9/5169
See application file for complete search history.

(56) References Cited

U.S. PATENT DOCUMENTS

| | | |
|---|---|---|
| 5,362,478 A | 11/1994 | Desai et al. |
| 5,439,686 A | 8/1995 | Desai et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,916,596 A | 6/1999 | Desai et al. |
| 5,997,904 A | 12/1999 | Magdassi et al. |
| 6,096,331 A * | 8/2000 | Desai ............... A23L 1/296 424/422 |
| 6,506,405 B1 | 1/2003 | Desai et al. |
| 6,528,067 B1 | 3/2003 | Magdassi et al. |
| 6,537,579 B1 | 3/2003 | Desai et al. |
| 6,565,842 B1 | 5/2003 | Desai et al. |
| 6,652,884 B2 | 11/2003 | Falciani |
| 6,749,868 B1 | 6/2004 | Desai et al. |
| 6,753,006 B1 | 6/2004 | Desai et al. |
| 7,758,891 B2 | 7/2010 | Desai et al. |
| 7,771,751 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |

(Continued)

FOREIGN PATENT DOCUMENTS

| | | |
|---|---|---|
| NZ | 576856 A | 6/2012 |
| NZ | 602385 A | 8/2014 |

(Continued)

OTHER PUBLICATIONS

Socinski et al., Safety and efficacy of weekly nab®-paclitaxel in combination with carboplatin as first-line therapy in elderly patients with advanced non-small-cell lung cancer. Annals. of Oncology 2013, 24:314-321.*
Reynolds et al., Phase II trial of nanoparticle albumin-bound paclitaxel, carboplatin, and bevacizumab in first-line patients with advanced nonsquamous non-small cell lung cancer. Journal of Thoracic Oncology 2009, 4(12):1537-1543.*
Abraxane for Injectable Suspension. Celgene Corporation. Sep. 2013, 5 pages.*
Calvert et al. Carboplatin Dosage: Prospective Evaluation of a Simple Formula Based on Renal Function. Journal of Clinical Oncology, 1989, 7(11):1748-1756.*
Hatlen et al. Prolonged Survival in Patients with Lung Cancer with Diabetes Mellitus. J Thorac Oncol. 2011, 6:1810-1817. (Year: 2011).*

(Continued)

*Primary Examiner* — Robert A Wax
*Assistant Examiner* — Olga V. Tcherkasskaya
(74) *Attorney, Agent, or Firm* — Morrison & Foerster LLP

(57) ABSTRACT

The present invention provides methods and compositions for treating non-small-cell lung cancer (NSCLC) by administering a) a composition comprising nanoparticles that comprise paclitaxel and an albumin and b) a platinum-based agent (e.g., carboplatin), wherein the individual has diabetes, has four or more metastatic sites, and/or is at least about 70 years old.

12 Claims, No Drawings

(56) References Cited

U.S. PATENT DOCUMENTS

| | | | |
|---|---|---|---|
| 8,138,229 B2 | 3/2012 | Desai et al. | |
| 8,143,236 B2* | 3/2012 | Hausheer | A61K 31/105 514/100 |
| 8,257,733 B2 | 9/2012 | Desai et al. | |
| 8,268,348 B2 | 9/2012 | Desai et al. | |
| 8,314,156 B2 | 11/2012 | Desai et al. | |
| 8,735,394 B2 | 5/2014 | Desai et al. | |
| 8,846,771 B2 | 9/2014 | Desai et al. | |
| 8,853,260 B2 | 10/2014 | Desai et al. | |
| 8,911,786 B2 | 12/2014 | Desai et al. | |
| 8,927,019 B2 | 1/2015 | Desai et al. | |
| 8,999,396 B2 | 4/2015 | Desai et al. | |
| 9,012,518 B2 | 4/2015 | Desai et al. | |
| 9,012,519 B2 | 4/2015 | Desai et al. | |
| 9,061,014 B2 | 6/2015 | Seward et al. | |
| 9,101,543 B2 | 8/2015 | Desai et al. | |
| 9,149,455 B2 | 10/2015 | Desai et al. | |
| 9,308,180 B2 | 4/2016 | De et al. | |
| 9,370,494 B2 | 6/2016 | Yeo et al. | |
| 9,393,318 B2 | 7/2016 | Desai et al. | |
| 9,399,071 B2 | 7/2016 | Desai et al. | |
| 9,399,072 B2 | 7/2016 | Desai et al. | |
| 9,446,003 B2 | 9/2016 | Desai et al. | |
| 9,511,046 B2 | 12/2016 | Desai et al. | |
| 9,561,288 B2 | 2/2017 | Desai et al. | |
| 9,585,960 B2 | 3/2017 | Foss et al. | |
| 9,597,409 B2 | 3/2017 | Desai et al. | |
| 9,675,578 B2 | 6/2017 | Desai et al. | |
| 9,724,323 B2 | 8/2017 | Desai et al. | |
| 9,820,949 B2 | 11/2017 | Desai et al. | |
| 9,855,220 B2 | 1/2018 | Desai et al. | |
| 9,884,013 B2 | 2/2018 | Seward et al. | |
| 9,962,373 B2 | 5/2018 | Desai et al. | |
| 10,076,501 B2 | 9/2018 | Foss et al. | |
| 2003/0185894 A1 | 10/2003 | Zenoni et al. | |
| 2003/0187062 A1 | 10/2003 | Zenoni et al. | |
| 2003/0199425 A1 | 10/2003 | Desai et al. | |
| 2005/0004002 A1 | 1/2005 | Desai et al. | |
| 2006/0263434 A1 | 11/2006 | Desai et al. | |
| 2007/0082838 A1 | 4/2007 | De et al. | |
| 2008/0193498 A1* | 8/2008 | Hausheer | A61K 31/105 424/422 |
| 2008/0280987 A1 | 11/2008 | Desai et al. | |
| 2009/0263483 A1 | 10/2009 | Desai et al. | |
| 2010/0048499 A1 | 2/2010 | Desai et al. | |
| 2010/0166869 A1 | 7/2010 | Desai et al. | |
| 2010/0297243 A1 | 11/2010 | Desai et al. | |
| 2011/0052708 A1 | 3/2011 | Soon-Shiong et al. | |
| 2011/0118342 A1 | 5/2011 | De et al. | |
| 2011/0151012 A1 | 6/2011 | Desai et al. | |
| 2012/0070502 A1 | 3/2012 | Desai et al. | |
| 2012/0076862 A1 | 3/2012 | Desai et al. | |
| 2012/0128732 A1 | 5/2012 | Trieu et al. | |
| 2012/0189701 A1 | 7/2012 | Desai et al. | |
| 2012/0231082 A1 | 9/2012 | Desai et al. | |
| 2012/0283205 A1 | 11/2012 | Desai et al. | |
| 2012/0308612 A1 | 12/2012 | De et al. | |
| 2013/0045240 A1 | 2/2013 | Tao et al. | |
| 2013/0071438 A1 | 3/2013 | Desai et al. | |
| 2013/0115296 A1 | 5/2013 | Yeo et al. | |
| 2013/0195922 A1 | 8/2013 | Desai et al. | |
| 2013/0195983 A1 | 8/2013 | Desai et al. | |
| 2013/0195984 A1 | 8/2013 | Desai et al. | |
| 2013/0202709 A1 | 8/2013 | Desai et al. | |
| 2013/0209518 A1 | 8/2013 | Desai et al. | |
| 2013/0244952 A1 | 9/2013 | Desai et al. | |
| 2013/0266659 A1 | 10/2013 | Desai et al. | |
| 2013/0280336 A1 | 10/2013 | Desai et al. | |
| 2013/0280337 A1 | 10/2013 | Desai et al. | |
| 2014/0017315 A1 | 1/2014 | Desai et al. | |
| 2014/0017316 A1 | 1/2014 | Desai et al. | |
| 2014/0017323 A1 | 1/2014 | Desai et al. | |
| 2014/0023717 A1 | 1/2014 | Desai et al. | |
| 2014/0039069 A1 | 2/2014 | Desai et al. | |
| 2014/0039070 A1 | 2/2014 | Desai et al. | |
| 2014/0056986 A1 | 2/2014 | Desai et al. | |
| 2014/0072630 A1 | 3/2014 | Tao et al. | |
| 2014/0072631 A1 | 3/2014 | Trieu et al. | |
| 2014/0072643 A1 | 3/2014 | Desai et al. | |
| 2014/0079787 A1 | 3/2014 | Yeo et al. | |
| 2014/0079788 A1 | 3/2014 | Desai et al. | |
| 2014/0079793 A1 | 3/2014 | Desai et al. | |
| 2014/0080901 A1 | 3/2014 | Desai et al. | |
| 2014/0134257 A1 | 5/2014 | Desai et al. | |
| 2014/0155344 A1 | 6/2014 | Desai et al. | |
| 2014/0170228 A1 | 6/2014 | Desai et al. | |
| 2014/0186447 A1 | 7/2014 | Desai | |
| 2014/0199403 A1 | 7/2014 | Desai et al. | |
| 2014/0199404 A1 | 7/2014 | Heise et al. | |
| 2014/0199405 A1 | 7/2014 | Pierce et al. | |
| 2014/0271871 A1 | 9/2014 | Desai et al. | |
| 2014/0296279 A1 | 10/2014 | Seward et al. | |
| 2014/0296353 A1 | 10/2014 | Desai et al. | |
| 2014/0302157 A1 | 10/2014 | Desai et al. | |
| 2015/0050356 A1 | 2/2015 | Desai et al. | |
| 2015/0079177 A1 | 3/2015 | Desai et al. | |
| 2015/0079181 A1 | 3/2015 | Desai et al. | |
| 2015/0104521 A1 | 4/2015 | Desai et al. | |
| 2015/0111960 A1 | 4/2015 | Desai et al. | |
| 2015/0157722 A1 | 6/2015 | Foss et al. | |
| 2015/0165047 A1 | 6/2015 | Desai et al. | |
| 2015/0190519 A1 | 7/2015 | Desai et al. | |
| 2015/0313866 A1 | 11/2015 | Desai et al. | |
| 2016/0008330 A1 | 1/2016 | Desai et al. | |
| 2016/0015817 A1 | 1/2016 | Benettaib et al. | |
| 2016/0151325 A1 | 6/2016 | Desai et al. | |
| 2016/0228401 A1 | 8/2016 | Desai et al. | |
| 2016/0374952 A1 | 12/2016 | Yeo et al. | |
| 2017/0007569 A1 | 1/2017 | De et al. | |
| 2017/0014373 A1 | 1/2017 | Desai et al. | |
| 2017/0020824 A1 | 1/2017 | Desai et al. | |
| 2017/0049711 A1 | 2/2017 | Desai et al. | |
| 2017/0100344 A1 | 4/2017 | Desai et al. | |
| 2017/0105951 A1 | 4/2017 | Desai et al. | |
| 2017/0157035 A1 | 6/2017 | Seward et al. | |
| 2017/0172975 A1 | 6/2017 | Desai et al. | |
| 2017/0181988 A1 | 6/2017 | Desai et al. | |
| 2017/0202782 A1 | 7/2017 | Pierce et al. | |
| 2017/0224627 A1 | 8/2017 | Foss et al. | |
| 2017/0333384 A1 | 11/2017 | Desai et al. | |
| 2017/0340599 A1 | 11/2017 | Desai et al. | |
| 2018/0015181 A1 | 1/2018 | Desai et al. | |
| 2018/0064679 A1 | 3/2018 | Pierce et al. | |
| 2018/0133157 A1 | 5/2018 | Desai et al. | |
| 2018/0147139 A1 | 5/2018 | Seward et al. | |
| 2018/0153820 A1 | 6/2018 | Desai et al. | |
| 2018/0153863 A1 | 6/2018 | Desai et al. | |
| 2018/0169017 A1 | 6/2018 | Desai et al. | |
| 2018/0177770 A1 | 6/2018 | Desai et al. | |
| 2018/0177771 A1 | 6/2018 | Desai et al. | |
| 2018/0214425 A1 | 8/2018 | Desai et al. | |
| 2018/0256551 A1 | 9/2018 | Desai et al. | |
| 2018/0289620 A1 | 10/2018 | Desai et al. | |
| 2018/0374583 A1 | 12/2018 | Goldstein | |
| 2019/0022020 A1 | 1/2019 | Desai | |
| 2019/0054033 A1 | 2/2019 | Foss | |

FOREIGN PATENT DOCUMENTS

| | | |
|---|---|---|
| WO | WO 94/18954 A1 | 9/1994 |
| WO | WO 98/14174 A1 | 4/1998 |
| WO | WO 98/14175 A1 | 4/1998 |
| WO | WO 99/00113 A1 | 1/1999 |
| WO | WO-00/64437 A1 | 11/2000 |
| WO | WO 00/71079 A2 | 11/2000 |
| WO | WO 00/71079 A3 | 11/2000 |
| WO | WO 01/89522 A1 | 11/2001 |
| WO | WO 02/087545 A1 | 11/2002 |
| WO | WO 03/096944 A1 | 11/2003 |
| WO | WO 2004/052401 A2 | 6/2004 |
| WO | WO 2004/052401 A3 | 6/2004 |
| WO | WO 2006/089290 A1 | 8/2006 |
| WO | WO 2007/027819 A2 | 3/2007 |
| WO | WO 2007/027819 A3 | 3/2007 |

(56) References Cited

FOREIGN PATENT DOCUMENTS

| WO | WO 2007/027941 A2 | 3/2007 |
|---|---|---|
| WO | WO 2007/027941 A3 | 3/2007 |
| WO | WO 2008/027055 A1 | 3/2008 |
| WO | WO 2008/057562 A1 | 5/2008 |
| WO | WO 2008/076373 A1 | 6/2008 |
| WO | WO-2008/109163 A1 | 9/2008 |
| WO | WO-2008/137148 A2 | 11/2008 |
| WO | WO-2008/137148 A3 | 11/2008 |
| WO | WO 2008/150532 A1 | 12/2008 |
| WO | WO 2009/126175 A1 | 10/2009 |
| WO | WO 2009/126401 A1 | 10/2009 |
| WO | WO 2009/126938 A1 | 10/2009 |
| WO | WO 2010/068925 A1 | 6/2010 |
| WO | WO 2010/105172 A1 | 9/2010 |
| WO | WO 2010/118365 A1 | 10/2010 |
| WO | WO 2010/121000 A1 | 10/2010 |
| WO | WO-2011/025838 A1 | 3/2011 |
| WO | WO-2011/063309 A1 | 5/2011 |
| WO | WO-2011/119988 A1 | 9/2011 |
| WO | WO-2011/123393 A1 | 10/2011 |
| WO | WO-2011/123395 A1 | 10/2011 |
| WO | WO-2011/153009 A1 | 12/2011 |
| WO | WO-2011/153010 A1 | 12/2011 |
| WO | WO-2011/156119 A1 | 12/2011 |
| WO | WO-2012/149451 A1 | 11/2012 |
| WO | WO-2013/090634 A1 | 6/2013 |
| WO | WO-2014/105644 A1 | 7/2014 |
| WO | WO-2014/110345 A1 | 7/2014 |
| WO | WO-2014/110408 A1 | 7/2014 |
| WO | WO-2014/110443 A1 | 7/2014 |
| WO | WO-2014/123612 A1 | 8/2014 |
| WO | WO-2014/143613 A1 | 9/2014 |
| WO | WO-2014/151853 A1 | 9/2014 |
| WO | WO-2014/159171 A1 | 10/2014 |
| WO | WO-2015/157120 A1 | 10/2015 |

OTHER PUBLICATIONS

Hirsh et al. Weekly nab-Paclitaxel in Combination With Carboplatin as First-Line Therapy in Patients With Advanced None-Small-Cell Lung Cancer: Analysis of Safety and Efficacy in Patients With Diabetes. Clinical Lung Cancer, 2016, 17(5):367-374 (and references cited therein). (Year: 2016).*
Allerton, J.P. et al. (Jun. 20, 2006). "A Phase II Evaluation of the Combination of Paclitaxel Protein-Bound and Carboplatin in the First-Line Treatment of Advanced Non-Small Cell Lung Cancer (NSCLC)," 2006 ASCO Annual Meeting Proceedings (Post-Meeting Edition), vol. 24, No. 18S, Abstract No. 7127, one page.
Belani, C.P. et al. (Jan. 20, 2008)."Randomized, Phase III Study of Weekly Paclitaxel in Combination With Carboplatin Versus Standard Every-3-Weeks Administration of Carboplatin and Paclitaxel for Patients With Previously Untreated Advanced Non—Small-Cell Lung Cancer," *J. Clin. Oncol.* 26(3):468-473.
Belani, C.P. et al. (2005) "Elderly Subgroup Analysis of a Randomized Phase III Study of Docetaxel Plus Platinum Combinations Versus Vinorelbine Plus Cisplatin for First-Line Treatment of Advanced Non-Small Cell Lung Carcinoma (TAX 326)," *Cancer* 104:2766-2774.
Bonomi, P.D. et al. (Nov. 1989). "Combination Chemotherapy Versus Single Agents Followed by Combination Chemotherapy in Stage IV Non-Small-Cell Lung Cancer: A Study of the Eastern Cooperative Oncology Group," *J. Clin. Oncol.* 7(11):1602-1613.
Carter, D.C. et al. (1994). "Structure of Serum Albumin," *Adv. Protein. Chem.* 45:153-203.
Cerny T. et al. (1994). "Docetaxel (Taxotere™) is Active in Non-Small-Cell Lung Cancer: A Phase II Trial of the EORTC Early Clinical Trials Group (ECTG)," *Br. J. Cancer* 70:384-387.
Curry, S. et al. (Nov. 1998). "Crystal Structure of Human Serum Albumin Complexed With Fatty Acid Reveals an Asymmetric Distribution of Binding Sites," *Nat. Struct. Biol.* 5(9):827-835.

Depierre, A. et al. (Mar. 1988). "Phase II Study of Navelbine (NVB) in Non Small Cell Lung Cancer (NSCLC)," Annual Meeting of the American Society of Clinical Oncology, May 22-24, 1988, New Orleans, Louisiana, *Proceedings of the American Society of Clinical Oncology* 7:201, Abstract No. 778, one page.
Desai, N. et al. (Feb. 15, 2006). "Increased Antitumor Activity, Intratumor Paclitaxel Concentrations, and Endothelial Cell Transport of Cremophor-Free, Albumin-Bound Paclitaxel, ABI-007, Compared with Cremophor-Based Paclitaxel," *Clin. Cancer Res.* 12(4):1317-1324.
Dubey, S. et al. (Feb. 2004). "Chemotherapy for Advanced Non-Small Cell Lung Cancer" *Chemo. Hematol. Oncol. Clin. N. Am.* 18(1):101-114.
Fehske, K.J. et al. (Apr. 1, 1981). "The Location of Drug Binding Sites in Human Serum Albumin," *Biochem. Pharmcol.* 30(7):687-692.
Finlayson, J.S. (1980). "Albumin Products," *Seminars in Thrombosis and Hemostasis* 6(2):85-120.
Fossella F.V. et al. (Mar. 1995). "Phase II Study of Docetaxel for Advanced or Metastatic Platinum-Refractory Non-Small-Cell Lung Cancer," *J. Clin. Oncol.* 13(3):645-651.
Gatzemeier, U. et al. (1995). "Phase II study With Paclitaxel for the Treatment of Advanced Inoperable Non-Small Cell Lung Cancer," *Lung Cancer* 12:(Suppl 2):SI01-SI06.
Gelderblom, H. et al. (2001). "Cremophor EL: The Drawbacks and Advantages of Vehicle Selection for Drug Formulation," *Eur.J. Cancer* 37:1590-1598.
Goodman & Gilman. (1996) *The Phannacological Basis of Therapeutics*, 9th ed, McGraw-Hill New York, New York, pp. v-vii, (Table of Contents Only)(Total pages 10).
Green, M.R. et al.(2006, e-pub. Jun. 1, 2006). "Abraxane®, A Novel Cremophor®-Free, Albumin-Bound Particle Form of Paclitaxel for the Treatment of Advanced Non-Small-Cell Lung Cancer," *Ann. Oncol.* 17:1263-1268.
Gridelli, C. (2002). "Does Chemotherapy Have a Role as Palliative Therapy for Unfit or Elderly Patients With Non-Small Cell Lung Cancer?" *Lung Cancer.* 28:S45-S50.
Grilli, R. et al. (Oct. 1993). "Chemotherapy for Advanced Non-Small-Cell Lung Cancer: How Much Benefit Is Enough?," *J. Clin. Oncol.* 11(10):1866-1872.
Hainsworth, J.D. et al.(1995). "Paclitaxel by 1-Hour Infusion: An Active Drug in Metastatic Non-Small-Cell Lung Cancer" *J Clin Oncol.* 13(7):1609-1614.
Hauser, C.J. et al. (Jun. 1980). "Oxygen Transport Responses to Colloids and Crystalloids in Critically Ill Surgical Patients," *Surgery, Gynecology and Obstetrics* 150(6):811-816.
He, X.M. et al. (Jul. 16, 1992). "Atomic Structure and Chemistry of Human Serum Albumin," *Nature* 358:209-15.
Herbst, R.S. et al. (2004). "Gefitinib in Combination With Paclitaxel and Carboplatin in Advanced Non-Small-Cell Lung Cancer: A Phase III Trial-INTACT 2," *J. Clin. Oncol.* 22:785-794.
Kelly, K. et al. (Jul. 1, 2001). "Randomized Phase III Trial of Paclitaxel Plus Carboplatin Versus Vinorelbine Plus Cisplatin in the Treatment of Patients With Advanced Non-Small-Cell Lung Cancer: A Southwest Oncology Group Trial," *J. Clin. Oncol.* 19(13):3210-3218.
Koukourakis, M.I. et al. (Sep. 1, 2003, e-pub. Sep. 18, 2003). "Enhanced Expression of SPARC/Osteonectin in the Tumor-Associated Stroma of Non-Small Cell Lung Cancer Is Correlated with Markers of Hypoxia/ Acidity and with Poor Prognosis of Patients," *Cancer Research.* 63:5376-5380.
Kragh-Hansen, U. (1990). "Structure and Ligand Binding Properties of Human Serum Albumin," *Dan. Med. Bull.* 1441:131-40.
Kudoh, S. et al. (Aug. 1, 2006) "Phase III Study of Docetaxel Compared With Vinorelbine in Elderly Patients With Advanced Non-Small-Cell Lung Cancer: Results of the West Japan Thoracic Oncology Group Trial (WJTOG 9904)," *J. Clin. Oncol.* 24(22):3657-3663.
Lilenbaum, R.C. et al. (Jun. 2002). "Single-Agent (SA) Versus Combination Chemotherapy (CC) in Advanced Non-Small Cell Lung Cancer (NSCLC): A CALGB Randomized Trial of Efficacy,

(56) References Cited

OTHER PUBLICATIONS

Quality of Life (QOL), and Cost-Effectiveness," *Presented at: American Society of Clinical Oncology (ASCO)*, Jun. 2002. Abstract No. 2, three pages.

Lilliambum, R.C. et al. (2005) "Single-Agent Versus Combination Chemotherapy in Advanced Non-Small-Cell Lung Cancer: the Cancer and Leukemia Group B (study 9730)." *J. Clin. Oncol.* 23:190-196.

Lorenz, W. et al. (1977). "Histamine Release in Dogs by Cremophor El® and its Derivatives: Oxethylated Oleic Acid is the Most Effective Constituent," *Agents and Actions* 7:63-67.

Lynch, T.J. et al. (2010). "Cetuximab and First-Line Taxane/Carboplatin Chemotherapy in Advanced Non-Small-Cell Lung Cancer: Results of the Randomized Multicenter Phase III Trial BMS099," *J. Clin. Oncol.* 28(6):911-917.

Mielke, S. et al. (2006) "Peripheral Neuropathy: a Persisting Challenge in Paclitaxel-Based Regimes," *Eur. J. Cancer* 42:24-30.

Müller, B.G. et al. (1996). "Albumin Nanospheres as Carriers for Passive Drug Targeting: An Optimized Manufacturing Technique," *Pharmaceutical Research* 13(1):32-37.

Paál, K. et al. (2001). "High Affinity Binding of Paclitaxel to Human Serum Albumin" *Eur. J. Biochem.* 268(7):2187-91.

Porter, P.G. et al. (1995). "Distribution of SPARC in Normal and Neoplastic Human Tissue," *J. Histochem. Cytochem.* 43:791-800.

Quiox, E. (2011) "Optimal Pharmacotherapeutic Strategies for Elderly Patients With Advanced Non-Small Cell Lung Cancer," *Drugs Aging* 28(11):885-894.

Quoix ,E. et al. (2011) "Carboplatin and Weekly Paclitaxel Doublet Chemotherapy Compared With Monotherapy in Elderly Patients With Advanced Non-Small-Cell Lung Cancer: IFCT-0501 Randomized, Phase 3 Trial," *Lancet.* 378:1079-1088.

Rapp, E. et al. (Apr. 1988). "Chemotherapy Can Prolong Survival in Patients With Advanced Non-Small-Cell Lung Cancer—Report of a Canadian Multicenter Randomized Trial," *J. Clin. Oncol.* 6(4):633-641.

Reynolds, C. et al. (Dec. 2009). "Phase II Trial of Nanoparticle-Albumin-Bound Paclitaxel, Carboplatin, and Bevacizumab in First-line Patients with Advanced Nonsquarmous Non-small Cell Lung Cancer," *Journal of Thoracic Oncology* 4(12):1537-1543.

Rizvi, N.A. et al. (Jun. 20, 2006). "Phase I/II Study of ABI-007 as First Line Chemotherapy in Advanced Non-Small Cell Lung Cancer (NSCLC)." *J Clin Oncol.*, 2006 Single-agent versus combination chemotherapy in advanced non-small-cell lung cancer: the Cancer and Leukemia Group B (study 9730)ASCO Annual Meeting Proceedings (Post-Meeting Edition). vol. 24, No. 18S, Abstract No. 7105, three pages.

Rizvi, N.A. et al. (Feb. 1, 2008). Phase I/II Trial of Weekly Intravenous 130-nm Albumin-Bound Paclitaxel as Initial Chemotherapy in Patients With Stage IV Non-Small-Cell Lung Cancer, *Journal of Clinical Oncology* 26(4):639-643.

Scagliotti G.V. et al. (2002). "Phase III Randomized Trial Comparing Three Platinum-Based Doublets in Advanced Non-Small-Cell Lung Cancer" *J. Clin. Oncol.* 20:4285-4291.

Scagliotti, G.V. et al. (2008). "Phase III Study Comparing Cisplatin Plus Gemcitabine With Cisplatin Plus Pemetrexed in Chemotherapy-Naïve Patients With Advanced-Stage Non-Small-Cell Lung Cancer" *J Clin Oncol.* 26(21 )3543-3551.

Schiller J.H. et al.(2002). "Comparison of Four Chemotherapy Regimens for Advanced Non-Small-Cell Lung Cancer" *N. Engl. J. Med.* 346:92-98.

Seer Cancer Statistics Review. (2012). "Estimated New Cancer Cases and Deaths for 2012 All Races, by Sex," Table 1.1, *National Cancer Institute*, 1 page.

Shepherd, F.A. (1995). "Phase II Trials of Single-Agent Activity of Gemcitabine in Patients With Advanced Non-Small Cell Lung Cancer: An Overview," *Anticancer Drugs* 6(Suppl 6):19-25.

Socinski, M.A. et al. (2012, e-pub. Apr. 30, 2012). "Weekly *nab-*Paclitaxel in Combination With Carboplatin Versus Solvent-Based Paclitaxel Plus Carboplatin as First-Line Therapy in Patients With Advanced Non-Small-Cell Lung Cancer: Final Results of a Phase III Trial," *J. Clin. Oncol.* 30:2055-2062.

Socinski, M.A. et al., (Feb. 2013). "Safety and Efficacy of Weekly Nab®-Paclitaxel in Combination With Carboplatin as First-Line Therapy in Elderly Patients With Advanced Non-Small-Cell Lung Cancer," *Annuals of Oncology* 24(2):314-321.

Sorensen, J.B. (1995). "Gemcitabine in Non-Small. Cell Lung Cancer," *Lung Cancer* 12 (Suppl I):SI 73-SI 75.

Souquet, P.J. et al. (Jul. 3, 1993). "Polychemotherapy in Advanced Non Small Cell Lung Cancer: A Meta-Analysis," *Lancet* 342(8862):19-21.

Sparreboom, A. et al. (Apr. 1, 1999). "Cremophor EL-Mediated Alteration of Paclitaxel Distribution in Human Blood: Clinical Pharmacokinetic Implications" *Cancer Res.* 59(7):1454-1457.

Stewart, L.A. et al. (Oct. 7, 1995). "Chemotherapy in Non-Small Cell Lung Cancer: A Meta-Analysis Using Updated Data on Individual Patiens From 52 Randomised Clinical Trials. Non Small Cell Lung Cancer Collaborative Group," *Br. Med. J.* 311:899-909.

Sugio, S. et al. (1999). "Crystal Structure of Human Serum Albumin at 2.5 A Resolution," *Protein. Eng.* 12(6):439-446.

Ten Tije, A.I. et al. (2003). "Pharmacological Effects of Formulation Vehicles," *Clin. Pharmacokinet.* 42(7):665-685.

Therasse, P. et al. (Feb. 2, 2000). "New Guidelines to Evaluate the Response to Treatment in Solid Tumors," *J. Natl. Cancer Inst.* 92(3):205-216.

Tullis, J.L. (Jan. 24, 1977). "Albumin 1. Background and Use," *JAMA* 237(4):355-360.

Tullis, J.L. (Jan. 31, 1977). "Albumin 2. Guidelines for Clinical Use," *JAMA* 237(5):460-463.

Van Tellingen, O. et al. (Sep. 1999). "Cremophor EL Causes (Pseudo-) Non-Linear Pharmacokinetics of Paclitaxel in Patients," *Br. J. Cancer* 81(2):330-335.

Vorum H. (1999). "Reversible Ligand Binding to Human Serum Albumin," *Dan. Med. Bull.* 46:379-99.

Weiss, R.B. et al.(Jul. 1990). "Hypersensitivity Reactions From Taxol," *J. Clin. Oncol.* 8(7):1263-1268.

Yoo, S-H. et al. (2003). "Expression of Caveolin-1 is Associated With Poor Prognosis of Patients With Squamous Cell Carcinoma of the Lung," *Lung Cancer* 42:195-202.

International Search Report dated Jun. 11, 2014, for PCT Application No. PCT/US2014/022341, filed on Mar. 10, 2014, 3 pages.

Written Opinion dated Jun. 11, 2014, for PCT Application No. PCT/US2014/022341, filed on Mar. 10, 2014, 5 pages.

U.S. Appl. No. 14/714,131, filed May 15, 2015, by Seward et al.

U.S. Appl. No. 14/835,458, filed Aug. 25, 2015, by Desai et al.

Desai, N. (2007/2008). "Nab Technology: A Drug Delivery Platform Utilising Endothelial gp60 Receptor-based Transport and Tumour-derived SPARC for Targeting," *Drug Delivery Report Winter* 2007/2008 pp. 37-41.

Hawkins, M.J. et al. (Jun. 20, 2006). "Dose Escalation Study of Nab-Paclitaxel Followed by Carboplatin as First Line Therapy in Advanced Non-Small Cell Lung Cancer (NSCLC)." *Journal of Clinical Oncology* 24(18S): Abstract No. 7132, (Abstract only—one page).

Howlader N, et al (eds). (2010, e-published in 2011). "SEER Cancer Statistics Review, 1975-2008," *National Cancer Institute*; Bethesda, MD, (Table of Contents only—three pages).

Socinski, M. A. et al. (Aug. 1, 2009). "PD3.3.4-Retrospective Analysis of a Phase II Study of nab-Paclitaxel plus Carboplatin in Advanced NSCLC: Response Based on Histology," Poster-Discussion presented as an Abstract at the *13th World Conference on Lung Cancer*, held in San Francisco, CA, on Jul. 31-Aug. 4, 2009, under NSCLC-Advanced Disease I, organized by the International Association for the Study of Lung Cancer, 9 pages (Poster).

Winer, E. et al. (1998). "Failure of Higher Dose Paclitaxel to Improve Outcome in Patients With Metastatic Breast Cancer—Results From CALGB 9342 (Meeting abstract)." *Proceedings of American Society of Clinical Oncology* 1998, vol. 17, Abstract No. 388, (Abstract only—three pages).

European Supplemental Search Report dated Oct. 27, 2016, for European Patent Application No. 14776420.3, filed on Oct. 9, 2015, 7 pages.

(56) References Cited

OTHER PUBLICATIONS

Extended European Search Report dated Feb. 10, 2017, for European Patent Application No. 14776420.3, filed on Oct. 9, 2015, 9 pages.
Rossi, D. et al. (Sep. 2008). "Weekly Paclitaxel in Elderly Patients (Aged ≥ 70 years) with Advanced Non-Small-Cell Lung Cancer: An Alternative Choice? Results of a Phase II Study," *Clin. Lung Cancer* 9(5):280-284.
Zheng, Q. et al. (2012, e-pub. May 20, 2012). "Weekly Intravenous Nanoparticle Albumin-Bound Paclitaxel for Elderly Patients With Stage IV Non-Small-Cell Lung Cancer: A Series of 20 Cases," *Journal of Biomedical Research* 26(3):159-164.
U.S. Appl. No. 15/399,366, filed Jan. 5, 2017, for Pierce et al.
U.S. Appl. No. 15/462,361, filed Mar. 17, 2017, for Tao et al.
U.S. Appl. No. 15/663,351, filed Jul. 28, 2017, for Desai et al.
U.S. Appl. No. 15/669,821, filed Aug. 4, 2017, for Desai et al.
U.S. Appl. No. 15/555,310, internationally filed Mar. 4, 2016, for Pierce et al.
U.S. Appl. No. 15/714,954, filed Sep. 25, 2017, for Desai et al.
U.S. Appl. No. 15/782,630, filed Oct. 12, 2017, for Foss et al.
U.S. Appl. No. 15/787,586, filed Oct. 18, 2017, for Desai et al.
U.S. Appl. No. 15/796,578, filed Oct. 27, 2017, for Desai et al.
U.S. Appl. No. 15/820,022, filed Nov. 21, 2017, for Desai et al.
Bando, T. et al. (1997). "Exposure to Sorbitol Induces Resistance to Cisplatin in Human Non-Small-Cell Lung Cancer Cell Lines," *Anticancer Research* 17:3345-3348.
F. Hoffmann-La Roche LTD. (2013). "Understanding Clinical Trials," *Hoffmann-La Roche Ltd.*, 13 pages.
Inal, A. et al. (2014, e-pub. Nov. 6, 2013). "Is Diabetes Mellitus a Negative Prognostic Factor for the Treatment of Advanced Non-Small-Cell Lung Cancer?," *Rev. Port. Pneumo.* 20(2):62-68.
Kang, X. et al. (2015, e-pub. Feb. 2, 2015). "High Glucose Promotes Tumor Invasion and Increases Metastasis-Associated Protein Expression in Human Lung Epithelial Cells by Upregulating Heme Oxygenase-1 via Reactive Oxygen Species or the TGF-β1/PI3K/Akt Signaling Pathway," *Cell Physiol. Biochem.* 35:1008-1022.
Stewart, D.J. et al. (Sep. 2010). "Tumor and Host Factors That May Limit Efficacy of Chemotherapy in Non-Small Cell and Small Cell Lung Cancer," *Crit. Rev. Oncol. Hematol.* 75(3):173-234, 101 pages.
U.S. Appl. No. 15/981,276, filed May 16, 2018, for Desai et al. (A U.S. Patent Application is not submitted herewith pursuant to the waiver of 37 C.F.R. § 1.98(a)(2)(iii) issued by the Office on Sep. 21, 2004.).
U.S. Appl. No. 16/101,027, filed Aug. 10, 2018, for Desai et al. (A U.S. Patent Application is not submitted herewith pursuant to the waiver of 37 C.F.R. § 1.98(a)(2)(iii) issued by the Office on Sep. 21, 2004.).
U.S. Appl. No. 16/107,419, filed Aug. 21, 2018, for Foss et al. (A U.S. Patent Application is not submitted herewith pursuant to the waiver of 37 C.F.R. § 1.98(a)(2)(iii) issued by the Office on Sep. 21, 2004.).
U.S. Appl. No. 16/140,339, filed Sep. 24, 2018, for Desai et al. (A U.S. Patent Application is not submitted herewith pursuant to the waiver of 37 C.F.R. § 1.98(a)(2)(iii) issued by the Office on Sep. 21, 2004.).
U.S. Appl. No. 16/170,522, filed Oct. 25, 2018, for Desai et al. (A U.S. Patent Application is not submitted herewith pursuant to the waiver of 37 C.F.R. § 1.98(a)(2)(iii) issued by the Office on Sep. 21, 2004.).
U.S. Appl. No. 16/284,995, filed Feb. 25, 2019, for Desai et al. (A U.S. Patent Application is not submitted herewith pursuant to the waiver of 37 C.F.R. § 1.98(a)(2)(iii) issued by the Office on Sep. 21, 2004.).

\* cited by examiner

METHODS OF TREATING LUNG CANCER

RELATED APPLICATIONS

This application is a National Phase application under 35 U.S.C. § 371 of International Application No. PCT/US2014/022341 filed Mar. 10, 2014, which claims priority from U.S. Provisional Application No. 61/778,299, filed Mar. 12, 2013, the contents of which are herein incorporated by reference in their entirety.

TECHNICAL FIELD

The present invention relates to methods and compositions for the treatment of non-small-cell lung cancer (NSCLC) by administering compositions comprising nanoparticles that comprise paclitaxel and an albumin and a platinum-based agent (e.g. carboplatin).

BACKGROUND

Lung cancer is the leading cause of cancer death in both men and women in the United States. In 1998, an estimated 171,500 new cases were diagnosed, and about 160,100 deaths resulted from this disease. More women die from lung cancer than breast, ovarian, and uterine cancer combined, and 4 times as many men die from lung cancer than from prostate cancer. Most patients who are diagnosed with NSCLC cannot be cured with surgery and will eventually die from their disease. See SEER Cancer Statistics Review 2001. The median survival of patients with untreated metastatic NSCLC is only four to five months with a survival rate at one year of only 10 percent. Rapp E. et al. *J Clin Oncol.* 1988; 6:633-41.

Chemotherapy only moderately improves the median survival time (MST) of patients with locally advanced or metastatic NSCLC when compared to best supportive care (BSC). The first generation of chemotherapy agents extended the survival of patients with stage IIIB and IV NSCLC by 10% to 15%, when compared to BSC. Several meta-analyses indicate that cisplatin-containing regimens confer an increase of 6 to 8 weeks in MST and of 15% to 25% in 1-year survival. See Non-Small Cell Lung Cancer Collaborative Group. *Br Med J.* 1995; 311:899-909; Grilli R. et al. *J Clin Oncol.* 1993; 11:1866-1872; Souquet P. J. et al. *Lancet* 1993; 342:19-21. The most commonly used agents to treat NSCLC include carboplatin (response rate (RR): 20%-25%; see Bonomi P. D. et al. *J Clin Oncol.* 1989; 7:1602-13), paclitaxel dissolved in polyoxyethylated castor oil and dehydrated alcohol, sold under the trademark TAXOL® (RR: 20%-25%; see Gatzemeier U. et al. Lung Cancer. 1995; 12(Suppl 2):S101-5106; Hainsworth J. D. et al. J Clin Oncol, 1995. 13(7):1609-1614), docetaxel (RR: 23%-33%; see Fossella F. V. et al. *J Clin Oncol.* 1995; 13(3):645-651; Cerny T. et al. *Br J Cancer.* 1994; 70:384-387), gemcitabine (RR: 20%-25%; see Shepherd F. A. *Anticancer Drugs.* 1995; 6(Suppl 6):9-25; Sorensen J. B. *Lung Cancer.* 1995; 12 (Suppl 1):5173-5175), and vinorelbine (RR: 29.4%; see Depierre A. et al. *Proc ASCO,* 1988. 7:201). The MST for these drugs varies from 7.5 to 9.5 months.

Most treatment combinations to date center on the use of platinum-based regimens. Platinum-based agents are alkylating agents which bind covalently to DNA and cross-links DNA strands, resulting in inhibition of DNA synthesis and function as well as inhibition of transcription. Platinum-based chemotherapy combinations have demonstrated improvements over single-agent therapy in advanced NSCLC. See Dubey S. and Schiller J. H. *Hematol Oncol Clin N Am.* 2004; 18:101-114. For example, paclitaxel dissolved in polyoxyethylated castor oil and dehydrated alcohol, sold under the trademark TAXOL® (200-225 mg/m$^2$) in combination with carboplatin (area under curve (AUC)=6) administered q3w is a commonly used and well accepted treatment regimen for patients with NSCLC, producing objective response rates in Phase III studies of 17%, 25%, 29%, 32%, and 37%. See Schiller J. H. et al. *N Engl J Med.* 2002; 346:92-98; Kelly K. et al. *J Clin Oncol.* 2001; 19:3210-3218; Herbst R. S. et al. *J Clin Oncol.* 2004; 22:785-794; Scagliotti G. V. et al. *J Clin Oncol.* 2002; 20:4285-4291; Lilenbaum R. C. et al. *Presented at: American Society of Clinical Oncology (ASCO),* June 2002. Abstract 2. Toxicities associated with this regimen were similar in nature to those associated with paclitaxel dissolved in polyoxyethylated castor oil and dehydrated alcohol, sold under the trademark TAXOL® and carboplatin individually, and the combination demonstrated no new or unexpected toxicities. The efficacy parameters were similar between paclitaxel dissolved in polyoxyethylated castor oil and dehydrated alcohol, sold under the trademark TAXOL® 100 mg/m$^2$ weekly for 3 of 4 weeks with carboplatin AUC=6 and paclitaxel dissolved in polyoxyethylated castor oil and dehydrated alcohol, sold under the trademark TAXOL® 100 mg/m$^2$ and carboplatin AUC=6 on day 1 of each 3-week cycle. See Belani et al. *J Clin Oncol.* 2008; 26(3):468-473.

A recent Phase III study comparing carboplatin/paclitaxel dissolved in polyoxyethylated castor oil and dehydrated alcohol, sold under the trademark TAXOL® to other doublets (cisplatin/paclitaxel dissolved in polyoxyethylated castor oil and dehydrated alcohol, sold under the trademark TAXOL® vs. cisplatin/gemcitabine vs. cisplatin/docetaxel vs. carboplatin/paclitaxel dissolved in polyoxyethylated castor oil and dehydrated alcohol, sold under the trademark TAXOL®) demonstrated that all the combinations have similar efficacy. See Schiller J. H. et al. *N Engl J Med.* 2002; 346:92-98. However, because of its more favorable safety profile, the Eastern Collaborative Oncology Group (ECOG) selected carboplatin/paclitaxel dissolved in polyoxyethylated castor oil and dehydrated alcohol, sold under the trademark TAXOL® as its reference regimen for future studies. See Schiller J. H. et al. *N Engl J Med.* 2002; 346:92-98.

Paclitaxel dissolved in polyoxyethylated castor oil and dehydrated alcohol, sold under the trademark TAXOL® (Bristol-Myers Squibb Co., Princeton, N.J.) contains the chemotherapeutic active agent paclitaxel. Paclitaxel binds to the β-subunit of tubulin, the building blocks of microtubules, causing hyper-stabilization of the microtubule structures. The resulting paclitaxel/microtubule structure is unable to disassemble, thereby arresting mitosis and inhibiting angiogenesis. Because paclitaxel is highly hydrophobic, commercially available formulations include synthetic solvents to enable parenteral administration: paclitaxel dissolved in polyoxyethylated castor oil and dehydrated alcohol, sold under the trademark TAXOL® contains a combination of polyoxyethylated castor oil, sold under the trademark CREMOPHOR® EL and ethanol as paclitaxel vehicle.

The solvent used in paclitaxel dissolved in polyoxyethylated castor oil and dehydrated alcohol, sold under the trademark TAXOL® raises major concerns due to its intrinsic negative properties. Emerging data indicate that polyoxyethylated castor oil, sold under the trademark CREMOPHOR® is a biologically and pharmacologically active compound that directly contributes to the severe toxicities observed in patients treated with paclitaxel dissolved in polyoxyethylated castor oil and dehydrated alcohol, sold under the trademark TAXOL®. Among the well-characterized, solvent-related toxicities are severe hypersensitivity reactions (which can be fatal even with steroid premedication); histamine release; and prolonged, sometimes irreversible peripheral neuropathy associated with demyelination and axonal degeneration. See Gelderblom H. et al. *Eur J Cancer.* 2001; 37:1590-8. Review; Lorenz W. et al. *Agents and Actions* 1977; 7:63-67; Weiss R. B. et al. *J Clin Oncol.* 1990; 8:1263-1268. Furthermore, these solubilizers adversely affect efficacy due to entrapment of active drug in micelles formed in the plasma compartment. See ten Tije A. J. et al. *Clin Pharmacokinet.* 2003; 42:665-85. Review. Such entrapment alters drug pharmacokinetics (PK), leading to highly increased systemic drug exposure, decreased drug clearance, nonlinear PK, and lack of dose-dependent antitumor activity. See ten Tije A. J. et al. *Clin Pharmacokinet.* 2003; 42:665-85. Review; Winer E. et al. *Proceedings of ASCO* 1998, Vol 17, Abstract 388; Sparreboom A. et al. *Cancer Res.* 1999; 59(7):1454-1457; van Tellingen O. et al. *Br J Cancer.* 1999; 81:330-5. Drug entrapment affects not only the taxanes but also co-administered drugs (e.g., anthracyclines, platinum compounds) and, thus, is an important consideration in the design of combination therapies. See ten Tije A. J. et al. *Clin Pharmacokinet.* 2003; 42:665-85. Review.

As emerging data have indicated that the solvent used in paclitaxel dissolved in polyoxyethylated castor oil and dehydrated alcohol, sold under the trademark TAXOL® may negatively impact the efficacy and toxicity profile of chemotherapy comprising paclitaxel dissolved in polyoxyethylated castor oil and dehydrated alcohol, sold under the trademark TAXOL®, new paclitaxel formulations have been developed. Nab-paclitaxel (or ABI-007), sold under the trademark ABRAXANE®; Abraxis BioScience, Los Angeles, Calif.) is a novel, solvent-free, non-crystalline, amorphous, albumin-bound, paclitaxel particle with a mean size of approximately 130 nm suspended in normal saline See, for example, U.S. Pat. Nos. 5,916,596; 6,506,405; 6,749,868, 6,537,579, and 7,820,788 and also in U.S. Pat. No. 8,034,375. Nab-paclitaxel is the first of a new class of anticancer agents that incorporate particle technology and exploit the unique properties of albumin, a natural carrier of lipophilic molecules in humans. Nab-paclitaxel utilizes the albumin receptor (gp60)/caveolin-1 (CAV1) pathway achieving high intratumoral paclitaxel accumulation. See Desai et al. *Clin Cancer Res* 2006; 12(4):1317-1324. Nab-paclitaxel has advantages compared to paclitaxel dissolved in polyoxyethylated castor oil and dehydrated alcohol, sold under the trademark TAXOL® with regards to reduced toxicity, greater ease of administration, shorter drug infusion time, and avoidance of hypersensitivity reactions.

Nab-paclitaxel, when administered at a dose of 260 mg/m$^2$ every 3 weeks to 43 patients with NSCLC as first-line therapy, resulted in an objective response rate of 16% with an additional 49% of patients achieving disease control (defined as stable disease for at least 16 weeks plus objective responses) and was well tolerated with no patients developing any Grade 4 toxicity at any time during the treatment course. See Green M. R. et al. *Ann Oncol.* 2006; 17:1263-8. When Nab-paclitaxel was given at a dose of 125 mg/m$^2$ weekly for 3 weeks followed by one week off to 40 elderly patients with Stage IV NSCLC (median age 70), the objective response and disease control rates were 30% and 50% respectively. See Rizvi N. A. et al. *J Clin Oncol.,* 2006 ASCO Annual Meeting Proceedings (Post-Meeting Edition). Vol 24, No 18S (June 20 Supplement), 2006: 7105.

A high monotherapy response rate does not necessarily translate into a significantly higher combination therapy response rate in a Phase III trial, let alone result in additive efficacy. See Lynch et al. *J Clin Oncol.* 2010; 28(6):911-917 ("More than a dozen phase III trials have unsuccessfully investigated targeted approaches combined with platinum doublets.").

In view of the improved objective response rates compared to paclitaxel dissolved in polyoxyethylated castor oil and dehydrated alcohol, sold under the trademark TAXOL®, Nab-paclitaxel was combined with carboplatin to evaluate efficacy and toxicity in NSCLC. In 100 patients treated with carboplatin (area under curve (AUC)=6) plus Nab-paclitaxel every 3 weeks at doses between 225 and 340 mg/m$^2$, the overall response rate was 27% (see Hawkins M. J. et al. *J Clin Oncol.,* 2006 ASCO Annual Meeting Proceedings (Post-Meeting Edition). Vol 24, No 18S (June 20 Supplement), 2006: 7132) and a 50% response rate was reported using 100 mg/m$^2$ Nab-paclitaxel weekly in combination with carboplatin in NSCLC patients (see Allerton J. P. et al. *J Clin Oncol.,* 2006 ASCO Annual Meeting Proceedings (Post-Meeting Edition). Vol 24, No 18S (June 20 Supplement), 2006: 7127). Further, in another study, NSCLC patients with histologic confirmation of adenocarcinoma receiving Nab-paclitaxel weekly in combination with carboplatin achieved a 59% ORR while NSCLC patients with histologic confirmation of squamous cell carcinoma achieved a 39% ORR. See Socinski M. A. et al. *IASLC, 13$^{th}$ Word Conference on Lung Cancer.* San Francisco, Calif.; Jul. 31-Aug. 4, 2009.

Further data is emerging that NSCLC is a diverse cancer with treatment and survival outcomes often dependent upon the histology of the malignancy and the molecule profile of the NSCLC. For example, survival analysis has previously shown a significant association of stromal Secreted Protein Acidic and Rich in Cysteine (SPARC) (also known as osteonectin and BM40) with markers of hypoxia/acidity and with poor prognosis in non-small cell lung cancer. See Koukourakis et al. *Cancer Research.* 2003. 63:53756-5380. In addition, previous studies also have indicated that histology can be an important predictor for clinical response. In a NSCLC Phase III trial comparing cisplatin plus gemcitabine with cisplatin plus pemetrexed, for example, the use of cisplatin and pemetrexed in patients with adenocarcinoma and large-cell carcinoma resulted in significantly better survival than cisplatin and gemcitabine therapy while no significant difference was observed in squamous cell carcinoma. See Scagliotti et al. *J Clin Oncol.* 2008; 26(21)3543-3551. Squamous cell carcinoma of the lung accounts for one-third of primary lung cancer and a common malignant tumor with poor prognosis. In squamous cell carcinoma, advanced pathologic stage and poor prognosis have been correlated with increased caveolin-1 expression. Yoo et al. *Lung Cancer.* 2003 42:195-202.

The continued evaluation of new approaches to treat NSCLC is imperative to increase survival and quality of life of for NSCLC patients.

The disclosures of all publications, patents, patent applications and published patent applications referred to herein are hereby incorporated herein by reference in their entirety.

BRIEF SUMMARY OF THE INVENTION

Provided herein are methods of treating non-small-cell lung cancer (NSCLC) in an individual, comprising administering to the individual (a) an effective amount of a composition comprising nanoparticles comprising paclitaxel and albumin (hereinafter also referred to as "the nanoparticle composition" or "paclitaxel nanoparticle composition"); and (b) an effective amount of a platinum-based agent.

In some embodiments, there is provided a method of treating NSCLC in an individual, comprising administering to the individual (a) an effective amount of a composition comprising nanoparticles comprising paclitaxel and albumin; and (b) an effective amount of a platinum-based agent; wherein the individual has diabetes (or an elevated blood glucose level). In some embodiments, there is provided a method of treating NSCLC in an individual, comprising administering to the individual (a) an effective amount of a composition comprising nanoparticles comprising paclitaxel and albumin; and (b) an effective amount of a platinum-based agent; wherein the individual has four or more metastatic sites. In some embodiments, there is provided a method of treating NSCLC in an individual, comprising administering to the individual (a) an effective amount of a composition comprising nanoparticles comprising paclitaxel and albumin; and (b) an effective amount of a platinum-based agent; wherein the individual is at least about 70 years old. In some embodiments, there is provided a method of treating NSCLC in an individual, comprising administering to the individual (a) an effective amount of a composition comprising nanoparticles comprising paclitaxel and albumin; and (b) an effective amount of a platinum-based agent; wherein the individual is diabetic (or an elevated blood glucose level) and has four or more metastatic sites. In some embodiments, there is provided a method of treating NSCLC in an individual, comprising administering to the individual (a) an effective amount of a composition comprising nanoparticles comprising paclitaxel and albumin; and (b) an effective amount of a platinum-based agent; wherein the individual is diabetic (or an elevated blood glucose level) and is at least about 70 years old. In some embodiments, there is provided a method of treating NSCLC in an individual, comprising administering to the individual (a) an effective amount of a composition comprising nanoparticles comprising paclitaxel and albumin; and (b) an effective amount of a platinum-based agent; wherein the individual is diabetic (or an elevated blood glucose level), has at least four metastatic sites, and is at least about 70 years old.

In some embodiments, the NSCLC is squamous cell carcinoma (i.e., epidermoid carcinoma), large cell carcinoma, adenocarcinoma, adenosquamous carcinoma, carcinomas with pleomorphic, sarcomatoid, or sarcomatous elements, carcinoid tumor, or salivary gland carcinoma. In some embodiments, the NSCLC is squamous cell carcinoma. In some embodiments, the NSCLC is an occult tumor, a stage 0 tumor, a stage I tumor, a stage II tumor, a stage IIIA tumor, a stage IIIB tumor, or a stage IV tumor. In some embodiments, the NSCLC is early stage NSCLC, non-metastatic NSCLC, primary NSCLC, advanced NSCLC, locally advanced NSCLC, metastatic NSCLC, NSCLC in remission, or recurrent NSCLC. In some embodiments, the NSCLC is localized resectable, localized unresectable, or unresectable. In some embodiments, the NSCLC is inoperable Stage IIIA and/or IIIB NSCLC, PS 0-1, and FEV 1>800 ml. In some embodiments, the method is for treating NSCLC as first-line therapy or second-line therapy. In some embodiments, the individual to be treated is ineligible for VEGF-directed therapy, for example, ineligible for treatment with bevacizumab. In some embodiments, the individual is at risk of bleeding from VEGF directed therapy.

In some embodiments, the dose of paclitaxel in the composition comprising nanoparticles comprising paclitaxel and the albumin is between about 50 mg/m$^2$ to about 125 mg/m$^2$ (e.g., 50 mg/m$^2$, 75 mg/m$^2$, or 100 mg/m$^2$) and the effective amount of the platinum-based agent is between about AUC=2 to about AUC=6 (e.g., AUC=3, AUC=4.5, or AUC=6). In some embodiments, the effective amount of the composition comprising nanoparticles comprising paclitaxel and the albumin is administered weekly and the effective amount of the platinum-based agent is administered every three weeks. In some embodiments, the dose of paclitaxel in the composition comprising nanoparticles comprising paclitaxel and the albumin is between about 50 mg/m$^2$ to about 125 mg/m$^2$ administered weekly and the effective amount of the platinum-based agent is between about AUC=2 to about AUC=6 administered once every three weeks. In some embodiments, the dose of paclitaxel in the composition comprising nanoparticles comprising paclitaxel and the albumin is about 100 mg/m$^2$ administered weekly and the effective amount of the platinum-based agent is about AUC=6 administered once every three weeks. In some embodiments, the dose of paclitaxel in composition comprising nanoparticles comprising paclitaxel and the albumin is about 75 mg/m$^2$ administered weekly and the effective amount of the platinum-based agent is about AUC=4.5 administered once every three weeks. In some embodiments, the dose of paclitaxel in the composition comprising nanoparticles comprising paclitaxel and the albumin is about 50 mg/m$^2$ administered weekly and the effective amount of the platinum-based agent is about AUC=3 administered once every three weeks. In some embodiments, the paclitaxel nanoparticle composition and/or the platinum-based agent is administered intravenously. In some embodiments, the paclitaxel nanoparticle composition and the platinum-based agent are administered intravenously.

In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises nanoparticles comprising paclitaxel coated with human serum albumin, wherein the nanoparticles have an average size of no more than about 150 nm (such as about 130 nm), wherein the weight ratio of human albumin and paclitaxel in the composition is about 9:1. In some embodiments, the composition comprises the albumin stabilized nanoparticle formulation of paclitaxel (Nab-paclitaxel), sold under the trademark ABRAXANE®). In some embodiments, the composition is Nab-paclitaxel, i.e., the albumin stabilized nanoparticle formulation of paclitaxel sold under the trademark ABRAXANE®.

In some embodiments, the platinum-based agent binds covalently to DNA and cross-links strands, inhibits DNA synthesis, and/or inhibits transcript. In some embodiments, the platinum-based agent is carboplatin, cisplatin, or oxaliplatin. In some embodiments, the platinum-based agent is carboplatin. In some embodiments, the platinum-based agent is cisplatin.

In some embodiments, the composition comprising nanoparticles comprising paclitaxel and an albumin and the platinum-based agent are sequentially administered, concurrently administered or simultaneously administered.

The methods described herein can be used for any one or more of the following purposes: alleviating one or more symptoms of NSCLC, delaying progression of NSCLC, shrinking tumor size in NSCLC patient, inhibiting NSCLC tumor growth, prolonging overall survival, prolonging progression free survival, preventing or delaying NSCLC tumor metastasis, reducing (such as eradiating) preexisting NSCLC tumor metastasis, reducing incidence or burden of preexisting NSCLC tumor metastasis, or preventing recurrence of NSCLC.

Thus, for example, the invention provides methods of treating NSCLC in an individual, comprising administering to the individual (a) an effective amount of a composition comprising nanoparticles comprising paclitaxel and albumin; and (b) an effective amount of carboplatin, wherein the dose of paclitaxel in the composition comprising nanoparticles comprising paclitaxel and albumin is 100 mg/m$^2$ administered weekly and the dose of carboplatin is AUC=6 administered once every three weeks, wherein the individual is diabetic. In some embodiments, the invention provided methods of treating NSCLC in an individual, comprising administering to the individual (a) an effective amount of a composition comprising nanoparticles comprising paclitaxel and albumin; and (b) an effective amount of carboplatin, wherein the dose of paclitaxel in the composition comprising nanoparticles comprising paclitaxel and albumin is 100 mg/m2 administered weekly and the dose of carboplatin is AUC=6 administered once every three weeks, wherein the individual has four or more metastatic sites. In some embodiments, there are provided methods of treating NSCLC in an individual, comprising administering to the individual (a) an effective amount of a composition comprising nanoparticles comprising paclitaxel and albumin; and (b) an effective amount of carboplatin, wherein the dose of paclitaxel in the composition comprising nanoparticles comprising paclitaxel and albumin is 100 mg/m2 administered weekly and the dose of carboplatin is AUC=6 administered once every three weeks, wherein the individual is at least about 70 years old.

The invention therefore also provides methods of treating advanced NSCLC in an individual, comprising administering to the individual (a) an effective amount of a composition comprising nanoparticles comprising paclitaxel and albumin; and (b) an effective amount of carboplatin, wherein the dose of paclitaxel in the composition comprising nanoparticles comprising paclitaxel and albumin is 100 mg/m$^2$ administered weekly and the dose of carboplatin is AUC=6 administered once every three weeks as first-line therapy, wherein the individual has diabetes. In some embodiments, there are provided methods of treating advanced NSCLC in an individual, comprising administering to the individual (a) an effective amount of a composition comprising nanoparticles comprising paclitaxel and albumin; and (b) an effective amount of carboplatin, wherein the dose of paclitaxel in the composition comprising nanoparticles comprising paclitaxel and albumin is 100 mg/m2 administered weekly and the dose of carboplatin is AUC=6 administered once every three weeks as first-line therapy, wherein the individual has four or more metastatic sites. In some embodiments, there are provided methods of treating advanced NSCLC in an individual, comprising administering to the individual (a) an effective amount of a composition comprising nanoparticles comprising paclitaxel and albumin; and (b) an effective amount of carboplatin, wherein the dose of paclitaxel in the composition comprising nanoparticles comprising paclitaxel and albumin is 100 mg/m2 administered weekly and the dose of carboplatin is AUC=6 administered once every three weeks as first-line therapy, wherein the individual is at least about 70 years old.

Thus also provided are methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, and wherein the individual is diabetic. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual has four or more metastatic sites. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual is at least about 70 years old.

In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual is diabetic and at least about 70 years old. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual has four or more metastatic sites and is at least about 70 years old. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual is diabetic, has four or more metastatic sites, and is at least about 70 years old.

In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the individual to be treated is ineligible for VEGF-directed therapy, for example, ineligible for treatment with bevacizumab, wherein the individual is diabetic, has four or more metastatic sites, and/or is at least 70 years old. In some embodiments, the individual is at risk of bleeding from VEGF directed therapy.

Also provided herein are methods of treating NSCLC in an individual (e.g., human) comprising administering to the individual a) an effective amount of a composition comprising nanoparticles comprising paclitaxel and an albumin; b) an effective amount of a platinum-based agent, and c) radiation (e.g. thoracic radiation), wherein the dose of paclitaxel in the composition comprising nanoparticles comprising paclitaxel and albumin is between 20 mg/m$^2$ to about 60 mg/m$^2$ (e.g., 40 mg/m$^2$) administered weekly, the dose of a platinum-based agent is between about AUC=2 to about AUC=6 (e.g., AUC=2) administered weekly, and the thoracic radiation is between about 25 Gy to about 40 Gy (e.g., about 33 Gy) fractions by either 3D conformal or intensity-modulated techniques concurrently, wherein the individual is diabetic, has four or more metastatic sites, and/or is at least 70 years old. In some embodiments, the method of treating NSCLC in an individual (e.g., human) comprising administering to the individual a) an effective amount of a composition comprising nanoparticles comprising paclitaxel and an albumin; b) an effective amount of a platinum-based agent, and c) radiation (e.g. thoracic radiation), wherein the dose of paclitaxel in the composition comprising nanoparticles comprising paclitaxel and albumin is between 20 mg/m$^2$ to about 60 mg/m$^2$ (e.g., 40 mg/m$^2$) administered weekly, the dose of a platinum-based agent is between about AUC=2 to about AUC=6 (e.g., AUC=2) administered weekly, and the thoracic radiation is between about 25 Gy to about 40 Gy (e.g., about 33 Gy) fractions by either 3D conformal or intensity-modulated techniques concurrently further comprises a consolidation therapy, wherein the consolidation therapy comprises administering to the individual a) an effective amount of a composition comprising nanoparticles comprising paclitaxel and an albumin and b) an effective amount of a platinum-based agent, wherein the dose of paclitaxel in the composition comprising nanoparticles comprising paclitaxel and albumin is between about 50 mg/m$^2$ to about 125 mg/m$^2$ (e.g., 50 mg/m$^2$, 75 mg/m$^2$, or 100 mg/m$^2$) administered weekly and the dose of carboplatin is between about AUC=2 to about AUC=6 (e.g., AUC=3, AUC=4.5, or AUC=6) administered once every three weeks, wherein the individual is diabetic, has four or more metastatic sites, and/or is at least 70 years old. In some embodiments NSCLC is inoperable Stage IIIA and/or IIIB NSCLC. In some embodiments, the NSCLC is inoperable Stage IIIA and/or IIIB NSCLC, PS 0-1, and FEV 1 >800 ml. In some embodiments, the platinum based agent is carboplatin. In some embodiments, the NSCLC is squamous cell carcinoma.

Also provided are methods of treating NSCLC in an individual comprising administering to the individual a) an effective amount of a composition comprising nanoparticles comprising paclitaxel and an albumin and b) an effective amount of a platinum-based agent, wherein the treatment is based upon the individual having one or more of characteristics selected from the group consisting of (i) has diabetes, (ii) has four or more metastatic sites, and (iii) is at least about 70 years old. In some embodiments, the treatment is further based upon the NSCLC having one or more characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

Further provided herein are methods of treating NSCLC in an individual provided that the individual has been found to (i) has diabetes, (ii) has four or more metastatic sites, and/or (iii) is at least about 70 years old, the treatment comprising administering to the individual i) an effective amount of a composition comprising nanoparticles comprising paclitaxel and an albumin and ii) an effective amount of a platinum-based agent. In some embodiments, the NSCLC has further been found to have one or more characteristics selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (1) differential albumin uptake.

Provided herein are also methods of treating NSCLC, comprising: (a) selecting (e.g., identifying) an individual having NSCLC, wherein the individual (i) has diabetes, (ii) has four or more metastatic sites, and/or (iii) is at least about 70 years old; and (b) administering to the individual thus selected i) an effective amount of a composition comprising nanoparticles comprising paclitaxel and an albumin and ii) an effective amount of a platinum-based agent. In some embodiments, the NSCLC further has one or more characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

Methods are also provided herein of assessing whether an individual with NSCLC will respond to treatment comprising assessing one or more characteristics of individual selected from the group consisting of (i) has diabetes; (ii) has four or more metastatic sites; and (iii) is at least 70 years old, wherein one or more of the characteristics of the individual indicates the individual will be responsive to the treatment and the treatment comprises i) an effective amount of a composition comprising nanoparticles comprising paclitaxel and an albumin and ii) an effective amount of a platinum-based agent. In some embodiments, the method further comprises assessing one or more characteristics of the NSCLC selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (1) differential albumin uptake. In some embodiments, the method further comprises administering to the individual a) an effective amount of a composition comprising nanoparticles comprising paclitaxel and an albumin and b) an effective amount of the platinum-based agent.

The methods further comprise identifying an individual with NSCLC likely to respond to treatment comprising a) a composition comprising nanoparticles comprising paclitaxel and an albumin and b) a platinum-based agent, comprising: (A) assessing one or more characteristics of individual selected from the group consisting of (i) has diabetes; (ii) has four or more metastatic sites; and (iii) is at least 70 years old; and (B) identifying the individual as likely to respond to treatment based on the individual having one or more of such characteristics. In some embodiments, the method further comprises assessing one or more characteristics of NSCLC selected from the group consisting of (i) squamous cellular carcinoma, (ii) differential levels of caveolin-1

(CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (B) identifying the individual having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake. In some embodiments, the method further comprises administering to the individual a) an effective amount of a composition comprising nanoparticles comprising paclitaxel and an albumin and b) an effective amount of the platinum-based agent.

In some embodiments, there is provided a method of selecting a treatment option for treating NSCLC for an individual, the treatment option comprising a) a composition comprising nanoparticles comprising paclitaxel and an albumin and b) a platinum-based agent, the method comprising: (A) assessing one or more characteristics of individual selected from the group consisting of (i) has diabetes; (ii) has four or more metastatic sites; and (iii) is at least 70 years old; and (B) selecting the treatment option based on the individual having one or more of such characteristics. In some embodiments, the method further comprises assessing one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (B) identifying the individual having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake. In some embodiments, the method further comprises administering to the individual a) an effective amount of a composition comprising nanoparticles comprising paclitaxel and an albumin and b) an effective amount of the platinum-based agent.

Provided herein are also methods for marketing a combination therapy comprising a) a composition comprising nanoparticles comprising paclitaxel and an albumin and b) a platinum-based agent for use in a NSCLC individual subpopulation, the methods comprising informing a target audience about the use of the combination therapy for treating the individual subpopulation characterized by the individuals of such subpopulation having one or more characteristics of (i) has diabetes, (ii) has four or more metastatic sites, and (iii) is at least 70 years old. In some embodiments, the individual subpopulation is further characterized by the individual having NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

In some embodiments of any of the methods, differential levels of tumor acidity are evident by differential levels of carbonic anhydrase-9 (CA-9) and/or differential levels of LDH (e.g., LDH-5). In some embodiments of any of the methods, differential levels of hyopoxia markers are evident by differential levels of HIF-1α, differential levels of HIF-2α, and/or differential levels of differentiated embryo-chrondrocyte expressed gene 1 (DEC-1).

In some embodiments of any of the methods above, the methods result in a measurable reduction in tumor size or evidence of disease or disease progression, complete response, partial response, stable disease, increase or elongation of progression free survival, increase or elongation of overall survival, or reduction in toxicity.

In some embodiments of any of the methods above, differential levels are over expression (high expression) or under expression (low expression) as compared to the expression level of a normal or control cell, a given patient population, or with an internal control. In some embodiments, levels are compared between the individual and a normal patient population, between an individual and a NSCLC patient population with a different NSCLC histology, or between an individual and a NSCLC patient population with the same NSCLC histology.

In some embodiments, differential levels is determined in tumor tissue, normal tissue adjacent to said tumor, normal tissue distal to said tumor or peripheral blood lymphocytes.

In some embodiments of any of the methods described herein, the NSCLC is squamous cell carcinoma (i.e., epidermoid carcinoma), large cell carcinoma, adenocarcinoma, adenosquamous carcinoma, carcinomas with pleomorphic, sarcomatoid, or sarcomatous elements, carcinoid tumor, or salivary gland carcinoma. In some embodiments, the NSCLC is squamous cell carcinoma. In some embodiments of any of the methods described herein, the NSCLC is an occult tumor, a stage 0 tumor, a stage I tumor, a stage II tumor, a stage IIIA tumor, a stage IIIB tumor, or a stage IV tumor. In some embodiments of any of the methods described herein, the NSCLC is early stage NSCLC, non-metastatic NSCLC, primary NSCLC, advanced NSCLC, locally advanced NSCLC, metastatic NSCLC, NSCLC in remission, or recurrent NSCLC. In some embodiments, the NSCLC is localized resectable, localized unresectable, or unresectable. In some embodiments, the NSCLC is inoperable Stage IIIA and/or IIIB NSCLC, PS 0-1, and FEV 1>800 ml. In some embodiments of any of the methods described herein, the method is for treating NSCLC as first-line therapy or second-line therapy.

In some embodiments, the dose of paclitaxel in the composition comprising nanoparticles comprising paclitaxel and the albumin is between about 50 mg/m² to about 125 mg/m² (e.g., 50 mg/m², 75 mg/m², or 100 mg/m²) and the effective amount of the platinum-based agent is between about AUC=2 to about AUC=6 (e.g., AUC=3, AUC=4.5, or AUC=6). In some embodiments, the effective amount of the composition comprising nanoparticles comprising paclitaxel and the albumin is administered weekly and the effective amount of the platinum-based agent is administered every three weeks. In some embodiments, the dose of paclitaxel in the composition comprising nanoparticles comprising paclitaxel and the albumin is between about 50 mg/m² to about 125 mg/m² administered weekly and the effective amount of the platinum-based agent is between about AUC=2 to about AUC=6 administered once every three weeks. In some embodiments, the dose of paclitaxel in the composition comprising nanoparticles comprising paclitaxel and the albumin is about 100 mg/m² administered weekly and the effective amount of the platinum-based agent is about AUC=6 administered once every three weeks. In some embodiments, the dose of paclitaxel in the composition comprising nanoparticles comprising paclitaxel and the albumin is about 75 mg/m² administered weekly and the effective amount of the platinum-based agent is about AUC=4.5 administered once every three weeks. In some embodiments, the dose of paclitaxel in the composition comprising nanoparticles comprising paclitaxel and the albumin is about 50 mg/m² administered weekly and the effective amount of the platinum-based agent is about AUC=3 administered once every three weeks. In some embodiments, the paclitaxel nanoparticle composition and/or the platinum-based agent is administered intravenously. In some embodiments, the paclitaxel nanoparticle composition and the platinum-based agent are administered intravenously.

In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises nanoparticles comprising paclitaxel coated with human serum albumin, wherein the nanoparticles have an average particle size of no more than about 150 nm (such as about 130 nm), wherein the weight ratio of human albumin and paclitaxel in the composition is about 9:1 or less (such as about 9:1). In some embodiments, the composition comprises the albumin stabilized nanoparticle formulation of paclitaxel (Nab-paclitaxel, sold under the trademark ABRAXANE®). In some embodiments, the composition is Nab-paclitaxel, i.e. the albumin stabilized nanoparticle formulation of paclitaxel sold under the trademark ABRAXANE®.

In some embodiments, the platinum-based agent binds covalently to DNA and cross-links strands, inhibits DNA synthesis, and/or inhibits transcript. In some embodiments, the platinum-based agent is carboplatin, cisplatin, or oxaliplatin. In some embodiments, the platinum-based agent is carboplatin. In some embodiments, the platinum-based agent is cisplatin.

In some embodiments, the composition comprising nanoparticles comprising paclitaxel and an albumin and the platinum-based agent are sequentially administered; concurrently administered or simultaneously administered.

Also provided are compositions (such as pharmaceutical compositions), medicine, kits, and unit dosages useful for methods described herein.

These and other aspects and advantages of the present invention will become apparent from the subsequent detailed description and the appended claims. It is to be understood that one, some, or all of the properties of the various embodiments described herein may be combined to form other embodiments of the present invention.

DETAILED DESCRIPTION OF THE INVENTION

The present invention provides methods of combination therapy for treating NSCLC by administering a) a composition comprising nanoparticles comprising paclitaxel and an albumin and b) a platinum-based agent (such as carboplatin).

In one aspect, there is provided a method of treating NSCLC in an individual, comprising administering to the individual (a) an effective amount of a composition comprising nanoparticles comprising paclitaxel and albumin; and (b) an effective amount of a platinum-based agent, wherein the individual has diabetes.

In another aspect, there is provided a method of treating NSCLC in an individual, comprising administering to the individual (a) an effective amount of a composition comprising nanoparticles comprising paclitaxel and albumin; and (b) an effective amount of a platinum-based agent, wherein the individual has four or more metastatic sites.

In another aspect, there is provided a method of treating NSCLC in an individual, comprising administering to the individual (a) an effective amount of a composition comprising nanoparticles comprising paclitaxel and albumin; and (b) an effective amount of a platinum-based agent, wherein the individual is at least 70 years old.

Also provided are compositions (such as pharmaceutical compositions), medicine, kits, and unit dosages useful for the methods described herein.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of NSCLC. The methods of the invention contemplate any one or more of these aspects of treatment.

The term "individual" refers to a mammal and includes, but is not limited to, human, bovine, horse, feline, canine, rodent, or primate. Preferably, the individual is a human.

As used herein, an "at risk" individual is an individual who is at risk of developing NSCLC. An individual "at risk" may or may not have detectable disease, and may or may not have displayed detectable disease prior to the treatment methods described herein. "At risk" denotes that an individual has one or more so-called risk factors, which are measurable parameters that correlate with development of NSCLC, which are described herein. An individual having one or more of these risk factors has a higher probability of developing cancer than an individual without these risk factor(s).

"Adjuvant setting" refers to a clinical setting in which an individual has had a history of NSCLC, and generally (but not necessarily) been responsive to therapy, which includes, but is not limited to, surgery (e.g., surgery resection), radiotherapy, and chemotherapy. However, because of their history of NSCLC, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of NSCLC means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of NSCLC is a method that reduces probability of disease development in a given time frame and/or reduces the extent of the disease in a given time frame, when compared to not using the method. Such comparisons are typically based on clinical studies, using a statistically significant number of subjects. NSCLC development can be detectable using standard methods, including, but not limited to, computerized axial tomography (CAT Scan), Magnetic Resonance Imaging (MRI), abdominal ultrasound, clotting tests, arteriography, or biopsy. Development may also refer to NSCLC progression that may be initially undetectable and includes occurrence, recurrence, and onset.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual. Such combinations are considered to be part of a single treatment regimen or regime.

The term "effective amount" used herein refers to an amount of a compound or composition sufficient to treat a specified disorder, condition or disease such as ameliorate, palliate, lessen, and/or delay one or more of its symptoms. In reference to NSCLC, an effective amount comprises an amount sufficient to cause a tumor to shrink and/or to decrease the growth rate of the tumor (such as to suppress tumor growth) or to prevent or delay other unwanted cell proliferation in NSCLC. In some embodiments, an effective amount is an amount sufficient to delay development of NSCLC. In some embodiments, an effective amount is an amount sufficient to prevent or delay recurrence. An effective amount can be administered in one or more administrations. In the case of NSCLC, the effective amount of the drug or composition may: (i) reduce the number of NSCLC cells; (ii) reduce tumor size; (iii) inhibit, retard, slow to some extent and preferably stop NSCLC cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with NSCLC.

The term "simultaneous administration," as used herein, means that a first therapy and second therapy in a combination therapy are administered with a time separation of no more than about 15 minutes, such as no more than about any of 10 minutes, 5 minutes, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20 minutes, 30 minutes, 40 minutes, 50 minutes, 60 minutes, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

An "adverse event" or "AE" as used herein refers to any untoward medical occurrence in a patient receiving a marketed pharmaceutical product or in a patient who is participating on a clinical trial who is receiving an investigational or non-investigational pharmaceutical agent. The AE does not necessarily have a causal relationship with the patient's treatment. Therefore, an AE can be any unfavorable and unintended sign, symptom, or disease temporally associated with the use of a medicinal product, whether or not considered to be related to the medicinal product. Many AEs may be related to progression of the patient's underlying malignancy. An AE includes, but is not limited to: an exacerbation of a pre-existing illness; an increase in frequency or intensity of a pre-existing episodic event or condition; a condition detected or diagnosed after study drug administration even though it may have been present prior to the start of the study; and continuously persistent disease or symptoms that were present at baseline and worsen following the start of the study. An AE generally does not include: medical or surgical procedures (e.g., surgery, endoscopy, tooth extraction, or transfusion); however, the condition that leads to the procedure is an adverse event; pre-existing diseases, conditions, or laboratory abnormalities present or detected at the start of the study that do not worsen; hospitalizations or procedures that are done for elective purposes not related to an untoward medical occurrence (e.g., hospitalizations for cosmetic or elective surgery or social/convenience admissions); the disease being studied or signs/symptoms associated with the disease unless more severe than expected for the patient's condition; and overdose of study drug without any clinical signs or symptoms.

A "serious adverse event" or (SAE) as used herein refers to any untoward medical occurrence at any dose including, but not limited to, that: a) is fatal; b) is life-threatening (defined as an immediate risk of death from the event as it occurred); c) results in persistent or significant disability or incapacity; d) requires in-patient hospitalization or prolongs an existing hospitalization (exception: Hospitalization for elective treatment of a pre-existing condition that did not worsen during the study is not considered an adverse event. Complications that occur during hospitalization are AEs and if a complication prolongs hospitalization, then the event is serious); e) is a congenital anomaly/birth defect in the offspring of a patient who received medication; or f) conditions not included in the above definitions that may jeopardize the patient or may require intervention to prevent one of the outcomes listed above unless clearly related to the patient's underlying disease. "Lack of efficacy" (progressive disease) is not considered an AE. The signs and symptoms or clinical sequelae resulting from lack of efficacy should be reported if they fulfill the AE or SAE definitions.

The following definitions may be used to evaluate response based on target lesions: "complete response" or "CR" refers to disappearance of all target lesions; "partial response" or "PR" refers to at least a 30% decrease in the sum of the longest diameters (SLD) of target lesions, taking as reference the baseline SLD; "stable disease" or "SD" refers to neither sufficient shrinkage of target lesions to qualify for PR, nor sufficient increase to qualify for PD, taking as reference the nadir SLD since the treatment started; "progressive disease" or "PD" refers to at least a 20% increase in the SLD of target lesions, taking as reference the nadir SLD recorded since the treatment started, or, the presence of one or more new lesions; "unable to evaluate" or "UE" refers to a target lesion present at baseline which was not measured or which was unable to be evaluated leading to an inability to determine the status of that particular tumor for the time point in question (if the SLD cannot be determined at a time point, and the rules for PD do not apply, a response of CR, PR or SD cannot be assigned for that time point and the time point response will be UE); "not applicable" or "NA" refers to no target lesions were identified at baseline (patients with no target lesions identified at baseline cannot be assessed for response. These patients will be assessed for progression only); and "not done" or "ND" refers to scans were not performed at this time point to evaluate the target lesions.

The following definitions of response assessments may be used to evaluate a non-target lesion: "complete response" or "CR" refers to disappearance of all non-target lesions; "stable disease" or "SD" refers to the persistence of one or more non-target lesions not qualifying for CR or PD; "progressive disease" or "PD" refers to the "unequivocal progression" of existing non-target lesion(s) or appearance of one or more new lesion(s) is considered progressive disease (if PD for the subject is to be assessed for a time point based solely on the progression of non-target lesion(s), then additional criteria are required to be fulfilled. In this instance, the lesion(s) upon which the assessment of PD is being made must be retrospectively assessed from baseline (or the nadir) and compared to the time point in question. PD of non-target lesion(s) in this instance may be assessed when the SLD of the lesion(s) has increased by 20% or greater and the lesion(s) measure greater than or equal to 10 mm in longest dimension (LD) at the time of progression. If the nontarget lesion(s) do not meet the quantitative criteria as described, they will not be assessed as having progressed. For pleural fluid, ascites, pericardial effusions and other fluid collections, progression will be assessed in an otherwise stable or responding subject when the increase in the fluid is estimated to be greater than 500 cc., and is not attributable to a benign cause identified radiographically.); "unable to evaluate" or "UE" refers to any non-target lesion present at baseline which was not measured or was unable to be evaluated leading to an inability to determine the status of that particular tumor for the time point in question; "not applicable" or "NA" refers to no non-target lesions were identified at baseline; and "not done" or "ND" refers to scans were not performed at this time point to evaluate the non-target lesions.

As used herein, "at the time of starting treatment" or "baseline" refers to the time period at or prior to the first exposure to a treatment comprising a) a composition comprising nanoparticles comprising paclitaxel and an albumin; and b) a platinum-based agent. In some embodiments, "at the time of starting treatment" or "baseline" is about any of six months, three months, second two months, one month, or days prior to a treatment comprising a) a composition comprising nanoparticles comprising paclitaxel and an albumin; and b) a platinum-based agent. In some embodiments, "at the time of starting treatment" is immediately prior to or coincidental with the first exposure to a treatment comprising a) a composition comprising nanoparticles comprising paclitaxel and an albumin; and b) a platinum-based agent.

As used herein, "based upon" includes assessing, determining, or measuring the patient characteristics as described herein (and preferably selecting a patient suitable for receiving treatment). When an individual's characteristics "is used as a basis" for administration of the treatment methods described herein, or selection for the treatment methods described herein, the individual's characteristics is evaluated before and/or during treatment, and the conclusions obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment (s); (e) probable or likely unsuitability of an individual to continue to receive treatment(s); (f) adjusting dosage; or (g) predicting likelihood of clinical benefits.

"Likely to respond" or "responsiveness" as used herein refers to any kind of improvement or positive response either clinical or non-clinical selected from, but not limited to, measurable reduction in tumor size or evidence of disease or disease progression, complete response, partial response, stable disease, increase or elongation of progression free survival, or increase or elongation of overall survival.

"Progression free survival" (PFS) indicates the length of time during and after treatment that the cancer does not grow. Progression-free survival includes the amount of time patients have experienced a complete response or a partial response, as well as the amount of time patients have experienced stable disease.

A "complete response" (CR) to a therapy defines patients with evaluable but non-measurable disease, whose tumor and all evidence of disease had disappeared.

A "partial response" (PR) to a therapy defines patients with anything less than complete response were simply categorized as demonstrating partial response.

"Stable disease" (SD) indicates that the patient is stable.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

As is apparent to one skilled in the art, an individual assessed, selected for, and/or receiving treatment is an individual in need of such activities.

Methods of Treating NSCLC

The present invention provides methods of treating NSCLC in an individual (e.g., human) comprising administering to the individual a) an effective amount of a composition comprising nanoparticles comprising paclitaxel and an albumin; and b) an effective amount of a platinum-based agent, wherein the individual (i) has diabetes, (ii) has four or more metastatic sites, and/or (iii) is at least about 70 years old. In some embodiments, there is provided treating NSCLC in an individual, comprising administering to the individual (a) an effective amount of a composition comprising nanoparticles comprising paclitaxel and albumin; and (b) an effective amount of platinum-based agent, wherein the individual has diabetes. In some embodiments, there is provided treating NSCLC in an individual, comprising administering to the individual (a) an effective amount of a composition comprising nanoparticles comprising paclitaxel and albumin; and (b) an effective amount of platinum-based agent, wherein the individual has four or more metastatic sites. In some embodiments, there is provided treating NSCLC in an individual, comprising administering to the individual (a) an effective amount of a composition comprising nanoparticles comprising paclitaxel and albumin; and (b) an effective amount of platinum-based agent, wherein the individual is at least about 70 years old. In some embodiments, there is provided treating NSCLC in an individual, comprising administering to the individual (a) an effective amount of a composition comprising nanoparticles comprising paclitaxel and albumin; and (b) an effective amount of platinum-based agent, wherein the individual has diabetes and is at least about 70 years old. In some embodiments, there is provided treating NSCLC in an individual, comprising administering to the individual (a) an effective amount of a composition comprising nanoparticles comprising paclitaxel and albumin; and (b) an effective amount of platinum-based agent, wherein the individual has diabetes and has four or more metastatic sites. In some embodiments, there is provided treating NSCLC in an individual, comprising administering to the individual (a) an effective amount of a composition comprising nanoparticles comprising paclitaxel and albumin; and (b) an effective amount of platinum-based agent, wherein the individual has diabetes, has four or more metastatic sites, and is at least about 70 years old. In some embodiments according to any of the above methods, the NSCLC is squamous cell carcinoma.

The methods herein are applicable to multiple histological types of NSCLC. The NSCLC may be squamous cell carcinoma (i.e., epidermoid carcinoma), large cell carcinoma, adenocarcinoma, adenosquamous carcinoma, carcinomas with pleomorphic, sarcomatoid, or sarcomatous elements, carcinoid tumor, or salivary gland carcinoma. In some embodiments the NSCLC is squamous cell carcinoma. In some embodiments, the squamous cell carcinoma is papillary, clear cell, small cell, or basaloid. In some embodiments, the NSCLC is adenocarcinoma. In some embodiments, the adenocarcinoma is acinar, papillary, bronchioloalveolar carcinoma (e.g., nonmucinous, mucinous, mixed mucinous and nonmucinous or indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, or clear cell adenocarcinoma. In some embodiments, the large cell carcinoma is large-cell neuroendocrine carcinoma, combined large-cell neuroendocrine carcinoma, basaloid carcinoma, lymphoepithelioma-like carcinoma, clear cell carcinoma, or large cell carcinoma with rhabdoid phenotype. In some embodiments, the carcinoma with pleomorphic, sarcomatoid, or sarcomatous elements is carcinomas with spindle and/or giant cells, spindle cell carcinoma, giant cell carcinoma, carcinosarcoma, or pulmonary blastoma. In some embodiments, the carcinoma of salivary-gland type is mucoepidermoid carcinoma or adenoid cystic carcinoma.

The NSCLC of any of the methods herein may be an occult tumor, a stage 0 tumor, a stage I tumor (stage IA (T1, N0, M0) or stage IB (T2, N0, M0)), a stage II tumor (stage IIA (T1, N1, M0) and stage IIB (T2, N1, M0)), a stage IIIA tumor (T1, N2, M0, T2, N2, M0, T3, N1, M0, or T3, N2, M0), a stage IIIB tumor (Any T, N3, M0 or T4, any N, M0), or a stage IV tumor (Any T, any N, M1). In some embodiments of any of the methods described herein, the NSCLC is early stage NSCLC, non-metastatic NSCLC, primary NSCLC, advanced NSCLC, locally advanced NSCLC, metastatic NSCLC, NSCLC in remission, or recurrent NSCLC. In some embodiments, the NSCLC is localized resectable, localized unresectable, or unresectable. In some embodiments, the NSCLC is unresectable stage IV NSCLC. In some embodiments, the NSCLC is inoperable Stage IIIA and/or IIIB NSCLC, PS 0-1, and FEV 1>800 ml.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second line therapy.

In some embodiments of any of the methods described herein, the composition comprises nanoparticles comprising paclitaxel and an albumin (such as human serum albumin), wherein paclitaxel in the nanoparticles is coated with the albumin. In some embodiments, the average particle size of the nanoparticles in the composition is no greater than about 200 nm (such as less than about 200 nm). In some embodiments, the composition comprises Nab-paclitaxel, i.e., the albumin stabilized nanoparticle formulation of paclitaxel sold under the trademark ABRAXANE®. In some embodiments, the composition is the Nab-paclitaxel, i.e., the albumin stabilized nanoparticle formulation of paclitaxel sold under the trademark ABRAXANE®. In some embodiments, the nanoparticle composition and the platinum-based agent have synergistic effect on treating NSCLC.

Platinum-based agent binds covalently to DNA and cross-links strands, inhibits DNA synthesis, and/or inhibits transcript. In some embodiments, the platinum-based agent is carboplatin, cisplatin, or oxaliplatin. In some embodiments, the platinum-based agent is carboplatin. In some embodiments, the platinum-based agent is cisplatin.

In some embodiments, the dose of paclitaxel in composition comprising nanoparticles comprising paclitaxel and the albumin is between about 50 mg/m$^2$ to about 125 mg/m$^2$ (e.g., 50 mg/m$^2$, 75 mg/m$^2$, or 100 mg/m$^2$) and the effective amount of the platinum-based agent is between about AUC=2 to about AUC=6 (e.g., AUC=3, AUC=4.5, or AUC=6). In some embodiments, the effective amount of the composition comprising nanoparticles comprising paclitaxel and the albumin is administered weekly and the effective amount of the platinum-based agent is administered every three weeks. In some embodiments, the dose of paclitaxel in the composition comprising nanoparticles comprising paclitaxel and the albumin is between about 50 mg/m$^2$ to about 125 mg/m$^2$ administered weekly and the effective amount of the platinum-based agent is between about AUC=2 to about AUC=6 administered once every three weeks. In some embodiments, the dose of paclitaxel in the composition comprising nanoparticles comprising paclitaxel and the albumin is about 100 mg/m$^2$ administered weekly and the effective amount of the platinum-based agent is about AUC=6 administered once every three weeks. In some embodiments, the dose of paclitaxel in the composition comprising nanoparticles comprising paclitaxel and the albumin is about 75 mg/m$^2$ administered weekly and the effective amount of the platinum-based agent is about AUC=4.5 administered once every three weeks. In some embodiments, the dose of paclitaxel in the composition comprising nanoparticles comprising paclitaxel and the albumin is about 50 mg/m$^2$ administered weekly and the effective amount of the platinum-based agent is about AUC=3 administered once every three weeks. In some embodiments, the dose of paclitaxel in the composition comprising nanoparticles comprising paclitaxel and the albumin is about 40 mg/m$^2$ administered weekly and the effective amount of the platinum-based agent is about AUC=2 administered weekly. In some embodiments, the paclitaxel nanoparticle composition and/or the platinum-based agent is administered intravenously. In some embodiments, the paclitaxel nanoparticle composition and the platinum-based agent are administered intravenously.

In some embodiments, the composition comprising nanoparticles comprising paclitaxel and the albumin and the platinum-based agent are sequentially administered; concurrently administered or simultaneously administered.

In some embodiments, the composition comprising nanoparticles comprising paclitaxel and albumin is administered without any steroid premedication and/or without G-CSF prophylaxis.

For example, methods are provided for treating NSCLC in an individual, comprising administering to the individual (a) an effective amount of a composition comprising nanoparticles comprising paclitaxel and albumin; and (b) an effective amount of platinum-based agent, wherein the dose of paclitaxel in the composition comprising nanoparticles comprising paclitaxel and albumin is 100 mg/m$^2$ administered weekly and the dose of the platinum-based agent is AUC=6, wherein the individual has diabetes. In some embodiments, methods are provided for treating NSCLC in an individual, comprising administering to the individual (a) an effective amount of a composition comprising nanoparticles comprising paclitaxel and albumin; and (b) an effective amount of platinum-based agent, wherein the dose of paclitaxel in the composition comprising nanoparticles comprising paclitaxel and albumin is 100 mg/m2 administered weekly and the dose of the platinum-based agent is AUC=6, wherein the individual has four or more metastatic sites. In some embodiments, methods are provided for treating NSCLC in an individual, comprising administering to the individual (a) an effective amount of a composition comprising nanoparticles comprising paclitaxel and albumin; and (b) an effective amount of platinum-based agent, wherein the dose of paclitaxel in composition comprising nanoparticles comprising paclitaxel and albumin is 100 mg/m2 administered weekly and the dose of the platinum-based agent is AUC=6, wherein the individual is at least about 70 years old. In some embodiments, methods are provided for treating NSCLC in an individual, comprising administering to the individual (a) an effective amount of a composition comprising nanoparticles comprising paclitaxel and albumin; and (b) an effective amount of platinum-based agent, wherein the dose of paclitaxel in the composition comprising nanoparticles comprising paclitaxel and albumin is 100 mg/m2 administered weekly and the dose of the platinum-based agent is AUC=6, wherein the individual has diabetes and has four or more metastatic sites. In some embodiments, methods are provided for treating NSCLC in an individual, comprising administering to the individual (a) an effective amount of a composition comprising nanoparticles comprising paclitaxel and albumin; and (b) an effective amount of platinum-based agent, wherein the dose of paclitaxel in the composition comprising nanoparticles comprising paclitaxel and albumin is 100 mg/m2 administered weekly and the dose of the platinum-based agent is AUC=6, wherein the individual has diabetes and is at least about 70 years old. In some embodiments, methods are provided for treating NSCLC in an individual, comprising administering to the individual (a) an effective amount of a composition comprising nanoparticles comprising paclitaxel and albumin; and (b) an effective amount of platinum-based agent, wherein the dose of paclitaxel in the composition comprising nanoparticles comprising paclitaxel and albumin is 100 mg/m2 administered weekly and the dose of the platinum-based agent is AUC=6, wherein the individual has diabetes, has four or more metastatic sites, and is at least about 70 years old. In some embodiments, the composition comprising nanoparticles comprising paclitaxel and albumin is administered weekly and the platinum-based agent is administered once every three weeks. In some embodiments, the composition comprising nanoparticles comprising paclitaxel and albumin and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods for treating NSCLC in an individual, comprising administering to the individual (a) an effective amount of a composition comprising nanoparticles comprising paclitaxel coated with albumin; and (b) an effective amount of platinum-based agent, wherein the dose of paclitaxel in the composition comprising nanoparticles comprising paclitaxel coated with albumin is 100 mg/m$^2$ administered weekly and the dose of the platinum-based agent is AUC=6, wherein the individual has diabetes. In some embodiments, there are provided methods for treating NSCLC in an individual, comprising administering to the individual (a) an effective amount of a composition comprising nanoparticles comprising paclitaxel coated with albumin; and (b) an effective amount of platinum-based agent, wherein the dose of paclitaxel in the composition comprising nanoparticles comprising paclitaxel coated with albumin is 100 mg/m² administered weekly and the dose of the platinum-based agent is AUC=6, wherein the individual has four or more metastatic sites. In some embodiments, there are provided methods for treating NSCLC in an individual, comprising administering to the individual (a) an effective amount of a composition comprising nanoparticles comprising paclitaxel coated with albumin; and (b) an effective amount of platinum-based agent, wherein the dose of paclitaxel in the composition comprising nanoparticles comprising paclitaxel coated with albumin is 100 mg/m² administered weekly and the dose of the platinum-based agent is AUC=6, wherein the individual is at least 70 years old. In some embodiments, there are provided methods for treating NSCLC in an individual, comprising administering to the individual (a) an effective amount of a composition comprising nanoparticles comprising paclitaxel coated with albumin; and (b) an effective amount of platinum-based agent, wherein the dose of paclitaxel in composition comprising nanoparticles comprising paclitaxel coated with albumin is 100 mg/m² administered weekly and the dose of the platinum-based agent is AUC=6, wherein the individual has diabetes and has four or more metastatic sites. In some embodiments, there are provided methods for treating NSCLC in an individual, comprising administering to the individual (a) an effective amount of a composition comprising nanoparticles comprising paclitaxel coated with albumin; and (b) an effective amount of platinum-based agent, wherein the dose of paclitaxel in the composition comprising nanoparticles comprising paclitaxel coated with albumin is 100 mg/m² administered weekly and the dose of the platinum-based agent is AUC=6, wherein the individual has diabetes and is at least 70 years old. In some embodiments, there are provided methods for treating NSCLC in an individual, comprising administering to the individual (a) an effective amount of a composition comprising nanoparticles comprising paclitaxel coated with albumin; and (b) an effective amount of platinum-based agent, wherein the dose of paclitaxel in the composition comprising nanoparticles comprising paclitaxel coated with albumin is 100 mg/m² administered weekly and the dose of the platinum-based agent is AUC=6, wherein the individual has diabetes, has more than four metastatic sites, and is at least 70 years old. In some embodiments, the composition comprising nanoparticles comprising paclitaxel coated with albumin is administered weekly and the platinum-based agent is administered once every three weeks. In some embodiments, the composition comprising nanoparticles comprising paclitaxel coated with albumin and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods of treating NSCLC in an individual, comprising administering to the individual (a) an effective amount of a composition comprising nanoparticles comprising paclitaxel and albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel and albumin is 100 mg/m² administered weekly and the dose of the platinum-based agent is AUC=6, wherein the individual has diabetes. In some embodiments, there are provided methods of treating NSCLC in an individual, comprising administering to the individual (a) an effective amount of a composition comprising nanoparticles comprising paclitaxel and albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel and albumin is 100 mg/m² administered weekly and the dose of the platinum-based agent is AUC=6, wherein the individual has four or more metastatic sites. In some embodiments, there are provided methods of treating NSCLC in an individual, comprising administering to the individual (a) an effective amount of a composition comprising nanoparticles comprising paclitaxel and albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel and albumin is 100 mg/m² administered weekly and the dose of the platinum-based agent is AUC=6, wherein the individual is at least about 70 years old. In some embodiments, there are provided methods of treating NSCLC in an individual, comprising administering to the individual (a) an effective amount of a composition comprising nanoparticles comprising paclitaxel and albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel and albumin is 100 mg/m² administered weekly and the dose of the platinum-based agent is AUC=6, wherein the individual has diabetes and has four or more metastatic sites. In some embodiments, there are provided methods of treating NSCLC in an individual, comprising administering to the individual (a) an effective amount of a composition comprising nanoparticles comprising paclitaxel and albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel and albumin is 100 mg/m² administered weekly and the dose of the platinum-based agent is AUC=6, wherein the individual has diabetes and is at least about 70 years old. In some embodiments, there are provided methods of treating NSCLC in an individual, comprising administering to the individual (a) an effective amount of a composition comprising nanoparticles comprising paclitaxel and albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel and albumin is 100 mg/m² administered weekly and the dose of the platinum-based agent is AUC=6, wherein the individual has diabetes, has four or more metastatic sites, and is at least about 70 years old. In some embodiments, the composition comprising nanoparticles comprising paclitaxel and albumin is administered weekly and the platinum-based agent is administered once every three weeks. In some embodiments, the composition comprising nanoparticles comprising paclitaxel and albumin and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods for treating NSCLC in an individual, comprising administering to the individual (a) an effective amount of a composition comprising nanoparticles comprising paclitaxel coated with albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel coated with albumin is 100 mg/m$^2$ administered weekly and the dose of the platinum-based agent is AUC=6, wherein the individual has diabetes. In some embodiments, there are provided methods for treating NSCLC in an individual, comprising administering to the individual (a) an effective amount of a composition comprising nanoparticles comprising paclitaxel coated with albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel coated with albumin is 100 mg/m$^2$ administered weekly and the dose of the platinum-based agent is AUC=6, wherein the individual has four or more metastatic sites. In some embodiments, there are provided methods for treating NSCLC in an individual, comprising administering to the individual (a) an effective amount of a composition comprising nanoparticles comprising paclitaxel coated with albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel coated with albumin is 100 mg/m$^2$ administered weekly and the dose of the platinum-based agent is AUC=6, wherein the individual is at least about 70 years old. In some embodiments, there are provided methods for treating NSCLC in an individual, comprising administering to the individual (a) an effective amount of a composition comprising nanoparticles comprising paclitaxel coated with albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel coated with albumin is 100 mg/m$^2$ administered weekly and the dose of the platinum-based agent is AUC=6, wherein the individual has diabetes and has four or more metastatic sites. In some embodiments, there are provided methods for treating NSCLC in an individual, comprising administering to the individual (a) an effective amount of a composition comprising nanoparticles comprising paclitaxel coated with albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel coated with albumin is 100 mg/m$^2$ administered weekly and the dose of the platinum-based agent is AUC=6, wherein the individual has diabetes and is at least about 70 years old. In some embodiments, there are provided methods for treating NSCLC in an individual, comprising administering to the individual (a) an effective amount of a composition comprising nanoparticles comprising paclitaxel coated with albumin, wherein the average size of the nanoparticles in the nanoparticle composition is no greater than about 200 nm; and (b) an effective amount of platinum-based agent, wherein the dose of paclitaxel in the composition comprising nanoparticles comprising paclitaxel coated with albumin is 100 mg/m$^2$ administered weekly and the dose of the platinum-based agent is AUC=6, wherein the individual has diabetes, has four or more metastatic sites, and is at least about 70 years old. In some embodiments, the composition comprising nanoparticles comprising paclitaxel coated with albumin is administered weekly and the platinum-based agent is administered once every three weeks. In some embodiments, the composition comprising nanoparticles comprising paclitaxel coated with albumin and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of platinum-based agent, wherein the dose of the Nab-paclitaxel, i.e., the albumin stabilized nanoparticle formulation of paclitaxel sold under the trademark ABRAXANE® is 100 mg/m$^2$ administered weekly and the dose of the platinum-based agent is AUC=6, wherein the individual has diabetes. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of platinum-based agent, wherein the dose of the Nab-paclitaxel, i.e., the albumin stabilized nanoparticle formulation of paclitaxel sold under the trademark ABRAXANE® is 100 mg/m$^2$ administered weekly and the dose of the platinum-based agent is AUC=6, wherein the individual has four or more metastatic sites. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of platinum-based agent, wherein the dose of the Nab-paclitaxel, i.e., the albumin stabilized nanoparticle formulation of paclitaxel sold under the trademark ABRAXANE® is 100 mg/m$^2$ administered weekly and the dose of the platinum-based agent is AUC=6, wherein the individual is at least about 70 years old. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of platinum-based agent, wherein the dose of the Nab-paclitaxel, i.e., the albumin stabilized nanoparticle formulation of paclitaxel sold under the trademark ABRAXANE® is 100 mg/m$^2$ administered weekly and the dose of the platinum-based agent is AUC=6, wherein the individual has diabetes and has four or more metastatic sites. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of platinum-based agent, wherein the dose of the Nab-paclitaxel, i.e., the albumin stabilized nanoparticle formulation of paclitaxel sold under the trademark ABRAXANE® is 100 mg/m$^2$ administered weekly and the dose of the platinum-based agent is AUC=6, wherein the individual has diabetes and is at least about 70 years old. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of platinum-based agent, wherein the dose of the Nab-paclitaxel, i.e., the albumin stabilized nanoparticle formulation of paclitaxel sold under the trademark ABRAXANE® is 100 mg/m$^2$ administered weekly and the dose of the platinum-based agent is AUC=6, wherein the individual has diabetes, has four or more metastatic sites, and is at least about 70 years old. In some embodiments, the Nab-paclitaxel, i.e. the albumin stabilized nanoparticle formulation of paclitaxel sold under the trademark ABRAXANE® is administered weekly and the platinum-based agent is administered once every three weeks. In some embodiments, Nab-paclitaxel, i.e., the albumin stabilized nanoparticle formulation of paclitaxel sold under the trademark ABRAXANE® and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of carboplatin, wherein the dose of the Nab-paclitaxel, i.e., the albumin stabilized nanoparticle formulation of paclitaxel sold under the trademark ABRAXANE® is 100 mg/m$^2$ administered weekly and the dose of carboplatin is AUC=6, wherein the individual has diabetes. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of carboplatin, wherein the dose of the Nab-paclitaxel, i.e., the albumin stabilized nanoparticle formulation of paclitaxel sold under the trademark ABRAXANE® is 100 mg/m$^2$ administered weekly and the dose of carboplatin is AUC=6, wherein the individual has four or more metastatic sites. In some embodiments, there are provided methods for treating NSCLC in an individual, comprising administering to the individual (a) an effective amount of Nab-paclitaxel, i.e. the albumin stabilized nanoparticle formulation of paclitaxel sold under the trademark ABRAXANE®; and (b) an effective amount of carboplatin, wherein the dose of the Nab-paclitaxel, i.e. the albumin stabilized nanoparticle formulation of paclitaxel sold under the trademark ABRAXANE® is 100 mg/m$^2$ administered weekly and the dose of carboplatin is AUC=6, wherein the individual is at least about 70 years old. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of carboplatin, wherein the dose of the Nab-paclitaxel, i.e., the albumin stabilized nanoparticle formulation of paclitaxel sold under the trademark ABRAXANE® is 100 mg/m$^2$ administered weekly and the dose of carboplatin is AUC=6, wherein the individual has diabetes and has four or more metastatic sites. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of carboplatin, wherein the dose of the Nab-paclitaxel, i.e., the albumin stabilized nanoparticle formulation of paclitaxel sold under the trademark ABRAXANE® is 100 mg/m$^2$ administered weekly and the dose of carboplatin is AUC=6, wherein the individual has diabetes and is at least about 70 years old. In some embodiments, there are provided methods for treating NSCLC in an individual, comprising administering to the individual (a) an effective amount of Nab-paclitaxel, i.e., the albumin stabilized nanoparticle formulation of paclitaxel sold under the trademark ABRAXANE®; and (b) an effective amount of carboplatin, wherein the dose of the Nab-paclitaxel, i.e., the albumin stabilized nanoparticle formulation of paclitaxel sold under the trademark ABRAXANE® is 100 mg/m$^2$ administered weekly and the dose of carboplatin is AUC=6, wherein the individual has diabetes, has four or more metastatic sites, and is at least about 70 years old. In some embodiments, the Nab-paclitaxel, i.e., the albumin stabilized nanoparticle formulation of paclitaxel sold under the trademark ABRAXANE® is administered weekly and the carboplatin is administered once every three weeks. In some embodiments, Nab-paclitaxel, i.e., the albumin stabilized nanoparticle formulation of paclitaxel sold under the trademark ABRAXANE® and the carboplatin are administered intravenously. In some embodiments NSCLC is advanced NSCLC. In some embodiments, the method is used as first-line therapy. In some embodiments, the NSCLC is squamous cell carcinoma.

Also provided are methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual has diabetes. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual has four or more metastatic sites. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual is at least about 70 years old. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual has diabetes and has four or more metastatic sites. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual has diabetes and is at least about 70 years old. In some embodiments, there are provided methods of treating NSCLC in an individual, comprising administering to the individual a) an effective amount of a composition comprising nanoparticles comprising paclitaxel and an albumin and b) an effective amount of a platinum-based agent, wherein the NSCLC is squamous cellular carcinoma, wherein the individual has diabetes, has four or more metastatic sites, and is at least about 70 years old. In some embodiments, the dose of paclitaxel in the composition comprising nanoparticles comprising paclitaxel and albumin is 100 mg/m$^2$ administered weekly and the dose of the platinum-based agent is AUC=6. In some embodiments, the composition comprising nanoparticles comprising paclitaxel and albumin is administered weekly and the platinum-based agent is administered once every three weeks. In some embodiments, the composition comprising nanoparticles comprising paclitaxel and albumin and the platinum-based agent are administered intravenously. In some embodiments NSCLC is advanced NSCLC. In some embodiments, the method is used as first-line therapy. In some embodiments, the platinum based agent is carboplatin.

In some embodiments, there are provided methods of treating NSCLC in an individual, comprising administering to the individual a) an effective amount of a composition comprising nanoparticles comprising paclitaxel coated with albumin and b) an effective amount of a platinum-based agent, wherein the NSCLC is squamous cellular carcinoma, wherein the individual has diabetes. In some embodiments, there are provided methods of treating NSCLC in an individual, comprising administering to the individual a) an effective amount of a composition comprising nanoparticles comprising paclitaxel coated with albumin and b) an effective amount of a platinum-based agent, wherein the NSCLC is squamous cellular carcinoma, wherein the individual has four or more metastatic sites. In some embodiments, there are provided methods of treating NSCLC in an individual, comprising administering to the individual a) an effective amount of a composition comprising nanoparticles comprising paclitaxel coated with albumin and b) an effective amount of a platinum-based agent, wherein the NSCLC is squamous cellular carcinoma, wherein the individual is at least about 70 years old. In some embodiments, there are provided methods of treating NSCLC in an individual, comprising administering to the individual a) an effective amount of a composition comprising nanoparticles comprising paclitaxel coated with albumin and b) an effective amount of a platinum-based agent, wherein the NSCLC is squamous cellular carcinoma, wherein the individual has diabetes and has four or more metastatic sites. In some embodiments, there are provided methods of treating NSCLC in an individual, comprising administering to the individual a) an effective amount of a composition comprising nanoparticles comprising paclitaxel coated with albumin and b) an effective amount of a platinum-based agent, wherein the NSCLC is squamous cellular carcinoma, wherein the individual has diabetes and is at least about 70 years old. In some embodiments, there are provided methods of treating NSCLC in an individual, comprising administering to the individual a) an effective amount of a composition comprising nanoparticles comprising paclitaxel coated with albumin and b) an effective amount of a platinum-based agent, wherein the NSCLC is squamous cellular carcinoma, wherein the individual has diabetes, has four or more metastatic sites, and is at least about 70 years old. In some embodiments, the dose of paclitaxel in the composition comprising nanoparticles comprising paclitaxel coated with albumin is 100 mg/m$^2$ administered weekly and the dose of the platinum-based agent is AUC=6. In some embodiments, the composition comprising nanoparticles comprising paclitaxel coated with albumin is administered weekly and the platinum-based agent is administered once every three weeks. In some embodiments, the composition comprising nanoparticles comprising paclitaxel coated with albumin and the platinum-based agent are administered intravenously. In some embodiments NSCLC is advanced NSCLC. In some embodiments, the method is used as first-line therapy. In some embodiments, the platinum based agent is carboplatin.

In some embodiments, there are provided methods of treating NSCLC in an individual, comprising administering to the individual a) an effective amount of a composition comprising nanoparticles comprising paclitaxel and an albumin, wherein the average size of the nanoparticles in the nanoparticle composition is no greater than about 200 nm, and b) an effective amount of a platinum-based agent, wherein the NSCLC is squamous cellular carcinoma, wherein the individual has diabetes. In some embodiments, there are provided methods of treating NSCLC in an individual, comprising administering to the individual a) an effective amount of a composition comprising nanoparticles comprising paclitaxel and an albumin, wherein the average size of the nanoparticles in the nanoparticle composition is no greater than about 200 nm, and b) an effective amount of a platinum-based agent, wherein the NSCLC is squamous cellular carcinoma, wherein the individual has four or more metastatic sites. In some embodiments, there are provided methods of treating NSCLC in an individual, comprising administering to the individual a) an effective amount of a composition comprising nanoparticles comprising paclitaxel and an albumin, wherein the average size of the nanoparticles in the nanoparticle composition is no greater than about 200 nm, and b) an effective amount of a platinum-based agent, wherein the NSCLC is squamous cellular carcinoma, wherein the individual is at least about 70 years old. In some embodiments, there are provided methods of treating NSCLC in an individual, comprising administering to the individual a) an effective amount of a composition comprising nanoparticles comprising paclitaxel and an albumin, wherein the average size of the nanoparticles in the nanoparticle composition is no greater than about 200 nm, and b) an effective amount of a platinum-based agent, wherein the NSCLC is squamous cellular carcinoma, wherein the individual has diabetes and has four or more metastatic sites. In some embodiments, there are provided methods of treating NSCLC in an individual, comprising administering to the individual a) an effective amount of a composition comprising nanoparticles comprising paclitaxel and an albumin, wherein the average size of the nanoparticles in the nanoparticle composition is no greater than about 200 nm, and b) an effective amount of a platinum-based agent, wherein the NSCLC is squamous cellular carcinoma, wherein the individual has diabetes and is at least about 70 years old. In some embodiments, there are provided methods of treating NSCLC in an individual, comprising administering to the individual a) an effective amount of a composition comprising nanoparticles comprising paclitaxel and an albumin, wherein the average size of the nanoparticles in the nanoparticle composition is no greater than about 200 nm, and b) an effective amount of a platinum-based agent, wherein the NSCLC is squamous cellular carcinoma, wherein the individual has diabetes, has four or more metastatic sites, and is at least about 70 years old. In some embodiments, the dose of paclitaxel in the composition comprising nanoparticles comprising paclitaxel and albumin is 100 mg/m² administered weekly and the dose of the platinum-based agent is AUC=6. In some embodiments, the composition comprising nanoparticles comprising paclitaxel and albumin is administered weekly and the platinum-based agent is administered once every three weeks. In some embodiments, the composition comprising nanoparticles comprising paclitaxel and albumin and the platinum-based agent are administered intravenously. In some embodiments NSCLC is advanced NSCLC. In some embodiments, the method is used as first-line therapy. In some embodiments, the platinum based agent is carboplatin.

In some embodiments, there are provided methods of treating NSCLC in an individual, comprising administering to the individual a) an effective amount of a composition comprising nanoparticles comprising paclitaxel coated with albumin, wherein the average size of the nanoparticles in the nanoparticle composition is no greater than about 200 nm, and b) an effective amount of a platinum-based agent, wherein the NSCLC is squamous cellular carcinoma, wherein the individual has diabetes. In some embodiments, there are provided methods of treating NSCLC in an individual, comprising administering to the individual a) an effective amount of a composition comprising nanoparticles comprising paclitaxel coated with albumin, wherein the average size of the nanoparticles in the nanoparticle composition is no greater than about 200 nm, and b) an effective amount of a platinum-based agent, wherein the NSCLC is squamous cellular carcinoma, wherein the individual has four or more metastatic sites. In some embodiments, there are provided methods of treating NSCLC in an individual, comprising administering to the individual a) an effective amount of a composition comprising nanoparticles comprising paclitaxel coated with albumin, wherein the average size of the nanoparticles in the nanoparticle composition is no greater than about 200 nm, and b) an effective amount of a platinum-based agent, wherein the NSCLC is squamous cellular carcinoma, wherein the individual is at least about 70 years old. In some embodiments, there are provided methods of treating NSCLC in an individual, comprising administering to the individual a) an effective amount of a composition comprising nanoparticles comprising paclitaxel coated with albumin, wherein the average size of the nanoparticles in the nanoparticle composition is no greater than about 200 nm, and b) an effective amount of a platinum-based agent, wherein the NSCLC is squamous cellular carcinoma, wherein the individual has diabetes and has four or more metastatic sites. In some embodiments, there are provided methods of treating NSCLC in an individual, comprising administering to the individual a) an effective amount of a composition comprising nanoparticles comprising paclitaxel coated with albumin, wherein the average size of the nanoparticles in the nanoparticle composition is no greater than about 200 nm, and b) an effective amount of a platinum-based agent, wherein the NSCLC is squamous cellular carcinoma, wherein the individual has diabetes and is at least about 70 years old. In some embodiments, there are provided methods of treating NSCLC in an individual, comprising administering to the individual a) an effective amount of a composition comprising nanoparticles comprising paclitaxel coated with albumin, wherein the average size of the nanoparticles in the nanoparticle composition is no greater than about 200 nm, and b) an effective amount of a platinum-based agent, wherein the NSCLC is squamous cellular carcinoma, wherein the individual has diabetes, has four or more metastatic sites, and is at least about 70 years old. In some embodiments, the dose of paclitaxel in the composition comprising nanoparticles comprising paclitaxel coated with albumin is 100 mg/m² administered weekly and the dose of the platinum-based agent is AUC=6. In some embodiments, the composition comprising nanoparticles comprising paclitaxel coated with albumin is administered weekly and the platinum-based agent is administered once every three weeks. In some embodiments, the composition comprising nanoparticles comprising paclitaxel coated with albumin and the platinum-based agent are administered intravenously. In some embodiments NSCLC is advanced NSCLC. In some embodiments, the method is used as first-line therapy. In some embodiments, the platinum based agent is carboplatin.

In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of a platinum-based agent, wherein the NSCLC is squamous cellular carcinoma, wherein the individual has diabetes. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of a platinum-based agent, wherein the NSCLC is squamous cellular carcinoma, wherein the individual has four or more metastatic sites. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of a platinum-based agent, wherein the NSCLC is squamous cellular carcinoma, wherein the individual is at least about 70 years old. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of a platinum-based agent, wherein the NSCLC is squamous cellular carcinoma, wherein the individual has diabetes and has four or more metastatic sites. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of a platinum-based agent, wherein the NSCLC is squamous cellular carcinoma, wherein the individual has diabetes and is at least about 70 years old. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of a platinum-based agent, wherein the NSCLC is squamous cellular carcinoma, wherein the individual has diabetes, has four or more metastatic sites, and is at least about 70 years old. In some embodiments, the effective amount of Nab-paclitaxel, i.e., the albumin stabilized nanoparticle formulation of paclitaxel sold under the trademark ABRAXANE® is 100 mg/m² administered weekly and the dose of the platinum-based agent is AUC=6. In some embodiments, the Nab-paclitaxel, i.e., the albumin stabilized nanoparticle formulation of paclitaxel sold under the trademark ABRAXANE® is administered weekly and the platinum-based agent is administered once every three weeks. In some embodiments, the Nab-paclitaxel, i.e., the albumin stabilized nanoparticle formulation of paclitaxel sold under the trademark ABRAXANE® and the platinum-based agent are administered intravenously. In some embodiments NSCLC is advanced NSCLC. In some embodiments, the method is used as first-line therapy.

In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of carboplatin, wherein the NSCLC is squamous cellular carcinoma, wherein the individual has diabetes. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of carboplatin, wherein the NSCLC is squamous cellular carcinoma, wherein the individual has four or more metastatic sites. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of carboplatin, wherein the NSCLC is squamous cellular carcinoma, wherein the individual is at least about 70 years old. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of carboplatin, wherein the NSCLC is squamous cellular carcinoma, wherein the individual has diabetes and has four or more metastatic sites. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of carboplatin, wherein the NSCLC is squamous cellular carcinoma, wherein the individual has diabetes and is at least about 70 years old. In some embodiments, there are provided methods of treating NSCLC in an individual, comprising administering to the individual a) an effective amount of Nab-paclitaxel, i.e., the albumin stabilized nanoparticle formulation of paclitaxel sold under the trademark ABRAXANE® and b) an effective amount of carboplatin, wherein the NSCLC is squamous cellular carcinoma, wherein the individual has diabetes, has four or more metastatic sites, and is at least about 70 years old. In some embodiments, the effective amount of Nab-paclitaxel, i.e., the albumin stabilized nanoparticle formulation of paclitaxel sold under the trademark ABRAXANE® is 100 mg/m$^2$ administered weekly and the dose of carboplatin is AUC=6. In some embodiments, the Nab-paclitaxel, i.e., the albumin stabilized nanoparticle formulation of paclitaxel sold under the trademark ABRAXANE® is administered weekly and the carboplatin is administered once every three weeks. In some embodiments, the Nab-paclitaxel, i.e., the albumin stabilized nanoparticle formulation of paclitaxel sold under the trademark ABRAXANE® and the carboplatin are administered intravenously. In some embodiments NSCLC is advanced NSCLC. In some embodiments, the method is used as first-line therapy.

In some embodiments of any of the methods, the methods for treating NSCLC further comprise radiation. In some embodiments, the methods further comprise thoracic radiation. For example, methods of treating NSCLC in an individual (e.g., human) may comprise administering to the individual a) an effective amount of a composition comprising nanoparticles comprising paclitaxel and an albumin (such as nanoparticles comprising paclitaxel coated with albumin, for example Nab-paclitaxel, i.e., the albumin stabilized nanoparticle formulation of paclitaxel sold under the trademark ABRAXANE®); b) an effective amount of a platinum-based agent (such as carboplatin), and c) radiation (e.g. thoracic radiation), wherein the individual has diabetes, has four or more metastatic sites, and/or is at least about 70 years old. In some embodiments, the dose of paclitaxel in the composition comprising nanoparticles comprising paclitaxel and albumin is between 20 mg/m$^2$ to about 60 mg/m$^2$ (e.g., 40 mg/m$^2$), administered weekly, the dose of the platinum-based agent is between about AUC=2 to AUC=6 (e.g., AUC=2), and the thoracic radiation is between about 25 Gy to about 40 Gy (e.g., about 33 Gy) fractions by either 3D conformal or intensity-modulated techniques. In some embodiments, the composition comprising nanoparticles comprising paclitaxel and albumin is administered weekly and the platinum-based agent is administered weekly. In some embodiments, the treatment time is seven weeks and the thoracic radiation is concurrent. In some embodiments, the composition comprising nanoparticles comprising paclitaxel and albumin and the platinum-based agent are administered intravenously. In some embodiments, the method of treating NSCLC in an individual (e.g., human) comprising administering to the individual a) an effective amount of a composition comprising nanoparticles comprising paclitaxel and an albumin (such as nanoparticles comprising paclitaxel coated with albumin, for example Nab-paclitaxel, i.e., the albumin stabilized nanoparticle formulation of paclitaxel sold under the trademark ABRAXANE®; b) an effective amount of a platinum-based agent (such as carboplatin), and c) radiation (e.g. thoracic radiation) further comprises a consolidation therapy, wherein the individual has diabetes, has four or more metastatic sites, and/or is at least about 70 years old. In some embodiments, the consolidation therapy comprises administering to the individual a) an effective amount of a composition comprising nanoparticles comprising paclitaxel and an albumin (such as nanoparticles comprising paclitaxel coated with albumin, for example Nab-paclitaxel, i.e., the albumin stabilized nanoparticle formulation of paclitaxel sold under the trademark ABRAXANE®) and b) an effective amount of a platinum-based agent (such as carboplatin), wherein the individual has diabetes, has four or more metastatic sites, and/or is at least about 70 years old. In some embodiments of the consolidation therapy, the dose of paclitaxel in the composition comprising nanoparticles comprising paclitaxel and albumin is between about 50 mg/m$^2$ to about 125 mg/m$^2$ (e.g., 50 mg/m$^2$, 75 mg/m$^2$, or 100 mg/m$^2$) administered weekly and the dose of the platinum-based agent is between about AUC=2 and about AUC=6 (e.g., AUC=3, AUC=4.5, or AUC=6). In some embodiments, the composition comprising nanoparticles comprising paclitaxel and albumin is administered weekly and the platinum-based agent is administered once every three weeks. In some embodiments, the consolidation therapy comprises two cycles. In some embodiments, the composition comprising nanoparticles comprising paclitaxel and albumin and the platinum-based agent are administered intravenously. In some embodiments NSCLC is inoperable Stage IIIA and/or IIIB NSCLC. In some embodiments, the NSCLC is inoperable Stage IIIA and/or IIIB NSCLC, PS 0-1, and FEV 1 >800 ml. In some embodiments, the platinum based agent is carboplatin.

Further provided herein are methods of treating NSCLC in an individual (e.g., human) comprising administering to the individual a) an effective amount of a composition comprising nanoparticles comprising paclitaxel and an albumin (such as nanoparticles comprising paclitaxel coated with albumin, for example Nab-paclitaxel, i.e., the albumin stabilized nanoparticle formulation of paclitaxel sold under the trademark ABRAXANE®), and b) an effective amount of radiation (e.g. thoracic radiation), wherein the individual has diabetes, has four or more metastatic sites, and/or is at least about 70 years old. In some embodiments, the dose of paclitaxel in the composition comprising nanoparticles comprising paclitaxel and albumin is between 20 mg/m$^2$ to about 60 mg/m$^2$ (e.g., 40 mg/m$^2$), administered weekly and the thoracic radiation is between about 25 Gy to about 40 Gy (e.g., about 33 Gy) fractions by either 3D conformal or intensity-modulated techniques. In some embodiments, the treatment time is seven weeks and the thoracic radiation is concurrent. In some embodiments, the composition comprising nanoparticles comprising paclitaxel and albumin and the platinum-based agent are administered intravenously. In some embodiments, the composition comprising nanoparticles comprising paclitaxel and albumin are administered intravenously. In some embodiments NSCLC is inoperable Stage IIIA and/or IIIB NSCLC. In some embodiments, the NSCLC is inoperable Stage IIIA and/or IIIB NSCLC, PS 0-1, and FEV 1 >800 ml.

Further provided herein are methods of treating NSCLC in an individual (e.g., human) comprising administering to the individual a) an effective amount of a composition comprising nanoparticles comprising paclitaxel and an albumin (such as nanoparticles comprising paclitaxel coated with albumin, for example Nab-paclitaxel, i.e., the albumin stabilized nanoparticle formulation of paclitaxel sold under the trademark ABRAXANE®), and b) an effective amount of radiation (e.g. thoracic radiation), wherein the individual has diabetes, has four or more metastatic sites, and/or is at least about 70 years old. In some embodiments, the dose of paclitaxel in the composition comprising nanoparticles comprising paclitaxel and albumin is between 20 mg/m$^2$ to about 60 mg/m$^2$ (e.g., 40 mg/m$^2$), administered weekly and the thoracic radiation is between about 25 Gy to about 40 Gy (e.g., about 33 Gy) fractions by either 3D conformal or intensity-modulated techniques. In some embodiments, the treatment time is seven weeks and the thoracic radiation is concurrent. In some embodiments, the composition comprising nanoparticles comprising paclitaxel and albumin and the platinum-based agent are administered intravenously. In some embodiments, the composition comprising nanoparticles comprising paclitaxel and albumin are administered intravenously. In some embodiments NSCLC is inoperable Stage IIIA and/or IIIB NSCLC. In some embodiments, the NSCLC is inoperable Stage IIIA and/or IIIB NSCLC, PS 0-1, and FEV 1 >800 ml.

The methods described herein are useful for various aspects of NSCLC treatment. In some embodiments of any of the methods, the method comprises a method of inhibiting NSCLC cell proliferation (such as NSCLC tumor growth) in an individual, comprising administering to the individual a) an effective amount of a composition comprising nanoparticles comprising paclitaxel and an albumin and b) an effective amount of a platinum-based agent, wherein the individual has diabetes, has four or more metastatic sites, and/or is at least about 70 years old. In some embodiments, at least about 10% (including for example at least about any of 20%, 30%, 40%, 60%, 70%, 80%, 90%, or 100%) cell proliferation is inhibited.

In some embodiments of any of the methods, the method comprises a method of inhibiting NSCLC tumor metastasis in an individual, comprising administering to the individual a) an effective amount of a composition comprising nanoparticles comprising paclitaxel and an albumin and b) an effective amount of a platinum-based agent, wherein the individual has diabetes, has four or more metastatic sites, and/or is at least about 70 years old. In some embodiments, at least about 10% (including for example at least about any of 20%, 30%, 40%, 60%, 70%, 80%, 90%, or 100%) metastasis is inhibited. In some embodiments, a method of inhibiting metastasis to lymph node is provided.

In some embodiments of any of the methods, the method comprises a method of reducing NSCLC tumor size in an individual, comprising administering to the individual a) an effective amount of a composition comprising nanoparticles comprising paclitaxel and an albumin and b) an effective amount of a platinum-based agent, wherein the individual has diabetes, has four or more metastatic sites, and/or is at least about 70 years old. In some embodiments, the tumor size is reduced at least about 10% (including for example at least about any of 20%, 30%, 40%, 60%, 70%, 80%, 90%, or 100%).

In some embodiments of any of the methods, the method comprises a method of prolonging progression-free survival of NSCLC in an individual, comprising administering to the individual a) an effective amount of a composition comprising nanoparticles comprising paclitaxel and an albumin and b) an effective amount of a platinum-based agent, wherein the individual has diabetes, has four or more metastatic sites, and/or is at least about 70 years old. In some embodiments, the method prolongs the time to disease progression by at least any of 1, 2, 3, 4, 5, 6, 7, 8, 9, 10, 11, or 12 weeks.

In some embodiments of any of the methods, the method comprises a method of prolonging survival of an individual having NSCLC, comprising administering to the individual a) an effective amount of a composition comprising nanoparticles comprising paclitaxel and an albumin and b) an effective amount of a platinum-based agent, wherein the individual has diabetes, has four or more metastatic sites, and/or is at least about 70 years old. In some embodiments, the method prolongs the survival of the individual by at least any of 1, 2, 3, 4, 5, 6, 7, 8, 9, 10, 11, 12, 18, or 24 month.

In some embodiments of any of the methods, the method comprises a method of alleviating one or more symptoms in an individual having NSCLC, comprising administering to the individual a) an effective amount of a composition comprising nanoparticles comprising paclitaxel and an albumin and b) an effective amount of a platinum-based agent, wherein the individual has diabetes, has four or more metastatic sites, and/or is at least about 70 years old.

In some embodiments of any of the methods, the method comprises a method of reducing AEs and SAEs in an individual having NSCLC, comprising administering to the individual a) a composition comprising nanoparticles comprising paclitaxel and an albumin and b) a platinum-based agent, wherein the reduction is based on a comparison with the AEs and SAEs resulting from administering to the individual a) paclitaxel dissolved in polyoxyethylated castor oil and dehydrated alcohol, sold under the trademark TAXOL® and b) a platinum-based agent, wherein the individual has diabetes, has four or more metastatic sites, and/or is at least about 70 years old.

In some embodiments of any of the methods described herein, the method of treatment results in an objective response (such as a partial response or complete response).

In some embodiments of any of the methods described herein, the method of treatment results in improved quality of life.

In some embodiments of any of the methods described herein, an individual (e.g., human) who has been diagnosed with or is suspected of having NSCLC can be treated. In some embodiments, the individual is human. In some embodiments, the individual is at least about any of 35, 40, 45, 50, 55, 60, 65, 70, 75, 80, or 85 years old. In some embodiments, the individual is male. In some embodiments, the individual is a female. In some embodiments, the individual has any of the types of NSCLC described herein. In some embodiments, the individual has a single lesion at presentation. In some embodiments, the individual has multiple lesions at presentation. In some embodiments, the individual is resistant to treatment of NSCLC with other agents (such as a non-nanoparticle formulation of taxane, e.g., paclitaxel dissolved in polyoxyethylated castor oil and dehydrated alcohol, sold under the trademark TAXOL® or docetaxel dissolved in polysorbate 80, polyethylene glycol, alcohol, and citric acid, sold under the trademark TAXOTERE®). In some embodiments, the individual is initially responsive to treatment of NSCLC with other agents (such as a non-nanoparticle formulation of taxane, e.g., paclitaxel dissolved in polyoxyethylated castor oil and dehydrated alcohol, sold under the trademark TAXOL® or docetaxel dissolved in polysorbate 80, polyethylene glycol, alcohol, and citric acid, sold under the trademark TAXOTERE®) but has progressed after treatment.

In some embodiments of any of the methods, the methods further include administration of an effective amount of an anti-angiogenic agent (e.g., angiogenesis inhibitor). In some embodiments, the anti-angiogenic agent is bevacizumab, sunitinib, or sorafenib tosylate. In some embodiments, the anti-angiogenic agent is bevacizumab. In some embodiments, the effective amount of bevacizumab is between about 5 mg/kg and about 15 mg/kg. In some embodiments, the effective amount of bevacizumab is about any of 5 mg/kg, 7.5 mg/kg, 10 mg/kg, or 15 mg/kg.

In some embodiments, a lower amount of each pharmaceutically active compound is used as part of a combination therapy compared to the amount generally used for individual therapy. In some embodiments, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. For example, the use of a small amount of pharmaceutically active compound may result in a reduction in the number, severity, frequency, or duration of one or more side-effects associated with the compound.

The methods described herein can be used for any one or more of the following purposes: alleviating one or more symptoms of NSCLC, delaying progressing of NSCLC, shrinking tumor size in NSCLC patient, inhibiting NSCLC tumor growth, prolonging overall survival, prolonging progression free survival, preventing or delaying NSCLC tumor metastasis, reducing (such as eradicating) preexisting NSCLC tumor metastasis, reducing incidence or burden of preexisting NSCLC tumor metastasis, or preventing recurrence of NSCLC.

In some embodiments of any of the methods described herein, the individual is a human who exhibits one or more symptoms associated with NSCLC. In some embodiments, the individual is genetically or otherwise predisposed (e.g., having a risk factor) to developing NSCLC. These risk factors include, but are not limited to, age, sex, race, diet, history of previous disease, presence of precursor disease, genetic (e.g., hereditary) considerations, and environmental exposure (e.g., cigarette, pipe, or cigar smoking, exposure to second-hand smoke, radon, arsenic, asbestos, chromates, chloromethyl ethers, nickel, polycyclic aromatic hydrocarbons, radon progeny, other agents, or air pollution). In some embodiments, the individuals at risk for NSCLC include, e.g., those having relatives who have experienced NSCLC, and those whose risk is determined by analysis of genetic or biochemical markers.

In some embodiments, the individual has an elevated glucose level as compared to a normal individual. In some embodiments, the individual has diabetes. Diabetes mellitus is characterized by a loss of the ability to regulate blood glucose levels. Diabetes is generally diagnosed by determining blood glucose levels after fasting overnight (fasting plasma glucose level) or by determining blood glucose levels after fasting, followed by ingestion of glucose and a blood glucose measurement two hours after glucose administration (a glucose tolerance test). Individuals suffering from diabetes often experience long-term complications such as blindness, kidney failure, and nerve damage. In some embodiments, the individual is genetically or otherwise predisposed (e.g., having a risk factor) to develop diabetes. These risk factors include, but are not limited to, obesity, waist size, disease of the pancreas, sedentary lifestyle, family history, having a prior history with gestational diabetes, having high blood pressure (e.g., measuring 140/90 or higher), having abnormal cholesterol with HDL measuring over 35 or triglyceride level measuring over 250, increasing age, and ethnicity (e.g., African American, Hispanic/Latino, Native American, Asian American or Pacific Islander).

In some embodiments, the individual is obese (e.g., has a BMI of 30 or greater). In some embodiments, the individual has a fasting plasma glucose level of at least about 7.0 mmol/1 (126 mg/dl) (such as at least about 8 mmol/1, at least about 9 mmol/1, at least about 10 mmol/1, at least about 11 mmol/1, at least about 12 mmol/1, at least about 13 mmol/1, at least about 14 mmol/1, at least about 15 mmol/1, at least about 16 mmol/1, or more than about 16 mmol/1). In some embodiments, the individual has plasma glucose level of at least about 11.1 mmol (200 mg/dL) (such as at least about 11.5 mmol/1, at least about 12.0 mmol/1, at least about 13.0 mmol/1, at least about 14 mmol/1, at least about 15 mmol/1, at least about 16 mmol/1, at least about 17 mmol/1, at least about 18 mmol/1, at least about 19 mmol/1, at least about 20 mmol/1, or more than 20 mmol/1) two hours after a 75 g oral glucose load as in a glucose tolerance test. In some embodiments, the individual has symptoms of hyperglycemia, which includes, but not limited to, headaches, difficulty concentrating, blurred vision, frequent urination, fatigue, weight loss, slow healing cuts and sores, and stomach and intestinal problems. In some embodiments, the individual has a symptom of hyperglycemia and a casual plasma glucose level of at least about 11.0 mmol/1 (200 mg/dl) (such as at least about 11.5 mmol/1, at least about 12.0 mmol/1, at least about 13.0 mmol/1, at least about 14 mmol/1, at least about 15 mmol/1, at least about 16 mmol/1, at least about 17 mmol/1, at least about 18 mmol/1, at least about 19 mmol/1, at least about 20 mmol/1, or more than 20 mmol/l). In some embodiments, the individual has any of 1, 2, 3, 4, or more of the characteristics described herein.

In some embodiments, the individual has type I Diabetes. Type I Diabetes (insulin-dependent Diabetes or childhood-onset Diabetes) results from a lack of insulin production due to an autoimmune mediated destruction of the beta cells of the pancreas. Patients with Type I Diabetes exhibit little or no insulin secretion as manifested by low or undetectable levels of insulin or plasma C-peptide (also known in the art as "soluble C-peptide"). Patients with Type I Diabetes require daily administration of insulin for survival and are at risk for ketoacidosis.

In some embodiments, the individual has type II Diabetes. Type II Diabetes (non-insulin-dependent Diabetes or adult-onset Diabetes) results from insensitivity to insulin, and accounts for 90% of Diabetes worldwide. Type II Diabetes is characterized by disorders of insulin action and insulin secretion, either of which may be the predominant feature. Type II Diabetes patients are characterized with a relative, rather than absolute, insulin deficiency and are insulin resistant. At least initially, and often throughout their lifetime, these individuals do not need supplemental insulin treatment to survive. Type II Diabetes accounts for 90-95% of all cases of diabetes and can go undiagnosed for many years.

In some embodiments, the individual is diagnosed as having diabetes using the A1C test, also called the hemoglobin A1c, HbA1c, or glycohemoglobin test. The A1C test is a blood test that provides information about a person's average levels of blood glucose over a period of time (for example for the past 3 months).

In some embodiments, the individual has four or more (such as 5, 6, 7, 8, 9, 10, or more) metastatic sites.

Also provided are methods of treating NSCLC in an individual comprising administering to the individual a) an effective amount of a composition comprising nanoparticles comprising paclitaxel and an albumin and b) an effective amount of a platinum-based agent, wherein treatment is based upon the individual having one or more (such as 1, 2, or 3) characteristics selected from the group consisting of (i) having diabetes, (ii) having four or more metastatic sites, and (iii) is at least about 70 years old. In some embodiments, the treatment is further based on the NSCLC having one or more (such as any of 1, 2, 3, 4, 5, 6, 7, 8, 9, 10, 11, or 12) characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

Further provided herein are methods of treating NSCLC in an individual provided that the individual has been found to have one or more (such as any of 1, 2, or 3) characteristics selected from the group consisting of (i) has diabetes, (ii) has four or more metastatic sites, and (iii) is at least about 70 years old, the treatment comprising administering to the individual i) an effective amount of a composition comprising nanoparticles comprising paclitaxel and an albumin and ii) an effective amount of a platinum-based agent. In some embodiments, the NSCLC has further been found to have one or more (such as any of 1, 2, 3, 4, 5, 6, 7, 8, 9, 10, 11, or 12) characteristics selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (l) differential albumin uptake.

Also provided are methods of adjusting dosages (e.g., reducing dosages) in an individual treated with i) an effective amount of a composition comprising nanoparticles comprising paclitaxel and an albumin and ii) an effective amount of a platinum-based agent, wherein the individual has one or more (such as any of 1, 2, or 3) characteristics selected from the group consisting of (i) has diabetes, (ii) has four or more metastatic sites, and (iii) is at least about 70 years old. For example, in some embodiments, there is provided a method of adjusting dosages (e.g., reducing dosages) in an individual treated with i) an effective amount of a composition comprising nanoparticles comprising paclitaxel and an albumin and ii) an effective amount of a platinum-based agent, wherein the individual is at least about 70 years old.

Provided herein are also methods of treating NSCLC, comprising: (a) selecting an individual having NSCLC, wherein the individual has one or more (such as any of 1, 2, or 3) characteristics selected from the group consisting of (i) has diabetes, (ii) has four or more metastatic sites, and (iii) is at least about 70 years old; and (b) administering to the individual thus selected i) an effective amount of a composition comprising nanoparticles comprising paclitaxel and an albumin and ii) an effective amount of a platinum-based agent. In some embodiments, the NSCLC further has one or more (such as any of 1, 2, 3, 4, 5, 6, 7, 8, 9, 10, 11, or 12) characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

Methods are also provided herein of assessing whether an individual with NSCLC will respond to treatment comprising assessing one or more (such as any of 1, 2, or 3) characteristics of the individual selected from the group consisting of (i) has diabetes, (ii) has four or more metastatic sites, and (iii) is at least about 70 years old, wherein one or more of the characteristics of the NSCLC indicates the individual will be responsive to the treatment and the treatment comprises i) an effective amount of a composition comprising nanoparticles comprising paclitaxel and an albumin and ii) an effective amount of a platinum-based agent. In some embodiments, the method further comprises assessing one or more (such as any of 1, 2, 3, 4, 5, 6, 7, 8, 9, 10, 11, or 12) characteristics of the NSCLC selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (l) differential albumin uptake. In some embodiments, the method further comprises administering to the identified individual a) an effective amount of a composition comprising nanoparticles comprising a taxane and an albumin; and b) an effective amount of a platinum-based agent.

In addition, the method may further comprise identifying an individual with NSCLC likely to respond to treatment comprising a) a composition comprising nanoparticles comprising paclitaxel and an albumin and b) a platinum-based agent comprising: (A) assessing one or more (such as any of 1, 2, or 3) characteristics of the individual selected from the group consisting of (i) has diabetes, (ii) has four or more metastatic sites, and (iii) is at least about 70 years old, and (B) identifying the individual has likely to respond to treatment if the individual has one or more such characteristics. In some embodiments, the method further comprises assessing one or more (such as any of 1, 2, 3, 4, 5, 6, 7, 8, 9, 10, 11, or 12) characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (B) identifying the individual having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake. In some embodiments, the method further comprises administering to the identified individual a) an effective amount of a composition comprising nanoparticles comprising a taxane and an albumin; and b) an effective amount of a platinum-based agent.

Provided herein are also methods for marketing a combination therapy comprising a) a composition comprising nanoparticles comprising paclitaxel and an albumin and b) a platinum-based agent for use in a NSCLC individual subpopulation, the methods comprising informing a target audience about the use of the combination therapy for treating the individual subpopulation characterized by the individuals of such subpopulation having one or more (such as any of 1, 2, or 3) characteristics selected from the group consisting of (i) having diabetes, (ii) having four or more metastatic sites, and (iii) is at least about 70 years old. In some embodiments, the individual subpopulation is further characterized by the NSCLC having one or more (such as any of 1, 2, 3, 4, 5, 6, 7, 8, 9, 10, 11, or 12) characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

In some embodiments of any of the methods, the one or more characteristics of the individual or the NSCLC of the individual include 1, 2, or 3 characteristics of the individual and/or 1, 2, 3, 4, 5, 6, 7, 8, 9, 10, 11, or 12 characteristics of NSCLC. In some embodiments, the one or more characteristics include, for example, at least two or more characteristics, at least three or more characteristics, at least four or more characteristics, or at least five or more characteristics. For example, in some embodiments, the individual is characterized by having diabetes and at least about 70 years old. In some embodiments, the individual is characterized by having diabetes and the NSCLC is characterized by squamous cell carcinoma. In some embodiments, the individual is characterized by having diabetes and is at least about 70 years old, and the NSCLC is characterized by squamous cell carcinoma. In some embodiments, the individual is characterized by having diabetes, has four or more metastatic sites, and is at least about 70 years old, and the NSCLC is characterized by squamous cell carcinoma. In some embodiments, the individual is characterized by having diabetes and the NSCLC is characterized by differentially levels of CAV-1 and squamous cellular carcinoma. In some embodiments, the individual is characterized by having diabetes, has four or more metastatic sites, and/or is at least about 70 years old, and the NSCLC is characterized by differential levels of CAV-1, squamous cellular carcinoma, and differential levels of SPARC. In some embodiments, the individual is characterized by having diabetes, has four or more metastatic sites, and/or is at least about 70 years old, and the NSCLC is characterized by differential levels of CAV-1, squamous cellular carcinoma, differential levels of SPARC, and differential levels of hypoxia markers. In some embodiments, the individual is characterized by (i) has diabetes, (ii) has four or more metastatic sites, and (iii) is at least about 70 years old, and the NSCLC is characterized by (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

The differential levels of tumor acidity may be evidenced by, for example, differential levels of carbonic anhydrase-9 (CA-9) and/or differential levels of LDH (e.g., LDH-5).

The differential levels of hyopoxia markers may be evidenced by, for example, differential levels of HIF-1α, differential levels of HIF-2α, and/or differential levels of differentiated embryo-chrondrocyte expressed gene 1 (DEC-1).

In some embodiments, the one or more characteristics of NSCLC comprises differential levels of SPARC. SPARC (Secreted Protein, Acidic and Rich in Cysteine) is a matricellular protein upregulated in several aggressive cancers. See Porter et al., *J. Histochem. Cytochem.* 1995; 43:791. The human SPARC gene encodes a 303 amino acid SPARC proteins, while mature SPARC is a 285 amino acid glycoprotein. After cleavage of the signal sequence a 32-kD secreted form is produced which migrates at 43 kD on SDA-PAGE because of glycosylation. In some embodiments, differential levels is determined in tumor tissue, normal tissue adjacent to said tumor, normal tissue distal to said tumor or peripheral blood lymphocytes. In some embodiments, the drug uptake capability is based on the level of SPARC on the tumor stroma.

In some embodiments of any of the methods, differential levels are determined in tumor tissue, normal tissue adjacent to said tumor, normal tissue distal to said tumor or peripheral blood lymphocytes.

"Differential levels" or "differential" as applied to a gene, may refer to a variance in the nucleic acid sequence, methylation state or degree of methylation, or production of the nucleic acid transcribed from the gene or the protein product encoded by the gene. In some embodiments, a differentially expressed gene may be over expressed (high expression) or under expressed (low expression) as compared to the expression level of a normal or control cell, a given patient population, or with an internal control. In some embodiments, the differential is about any of 1.5 times, 2.0 times, 2.5 times, 3.0 times, 5.0 times, 10 times, 50 times, or 100 times higher than the expression level detected in a control sample. In some embodiments, the differential is about any of 1.5 times, 2.0 times, 2.5 times, 3.0 times, 5.0 times, 10 times, 50 times, or 100 times lower than the expression level detected in a control sample. In some embodiments, the nucleotide sequences in a cell or tissue which are expressed where silent in a control cell or not expressed where expressed in a control cell.

In some embodiments, expression level is determined by measuring the expression level of a gene of interest for a given patient population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression of the gene of interest. Alternatively, if the expression level of a gene of interest for the single patient is determined to be below the median expression level of the patient population, that patient is determined to have low expression of the gene of interest. In some embodiments, the single patient has NSCLC and the patient population does not have cancer (i.e., normal). In some embodiments, the single patient has one histological type of NSCLC (e.g., squamous cell carcinoma) and the patient population has a second histological type of NSCLC (e.g., adenocarcinoma). In some embodiments, the single patient and the patient population have the same histological type of NSCLC (e.g., squamous cell carcinoma).

To practice this method, the sample is a patient sample containing the tumor tissue, normal tissue adjacent to said tumor, normal tissue distal to said tumor or peripheral blood lymphocytes. Sample nucleic acid for use in the above-described methods can be obtained from any cell type or tissue of a subject. For example, a subject's bodily fluid (e.g. blood) can be obtained by known techniques (e.g., venipuncture). Alternatively, tests can be performed on dry samples (e.g., hair or skin).

In some embodiments, the method comprises isolating a sample containing the genetic material to be tested. In some embodiments, the method comprises determining differential levels in situ. Accordingly, the methods of this application are not to be limited to requiring isolation of the genetic material prior to analysis.

These methods to identify expression levels are not limited by the technique that is used to identify the expression level of the gene of interest. Nucleic acid (e.g., RNA or DNA) or protein levels of the gene of interest can be measured. Methods for measuring gene expression and/or determining sequence for detection of polymorphism are well known in the art and include, but are not limited to, immunological assays, nuclease protection assays, northern blots, in situ hybridization, ELISA, reverse transcriptase Polymerase Chain Reaction (RT-PCR), Real-Time Polymerase Chain Reaction, expressed sequence tag (EST) sequencing, cDNA microarray hybridization or gene chip analysis, subtractive cloning, Serial Analysis of Gene Expression (SAGE), Massively Parallel Signature Sequencing (MPSS), and Sequencing-By-Synthesis (SBS). Diagnostic procedures can also be performed in situ directly upon tissue sections (fixed and/or frozen) of patient tissue obtained from biopsies or resections.

Amplification of polynucleotides includes methods such as PCR, ligation amplification (or ligase chain reaction, LCR) and amplification methods. These methods are known and widely practiced in the art. In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

In some embodiments of any of the methods herein, the methods result in a measurable reduction in tumor size or evidence of disease or disease progression, complete response, partial response, stable disease, increase or elongation of progression free survival, or increase or elongation of overall survival. In some embodiments of any of the methods above, a patient is likely to respond as evident by a measurable reduction in tumor size or evidence of disease or disease progression, complete response, partial response, stable disease, increase or elongation of progression free survival, increase or elongation of overall survival. In some embodiments, at least about 10% (including for example at least about any of 20%, 30%, 40%, 60%, 70%, 80%, 90%, or 100%) cell proliferation is inhibited. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided. In some embodiments, the tumor size is reduced at least about 10% (including for example at least about any of 20%, 30%, 40%, 60%, 70%, 80%, 90%, or 100%). In some embodiments, the method prolongs the progression free survival by at least any of 1, 2, 3, 4, 5, 6, 7, 8, 9, 10, 11, or 12 weeks. In some embodiments, the method prolongs the progression free survival of the individual by at least any of 1, 2, 3, 4, 5, 6, 7, 8, 9, 10, 11, 12, 18, or 24 month. In some embodiments, the method prolongs the survival of the individual by at least any of 1, 2, 3, 4, 5, 6, 7, 8, 9, 10, 11, 12, 18, or 24 month.

In some embodiments of any of the methods herein, the methods result in improved quality of life.

The methods herein are applicable to multiple histological types of NSCLC. The NSCLC may be squamous cell carcinoma (i.e., epidermoid carcinoma), large cell carcinoma, adenocarcinoma, adenosquamous carcinoma, carcinomas with pleomorphic, sarcomatoid, or sarcomatous elements, carcinoid tumor, or salivary gland carcinoma. In some embodiments the NSCLC is squamous cell carcinoma. In some embodiments, the squamous cell carcinoma is papillary, clear cell, small cell, or basaloid. In some embodiments, the NSCLC is adenocarcinoma. In some embodiments, the adenocarcinoma is acinar, papillary, bronchioloalveolar carcinoma (e.g., nonmucinous, mucinous, mixed mucinous and nonmucinous or indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, or clear cell adenocarcinoma. In some embodiments, the large cell carcinoma is large-cell neuroendocrine carcinoma, combined large-cell neuroendocrine carcinoma, basaloid carcinoma, lymphoepithelioma-like carcinoma, clear cell carcinoma, or large cell carcinoma with rhabdoid phenotype. In some embodiments, the carcinoma with pleomorphic, sarcomatoid, or sarcomatous elements is carcinomas with spindle and/or giant cells, spindle cell carcinoma, giant cell carcinoma, carcinosarcoma, or pulmonary blastoma. In some embodiments, the carcinoma of salivary-gland type is mucoepidermoid carcinoma or adenoid cystic carcinoma.

The NSCLC of any of the methods herein may be an occult tumor, a stage 0 tumor, a stage I tumor (stage IA (T1, N0, M0) or stage IB (T2, N0, M0)), a stage II tumor (stage IIA (T1, N1, M0) and stage IIB (T2, N1, M0)), a stage IIIA tumor (T1, N2, M0, T2, N2, M0, T3, N1, M0, or T3, N2, M0), a stage IIIB tumor (Any T, N3, M0 or T4, any N, M0), or a stage IV tumor (Any T, any N, M1). In some embodiments of any of the methods described herein, the NSCLC is early stage NSCLC, non-metastatic NSCLC, primary NSCLC, advanced NSCLC, locally advanced NSCLC, metastatic NSCLC, NSCLC in remission, or recurrent NSCLC. In some embodiments, the NSCLC is localized resectable, localized unresectable, or unresectable.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first-line therapy. In some embodiments, the method is used as a second-line therapy.

In some embodiments of any of the methods described herein, the composition comprising nanoparticles comprising paclitaxel and an albumin (such as human serum albumin), wherein paclitaxel in the nanoparticles is coated with the albumin. In some embodiments, the average particle size of the nanoparticles in the composition is no greater than about 200 nm (such as less than about 200 nm). In some embodiments, the composition comprises Nab-paclitaxel, i.e., the albumin stabilized nanoparticle formulation of paclitaxel sold under the trademark ABRAXANE®. In some embodiments, the composition is the Nab-paclitaxel, i.e., the albumin stabilized nanoparticle formulation of paclitaxel sold under the trademark ABRAXANE®. In some embodiments, the nanoparticle composition and the platinum-based agent have synergistic effect on treating NSCLC.

Platinum-based agent binds covalently to DNA and cross-links strands, inhibits DNA synthesis, and/or inhibits transcript. In some embodiments, the platinum-based agent is carboplatin, cisplatin, or oxaliplatin. In some embodiments, the platinum-based agent is carboplatin. In some embodiments, the platinum-based agent is cisplatin.

In some embodiments, the dose of paclitaxel in the composition comprising nanoparticles comprising paclitaxel and the albumin is between about 40 mg/m$^2$ to about 125 mg/m$^2$ or between about 50 mg/m$^2$ to about 125 mg/m$^2$ (e.g., 40 mg/m$^2$, 50 mg/m$^2$, 60 mg/m$^2$, 75 mg/m$^2$, or 100 mg/m$^2$) and the effective amount of the platinum-based agent is between about AUC=2 to about AUC=6 (e.g., AUC=2, AUC=3, AUC=4.5, or AUC=6). In some embodiments, the effective amount of the composition comprising nanoparticles comprising paclitaxel and the albumin is administered weekly and the effective amount of the platinum-based agent is administered every three weeks. In some embodiments, the effective amount of the composition comprising nanoparticles comprising paclitaxel and the albumin is administered weekly and the effective amount of the platinum-based agent is administered weekly. In some embodiments, the dose of paclitaxel in the composition comprising nanoparticles comprising paclitaxel and the albumin is between about 50 mg/m$^2$ to about 125 mg/m$^2$ administered weekly and the effective amount of the platinum-based agent is between about AUC=2 to about AUC=6 administered once every three weeks. In some embodiments, the dose of paclitaxel in the composition comprising nanoparticles comprising paclitaxel and the albumin is between about 40 mg/m$^2$ to about 125 mg/m$^2$ administered weekly and the effective amount of the platinum-based agent is between about AUC=2 to about AUC=6 administered weekly. In some embodiments, the dose of paclitaxel in the composition comprising nanoparticles comprising paclitaxel and the albumin is about 100 mg/m$^2$ administered weekly and the effective amount of the platinum-based agent is about AUC=6 administered once every three weeks. In some embodiments, the dose of paclitaxel in the composition comprising nanoparticles comprising paclitaxel and the albumin is about 75 mg/m$^2$ administered weekly and the effective amount of the platinum-based agent is about AUC=4.5 administered once every three weeks. In some embodiments, the dose of paclitaxel in the composition comprising nanoparticles comprising paclitaxel and the albumin is about 50 mg/m$^2$ administered weekly and the effective amount of the platinum-based agent is about AUC=3 administered once every three weeks. In some embodiments, the dose of paclitaxel in the composition comprising nanoparticles comprising paclitaxel and the albumin is about 40 mg/m$^2$ administered weekly and the effective amount of the platinum-based agent is about AUC=2 administered weekly. In some embodiments, the paclitaxel nanoparticle composition and/or the platinum-based agent is administered intravenously. In some embodiments, the paclitaxel nanoparticle composition and the platinum-based agent are administered intravenously.

In some embodiments of any of the methods, the composition comprising nanoparticles comprising paclitaxel and albumin is administered without any steroid premedication and/or without G-CSF prophylaxis.

In some embodiments of any of the methods, the methods further include administration of an effective amount of an anti-angiogenic agent (e.g., angiogenesis inhibitor). In some embodiments, the anti-angiogenic agent is bevacizumab, sunitinib, or sorafenib tosylate. In some embodiments, the anti-angiogenic agent is bevacizumab. In some embodiments, the effective amount of bevacizumab is between about 5 mg/kg and about 15 mg/kg. In some embodiments, the effective amount of bevacizumab is about any of 5 mg/kg, 7.5 mg/kg, 10 mg/kg, or 15 mg/kg.

Dosing and Method of Administering the Nanoparticle Compositions

The dose of the paclitaxel nanoparticle compositions administered to an individual (such as a human) may vary with the particular composition, the mode of administration, and the type of NSCLC being treated. In some embodiments, the amount of the paclitaxel nanoparticle composition and/or the amount of the platinum-based agent (e.g. carboplatin) is effective to result in an objective response (such as a partial response or a complete response). In some embodiments, the amount of the paclitaxel nanoparticle composition and/or the amount of the platinum-based agent (e.g. carboplatin) is sufficient to result in a complete response in the individual. In some embodiments, the amount of the paclitaxel nanoparticle composition and/or the amount of the platinum-based agent (e.g. carboplatin) is sufficient to result in a partial response in the individual. In some embodiments, the amount of the paclitaxel nanoparticle composition and the amount of the platinum-based agent (e.g. carboplatin) is sufficient to result in a higher objective response (such as a complete response or a partial response) in the individual compared to a paclitaxel nanoparticle composition alone, paclitaxel dissolved in polyoxyethylated castor oil and dehydrated alcohol, sold under the trademark TAXOL® alone, a platinum-based agent (e.g. carboplatin) alone, and/or the combination of paclitaxel dissolved in polyoxyethylated castor oil and dehydrated alcohol, sold under the trademark TAXOL® and platinum-based agent (e.g. carboplatin). Responses of an individual to the treatment of the methods described herein can be determined, for example, based on Response Evaluation Criteria In Solid Tumors (RECIST) levels.

In some embodiments, the amount of the paclitaxel nanoparticle composition and/or the amount of the platinum-based agent (e.g. carboplatin) is sufficient to increase progression-free survival of the individual. In some embodiments, the amount of the paclitaxel nanoparticle composition and/or the amount of the platinum-based agent (e.g., carboplatin) is sufficient to prolong overall survival of the individual. In some embodiments, the amount of the paclitaxel nanoparticle composition and the amount of the platinum-based agent (e.g. carboplatin) is sufficient to increase progression-free survival of the individual compared to a paclitaxel nanoparticle composition alone, paclitaxel dissolved in polyoxyethylated castor oil and dehydrated alcohol, sold under the trademark TAXOL® alone, a platinum-based agent (e.g. carboplatin) alone, and/or the combination of paclitaxel dissolved in polyoxyethylated castor oil and dehydrated alcohol, sold under the trademark TAXOL® and platinum-based agent (e.g. carboplatin).

In some embodiments, the amount of the paclitaxel nanoparticle composition and/or the amount of the platinum-based agent (e.g., carboplatin) is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of NSCLC cells, or tumor growth rate in the same subject at the time of starting treatment or compared to the corresponding activity in other subjects not receiving the treatment. In some embodiments, the amount of the paclitaxel nanoparticle composition and the amount of the platinum-based agent (e.g. carboplatin) is sufficient to decrease the size of a tumor, decrease the number of cancer cells, or decrease the growth rate of a tumor at the time of starting treatment by more than at least about any of 10%, 20%, 30%, 40%, 50%, 60%, 70%, 80%, 90%, 95% or 100% compared to a paclitaxel nanoparticle composition alone, paclitaxel dissolved in polyoxyethylated castor oil and dehydrated alcohol, sold under the trademark TAXOL® alone, a platinum-based agent (e.g. carboplatin) alone, and/or the combination of paclitaxel dissolved in polyoxyethylated castor oil and dehydrated alcohol, sold under the trademark TAXOL® and platinum-based agent (e.g. carboplatin). Standard methods can be used to measure the magnitude of this effect.

In some embodiments, the amount of the paclitaxel in the nanoparticle composition is below the level that induces a toxicological effect (i.e., an effect above a clinically acceptable level of toxicity) or is at a level where a potential side effect can be controlled or tolerated when the nanoparticle composition is administered to the individual.

In some embodiments, the amount of the paclitaxel nanoparticle composition and/or the amount of the platinum-based agent (e.g. carboplatin) is close to a maximum tolerated dose (MTD) of the composition following the same dosing regime. In some embodiments, the amount of the composition is more than about any of 80%, 90%, 95%, or 98% of the MTD.

In some embodiments, the amount of paclitaxel in the nanoparticle composition is included in any of the following ranges: about 0.1 mg to about 500 mg, about 0.1 mg to about 2.5 mg, about 0.5 to about 5 mg, about 5 mg to about 10 mg, about 10 mg to about 15 mg, about 15 mg to about 20 mg, about 20 mg to about 25 mg, about 20 mg to about 50 mg, about 25 mg to about 50 mg, about 50 mg to about 75 mg, about 50 mg to about 100 mg, about 75 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 300 mg, about 300 mg to about 350 mg, about 350 mg to about 400 mg, about 400 mg to about 450 mg, or about 450 mg to about 500 mg. In some embodiments, the amount of paclitaxel in the effective amount of the nanoparticle composition (e.g., a unit dosage form) is in the range of about 5 mg to about 500 mg, such as about 30 mg to about 300 mg or about 50 mg to about 200 mg. In some embodiments, the concentration of paclitaxel in the nanoparticle composition is dilute (about 0.1 mg/ml) or concentrated (about 100 mg/ml), including for example any of about 0.1 mg/ml to about 50 mg/ml, about 0.1 mg/ml to about 20 mg/ml, about 1 mg/ml to about 10 mg/ml, about 2 mg/ml to about 8 mg/ml, about 4 mg/ml to about 6 mg/ml, or about 5 mg/ml. In some embodiments, the concentration of paclitaxel is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of paclitaxel in the nanoparticle composition include, but are not limited to, at least about any of 25 mg/m², 30 mg/m², 50 mg/m², 60 mg/m², 75 mg/m², 80 mg/m², 90 mg/m², 100 mg/m², 120 mg/m², 125 mg/m², 150 mg/m², 160 mg/m², 175 mg/m², 180 mg/m², 200 mg/m², 210 mg/m², 220 mg/m², 250 mg/m², 260 mg/m², 300 mg/m², 350 mg/m², 400 mg/m², 500 mg/m², 540 mg/m², 750 mg/m2, 1000 mg/m², or 1080 mg/m² of paclitaxel. In various embodiments, the composition includes less than about any of 350 mg/m², 300 mg/m², 250 mg/m², 200 mg/m², 150 mg/m², 120 mg/m², 100 mg/m², 90 mg/m², 50 mg/m², or 30 mg/m² of paclitaxel. In some embodiments, the amount of paclitaxel per administration is less than about any of 25 mg/m², 22 mg/m², 20 mg/m², 18 mg/m², 15 mg/m², 14 mg/m², 13 mg/m², 12 mg/m², 11 mg/m², 10 mg/m², 9 mg/m², 8 mg/m², 7 mg/m², 6 mg/m², 5 mg/m², 4 mg/m², 3 mg/m², 2 mg/m², or 1 mg/m². In some embodiments, the effective amount of paclitaxel in the nanoparticle composition is included in any of the following ranges: about 1 mg/m² to about 5 mg/m², about 5 mg/m² to about 10 mg/m², about 10 mg/m² to about 25 mg/m², about 25 mg/m² to about 50 mg/m², about 50 mg/m² to about 75 mg/m², about 75 mg/m² to about 100 mg/m², about 100 mg/m² to about 125 mg/m², about 125 mg/m² to about 150 mg/m², about 150 mg/m² to about 175 mg/m², about 175 mg/m² to about 200 mg/m², about 200 mg/m² to about 225 mg/m², about 225 mg/m² to about 250 mg/m², about 250 mg/m² to about 300 mg/m², about 300 mg/m² to about 350 mg/m², or about 350 mg/m² to about 400 mg/m². In some embodiments, the effective amount of paclitaxel in the nanoparticle composition is about 5 mg/m² to about 300 mg/m², such as about 20 mg/m² to about 60 mg/m², about 100 mg/m² to about 150 mg/m², about 120 mg/m², about 130 mg/m², or about 140 mg/m2.

In some embodiments of any of the above aspects, the effective amount of paclitaxel in the nanoparticle composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the effective amount of paclitaxel in the nanoparticle composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of paclitaxel.

Exemplary dosing frequencies for the administration of the paclitaxel nanoparticle compositions include, but are not limited to, daily, every two days, every three days, every four days, every five days, every six days, weekly without break, three out of four weeks, once every three weeks, once every two weeks, or two out of three weeks. In some embodiments, the paclitaxel nanoparticle composition is administered about once every 2 weeks, once every 3 weeks, once every 4 weeks, once every 6 weeks, or once every 8 weeks. In some embodiments, the paclitaxel nanoparticle composition is administered at least about any of 1×, 2×, 3×, 4×, 5×, 6×, or 7× (i.e., daily) a week. In some embodiments, the paclitaxel nanoparticle composition is administered weekly. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, paclitaxel in the nanoparticle composition is administered over a period of at least ten days, wherein the interval between each administration is no more than about two days, and wherein the dose of paclitaxel at each administration is about 0.25 mg/m² to about 250 mg/m², about 0.25 mg/m² to about 150 mg/m², about 0.25 mg/m² to about 75 mg/m², such as about 0.25 mg/m² to about 25 mg/m², about 20 mg/m² to about 60 mg/m², or about 25 mg/m² to about 50 mg/m².

The administration of the paclitaxel nanoparticle composition can be extended over an extended period of time, such as from about a month up to about seven years. In some embodiments, the paclitaxel nanoparticle composition is administered over a period of at least about any of 2, 3, 4, 5, 6, 7, 8, 9, 10, 11, 12, 18, 24, 30, 36, 48, 60, 72, or 84 months.

In some embodiments, the dosage of paclitaxel in a nanoparticle composition can be in the range of 5 mg/m²–400 mg/m² when given on a 3 week schedule, or 5 mg/m²–250 mg/m² (such as 40 mg/m²-100 mg/m², 50 mg/m²–125 mg/m², for example 50 mg/m²–100 mg/m²) when given on a weekly schedule. For example, the amount of paclitaxel is about 50 mg/m² to about 125 mg/m² (e.g., about 100 mg/m²) on a weekly schedule, e.g., weekly without a break.

Other exemplary dosing schedules for the administration of paclitaxel in the nanoparticle composition include, but are not limited to, 100 mg/m², weekly, without break; 75 mg/m², weekly, without break; 50 mg/m², weekly, without break; 100 mg/m² weekly, 3 out of 4 weeks; 75 mg/m² weekly, 3 out of four weeks; or 50 mg/m² weekly, 3 out of 4 weeks. The dosing frequency of the composition may be adjusted over the course of the treatment based on the judgment of the administering physician.

In some embodiments of any of the above aspects, the cumulative dose of paclitaxel in the nanoparticulate composition administered includes at least about any of 1000 mg/m², 1100 mg/m², 1200 mg/m², 1300 mg/m², 1400 mg/m², 1450 mg/m², 1500 mg/m², 1600 mg/m², or 1700 mg/m². In some embodiments, the cumulative dose of paclitaxel in the nanoparticulate composition is between about any of 1000 mg/m² to 1700 mg/m², 1100 mg/m² to 1600 mg/m², 1200 mg/m² to 1600 mg/m², 1300 mg/m² to 1600 mg/m², or 1400 mg/m² to 1500 mg/m².

In some embodiments, the individual is treated for at least about any of one, two, three, four, five, six, seven, eight, nine, or ten treatment cycles.

The paclitaxel nanoparticle compositions described herein allow infusion of the paclitaxel nanoparticle composition to an individual over an infusion time that is shorter than about 24 hours. For example, in some embodiments, the paclitaxel nanoparticle composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

In some embodiments, the amount of the platinum-based agent (e.g. carboplatin) is between about any of AUC=1 to AUC=10, AUC=2 to AUC=8, or AUC=3 to AUC=6. In some embodiments, the amount of the platinum-based agent (e.g. carboplatin) is about any of AUC=2, AUC=2.5, AUC=3, AUC=3.5, AUC=4, AUC=4.5, AUC=5, AUC=5.5, AUC=6, AUC=6.5, or AUC=7. Exemplary dosing frequencies for the administration of the platinum-based agent (e.g. carboplatin) include, but are not limited to, daily, every two days, every three days, every four days, every five days, every six days, weekly without break, three out of four weeks, once every three weeks, once every two weeks, or two out of three weeks. In some embodiments, the platinum-based agent (e.g. carboplatin) is administered about once every 2 weeks, once every 3 weeks, once every 4 weeks, once every 6 weeks, or once every 8 weeks. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosage of the platinum-based agent (e.g. carboplatin) can be between about AUC=2 to about AUC=6 (such as about any of AUC=2, AUC=3, AUC=4.5, or AUC=6) when given on a 3 week schedule, or AUC=2 to about AUC=6 (such as about any of AUC=2, AUC=3, AUC=4.5, or AUC=6) when given on a three out of four week schedule. For example, the amount of paclitaxel is about 50 mg/m$^2$ to about 125 mg/m$^2$ (e.g., about 100 mg/m$^2$) on a weekly schedule, e.g., weekly without a break. In some embodiments, the dosage of the platinum-based agent (e.g. carboplatin) can be between about AUC=2 to about AUC=6 (such as about any of AUC=2, AUC=3, AUC=4.5, or AUC=6) on a weekly schedule.

The nanoparticle composition and the platinum-based agent (e.g. carboplatin) can be administered using the same route of administration or different routes of administration. The paclitaxel nanoparticle compositions and/or the platinum-based agent (e.g. carboplatin) can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the paclitaxel nanoparticle composition and/or the platinum-based agent may be used. In some embodiments, the paclitaxel nanoparticle composition and/or the platinum-based agent (e.g. carboplatin) is administered intravenously. In some embodiments, the paclitaxel nanoparticle composition and the platinum-based agent (e.g. carboplatin) are administered intravenously. In some embodiments, the paclitaxel nanoparticle composition and/or the platinum-based agent (e.g. carboplatin) is administered intraportally. In some embodiments, the paclitaxel nanoparticle composition and/or the platinum-based agent (e.g. carboplatin) is administered intraarterially. In some embodiments, the paclitaxel nanoparticle composition and/or the platinum-based agent (e.g. carboplatin) is administered intraperitoneally. In some embodiments, the paclitaxel nanoparticle composition and/or the platinum-based agent (e.g. carboplatin) is administered by inhalation.

In some embodiments, the paclitaxel nanoparticle composition and the platinum-based agent (e.g. carboplatin) are administered simultaneously. When the drugs are administered simultaneously, the paclitaxel in the nanoparticles and the platinum-based agent contained in the same composition (e.g., a composition comprising both the nanoparticles and the platinum-based agent) or in separate compositions (e.g., the nanoparticles are contained in one composition and the platinum-based agent (e.g. carboplatin) is contained in another composition).

In some embodiments, the paclitaxel nanoparticle composition and the platinum-based agent (e.g. carboplatin) are administered sequentially. Either the paclitaxel nanoparticle composition or the platinum-based agent (e.g. carboplatin) may be administered first. The paclitaxel nanoparticle composition and the platinum-based agent (e.g. carboplatin) are contained in separate compositions, which may be contained in the same or different packages.

In some embodiments, the administration of the paclitaxel nanoparticle composition and the platinum-based agent (e.g. carboplatin) are concurrent, i.e., the administration period of the nanoparticle composition and that of the platinum-based agent (e.g. carboplatin) overlap with each other. In some embodiments, the paclitaxel nanoparticle composition is administered for at least one cycle (for example, at least any of 2, 3, or 4 cycles) prior to the administration of the platinum-based agent. In some embodiments, the platinum-based agent (e.g. carboplatin) is administered for at least any of one, two, three, or four weeks. In some embodiments, the administrations of the paclitaxel nanoparticle composition and the platinum-based agent (e.g. carboplatin) are initiated at about the same time (for example, within any one of 1, 2, 3, 4, 5, 6, or 7 days). In some embodiments, the administrations of the paclitaxel nanoparticle composition and the platinum-based agent (e.g. carboplatin) are terminated at about the same time (for example, within any one of 1, 2, 3, 4, 5, 6, or 7 days). In some embodiments, the administration of the platinum-based agent (e.g. carboplatin) continues (for example for about any one of 1, 2, 3, 4, 5, 6, 7, 8, 9, 10, 11, or 12 months) after the termination of the administration of the paclitaxel nanoparticle composition. In some embodiments, the administration of the platinum-based agent (e.g. carboplatin) is initiated after (for example after about any one of 1, 2, 3, 4, 5, 6, 7, 8, 9, 10, 11, or 12 months) the initiation of the administration of the paclitaxel nanoparticle composition. In some embodiments, the administrations of the paclitaxel nanoparticle composition and the platinum-based agent (e.g. carboplatin) are initiated and terminated at about the same time. In some embodiments, the administrations of the paclitaxel nanoparticle composition and the platinum-based agent (e.g. carboplatin) are initiated at about the same time and the administration of the platinum-based agent (e.g. carboplatin) continues (for example for about any one of 1, 2, 3, 4, 5, 6, 7, 8, 9, 10, 11, or 12 months) after the termination of the administration of the paclitaxel nanoparticle composition. In some embodiments, the administration of the paclitaxel nanoparticle composition and the platinum-based agent (e.g. carboplatin) stop at about the same time and the administration of the platinum-based agent (e.g. carboplatin) is initiated after (for example after about any one of 1, 2, 3, 4, 5, 6, 7, 8, 9, 10, 11, or 12 months) the initiation of the administration of the paclitaxel nanoparticle composition.

In some embodiments, the administration of the paclitaxel nanoparticle composition and the platinum-based agent (e.g. carboplatin) are non-concurrent. For example, in some embodiments, the administration of the paclitaxel nanoparticle composition is terminated before the platinum-based agent (e.g. carboplatin) is administered. In some embodiments, the administration of the platinum-based agent (e.g. carboplatin) is terminated before the paclitaxel nanoparticle composition is administered. The time period between these two non-concurrent administrations can range from about two to eight weeks, such as about four weeks.

The dosing frequency of the platinum-based agent (e.g. carboplatin) can be the same or different from that of the paclitaxel nanoparticle composition. The dosing frequency of the paclitaxel-containing nanoparticle composition and the platinum-based agent (e.g. carboplatin) may be adjusted over the course of the treatment, based on the judgment of the administering physician. When administered separately, the paclitaxel nanoparticle composition and the platinum-based agent (e.g. carboplatin) can be administered at different dosing frequency or intervals. For example, the paclitaxel nanoparticle composition can be administered weekly, while the platinum-based agent (e.g. carboplatin) can be administered more or less frequently. In some embodiments, sustained continuous release formulation of the drug-containing nanoparticle and/or the platinum-based agent may be used. Various formulations and devices for achieving sustained release are known in the art. A combination of the administration configurations described herein can also be used.

In some embodiments, the dosage of paclitaxel in nanoparticle composition is between about 50 mg/m$^2$ to about 125 mg/m$^2$ and the dosage of platinum-based agent (e.g. carboplatin) is between about AUC=2 to about AUC=6. In some embodiments, the dosage of paclitaxel in nanoparticle composition is between about 50 mg/m$^2$ to about 125 mg/m$^2$ weekly and the dosage of platinum-based agent (e.g. carboplatin) is between about AUC=2 to about AUC=6 once every three weeks. In some embodiments, the dosage of paclitaxel in nanoparticle composition is about 100 mg/m$^2$ weekly and the dosage of platinum-based agent (e.g. carboplatin) is about AUC=6 once every three weeks. In some embodiments, the dosage of paclitaxel in nanoparticle composition is about 75 mg/m$^2$ weekly and the dosage of platinum-based agent (e.g. carboplatin) is about AUC=4.5 once every three weeks. In some embodiments, the dosage of paclitaxel in nanoparticle composition is about 50 mg/m$^2$ weekly and the dosage of platinum-based agent (e.g. carboplatin) is about AUC=3 once every three weeks. In some embodiments, the paclitaxel nanoparticle composition and/or the platinum-based agent (e.g. carboplatin) is administered intravenously. In some embodiments, the paclitaxel nanoparticle composition and the platinum-based agent (e.g. carboplatin) are administered intravenously. In some embodiments, the platinum-based agent is carboplatin.

The doses required for paclitaxel and/or the platinum-based agent (e.g. carboplatin) may (but not necessarily) be lower than what is normally required when each agent is administered alone. Thus, in some embodiments, a subtherapeutic amount of the drug in the nanoparticle composition and/or the platinum-based agent is administered. "Subtherapeutic amount" or "subtherapeutic level" refer to an amount that is less than the therapeutic amount, that is, less than the amount normally used when the drug in the nanoparticle composition and/or the platinum-based agent (e.g. carboplatin) are administered alone. The reduction may be reflected in terms of the amount administered at a given administration and/or the amount administered over a given period of time (reduced frequency).

In some embodiments, enough the platinum-based agent (e.g. carboplatin) is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough paclitaxel in the nanoparticle composition is administered so as to allow reduction of the normal dose of the platinum-based agent (e.g. carboplatin) required to affect the same degree of treatment by at least about any of 5%, 10%, 20%, 30%, 50%, 60%, 70%, 80%, 90%, or more.

In some embodiments, the dose of both paclitaxel in the nanoparticle composition and the platinum-based agent are reduced as compared to the corresponding normal dose of each when administered alone. In some embodiments, both paclitaxel in the nanoparticle composition and the platinum-based agent are administered at a subtherapeutic, i.e., reduced, level. In some embodiments, the dose of the nanoparticle composition and/or the platinum-based agent is substantially less than the established maximum toxic dose (MTD). For example, the dose of the nanoparticle composition and/or the platinum-based agent is less than about 50%, 40%, 30%, 20%, or 10% of the MTD.

In some embodiments of any of the methods, the methods further include administration of an effective amount of an anti-angiogenic agent. In some embodiments, the anti-angiogenic agent is bevacizumab, sunitinib, or sorafenib tosylate. In some embodiments, the anti-angiogenic agent is bevacizumab. In some embodiments, the effective amount of bevacizumab is between about 5 mg/kg and about 15 mg/kg. In some embodiments, the effective amount of bevacizumab is about any of 5 mg/kg, 7.5 mg/kg, 10 mg/kg, or 15 mg/kg.

A combination of the administration configurations described herein can be used. The combination therapy methods described herein may be performed alone or in conjunction with another therapy, such as chemotherapy, radiation therapy, surgery, hormone therapy, gene therapy, immunotherapy, chemoimmunotherapy, hepatic artery-based therapy, cryotherapy, ultrasound therapy, local ablative therapy, radiofrequency ablation therapy, photodynamic therapy, and the like. Additionally, a person having a greater risk of developing the NSCLC may receive treatments to inhibit and/or delay the development of the disease.

In some embodiments, the administration of the paclitaxel nanoparticle composition and the platinum-based agent (e.g. carboplatin) are concurrent with radiation therapy (e.g. thoracic radiation). In some embodiments, the administration of the paclitaxel nanoparticle composition is administered concurrent with radiation therapy (e.g. thoracic radiation). Radiation contemplated herein includes, for example, γ-rays, X-rays (external beam), and the directed delivery of radioisotopes to tumor cells. Other forms of DNA damaging factors are also contemplated such as microwaves and UV irradiation are also contemplated. Radiation may be given in a single dose or in a series of small doses in a dose-fractionated schedule. The amount of radiation contemplated herein ranges from about 1 Gy to about 100 Gy, including, for example, about 5 Gy to about 80 Gy, about 10 Gy to about 50 Gy, or about 10 Gy. The total dose may be applied in a fractioned regime. For example, the regime may comprise fractionated individual doses of 2 Gy. Dosage ranges for radioisotopes vary widely, and depends on the half-life of the isotope and the strength and type of radiation emitted. In some embodiments, the radiation may be performed in 25-40 (e.g., about 33) fractions by either 3D conformal or intensity-modulated techniques. In some embodiments, the dosage of paclitaxel nanoparticle composition is between about 20 mg/m$^2$ to about 60 mg/m$^2$ (e.g., 40 mg/m$^2$) weekly, the dosage of platinum-based agent (e.g. carboplatin) is between about AUC=2 to AUC=6 (e.g., AUC=2) weekly, and the dosage of thoracic radiation is between about 25 Gy to about 40 Gy (e.g., about 33 Gy) fractions by either 3D conformal or intensity-modulated techniques concurrently.

When the radiation comprises use of radioactive isotopes, the isotope may be conjugated to a targeting agent, such as a therapeutic antibody, which carries the radionucleotide to the target tissue. Suitable radioactive isotopes include, but are not limited to, astatine$^{211}$, $^{14}$carbon, $^{51}$chromium, $^{36}$chlorine, $^{57}$iron, $^{58}$cobalt, copper$^{67}$, $^{152}$Eu, gallium$^{67}$, $^{3}$hydrogen, iodine$^{123}$, iodine$^{131}$, indium$^{111}$, $^{59}$ion, $^{32}$phosphorus, rhenium$^{186}$, $^{75}$selenium, $^{35}$sulphur, technicium$^{99m}$, and/or yttrium$^{90}$.

Nanoparticle Compositions

The nanoparticle compositions described herein comprise nanoparticles comprising (in various embodiments consisting essentially of) paclitaxel (or docetaxel) and an albumin (such as human serum albumin). Nanoparticles of poorly water soluble drugs (such as paclitaxel) have been disclosed in, for example, U.S. Pat. Nos. 5,916,596; 6,506,405; 6,749,868, 6,537,579, and 7,820,788 and also in U.S. Pat. Pub. Nos. 2006/0263434, and 2007/0082838; PCT Patent Application WO08/137148, each of which is incorporated by reference in their entirety. Although the description below focuses on nanoparticle compositions comprising paclitaxel, the same also applies to nanoparticle compositions comprising docetaxel.

In some embodiments, the composition comprises nanoparticles with an average or mean diameter of no greater than about 1000 nanometers (nm), such as no greater than about any of 900 nm, 800 nm, 700 nm, 600 nm, 500 nm, 400 nm, 300 nm, 200 nm, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 nm to about 400 nm. In some embodiments, the average or mean diameter of the nanoparticles is about 40 nm to about 200 nm. In some embodiments, the nanoparticles are sterile-filterable.

In some embodiments, the nanoparticles in the composition described herein have an average diameter of no greater than about 200 nm, including for example no greater than about any one of 190 nm, 180 nm, 170 nm, 160 nm, 150 nm, 140 nm, 130 nm, 120 nm, 110 nm, 100 nm, 90 nm, 80 nm, 70 nm, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190 nm, 180 nm, 170 nm, 160 nm, 150 nm, 140 nm, 130 nm, 120 nm, 110 nm, 100 nm, 90 nm, 80 nm, 70 nm, or 60 nm. In some embodiments, at least about 50% (for example at least any one of 60%, 70%, 80%, 90%, 95%, or 99%) of the nanoparticles in the composition fall within the range of about 20 nm to about 400 nm, including for example about 20 nm to about 200 nm, about 40 nm to about 200 nm, about 30 nm to about 180 nm, and any one of about 40 nm to about 150 nm, about 50 nm to about 120 nm, and about 60 nm to about 100 nm.

In some embodiments, the albumin has sulfhydryl groups that can form disulfide bonds. In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprise paclitaxel coated with an albumin (e.g., human serum albumin). In some embodiments, the composition comprises paclitaxel in both nanoparticle and non-nanoparticle forms, wherein at least about any one of 50%, 60%, 70%, 80%, 90%, 95%, or 99% of paclitaxel in the composition are in nanoparticle form. In some embodiments, paclitaxel in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of paclitaxel that is substantially free of polymeric materials (such as polymeric matrix).

In some embodiments, the composition comprises albumin in both nanoparticle and non-nanoparticle portions of the composition, wherein at least about any one of 50%, 60%, 70%, 80%, 90%, 95%, or 99% of the albumin in the composition are in non-nanoparticle portion of the composition.

In some embodiments, the weight ratio of albumin (such as human serum albumin) and paclitaxel in the nanoparticle composition is about 18:1 or less, such as about 15:1 or less, for example about 10:1 or less. In some embodiments, the weight ratio of albumin (such as human serum albumin) and paclitaxel in the composition falls within the range of any one of about 1:1 to about 18:1, about 2:1 to about 15:1, about 3:1 to about 13:1, about 4:1 to about 12:1, or about 5:1 to about 10:1. In some embodiments, the weight ratio of albumin and paclitaxel in the nanoparticle portion of the composition is about any one of 1:2, 1:3, 1:4, 1:5, 1:6, 1:7, 1:8, 1:9, 1:10, 1:11, 1:12, 1:13, 1:14, 1:15, or less. In some embodiments, the weight ratio of the albumin (such as human serum albumin) and paclitaxel in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, or about 1:1 to about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises human serum albumin. Human serum albumin (HSA) is a highly soluble globular protein of $M_r$ 65 K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context).

Human serum albumin (HSA) has multiple hydrophobic binding sites (a total of eight for fatty acids, an endogenous ligand of HSA) and binds a diverse set of taxanes, especially neutral and negatively charged hydrophobic compounds (Goodman et al., *The Pharmacological Basis of Therapeutics*, $9^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Paclitaxel has been shown to bind HSA (see, e.g., Paal et al., *Eur. J. Biochem.*, 268(7), 2187-91 (200a)).

The albumin (such as human serum albumin) in the composition generally serves as a carrier for paclitaxel, i.e., the albumin in the composition makes paclitaxel more readily suspendable in an aqueous medium or helps maintain the suspension as compared to compositions not comprising an albumin. This can avoid the use of toxic solvents (or surfactants) for solubilizing paclitaxel, and thereby can reduce one or more side effects of administration of paclitaxel into an individual (such as a human). Thus, in some embodiments, the composition described herein is substantially free (such as free) of surfactants, such as polyoxyethylated castor oil (including the product sold under the trademark CREMOPHOR EL® (BASF)). In some embodiments, the nanoparticle composition is substantially free (such as free) of surfactants. A composition is "substantially free of polyoxyethylated castor oil, sold under the trademark CREMOPHOR®" or "substantially free of surfactant" if the amount of polyoxyethylated castor oil, sold under the trademark CREMOPHOR® or surfactant in the composition is not sufficient to cause one or more side effect(s) in an individual when the nanoparticle composition is administered to the individual. In some embodiments, the nanoparticle composition contains less than about any one of 20%, 15%, 10%, 7.5%, 5%, 2.5%, or 1% organic solvent or surfactant.

The amount of albumin in the composition described herein will vary depending on other components in the composition. In some embodiments, the composition comprises an albumin in an amount that is sufficient to stabilize paclitaxel in an aqueous suspension, for example, in the form of a stable colloidal suspension (such as a stable suspension of nanoparticles). In some embodiments, the albumin is in an amount that reduces the sedimentation rate of paclitaxel in an aqueous medium. For particle-containing compositions, the amount of the albumin also depends on the size and density of nanoparticles of paclitaxel.

Paclitaxel is "stabilized" in an aqueous suspension if it remains suspended in an aqueous medium (such as without visible precipitation or sedimentation) for an extended period of time, such as for at least about any of 0.1 hours, 0.2 hours, 0.25 hours, 0.5 hours, 1 hour, 2 hours, 3 hours, 4 hours, 5 hours, 6 hours, 7 hours, 8 hours, 9 hours, 10 hours, 11 hours, 12 hours, 24 hours, 36 hours, 48 hours, 60 hours, or 72 hours. The suspension is generally, but not necessarily, suitable for administration to an individual (such as human). Stability of the suspension is generally (but not necessarily) evaluated at a storage temperature (such as room temperature (such as 20° C. –25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the albumin is present in an amount that is sufficient to stabilize paclitaxel in an aqueous suspension at a certain concentration. For example, the concentration of paclitaxel in the composition is about 0.1 mg/ml to about 100 mg/ml, including for example any of about 0.1 mg/ml to about 50 mg/ml, about 0.1 mg/ml to about 20 mg/ml, about 1 mg/ml to about 10 mg/ml, about 2 mg/ml to about 8 mg/ml, about 4 mg/ml to about 6 mg/ml, about 5 mg/ml. In some embodiments, the concentration of paclitaxel is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as polyoxyethylated castor oil, sold under the trademark CREMOPHOR®), so that the composition is free or substantially free of surfactant (such as polyoxyethylated castor oil, sold under the trademark CREMOPHOR®).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of albumin. In some embodiments, the composition, in liquid form, comprises about 0.5% to about 5% (w/v) of albumin.

In some embodiments, the weight ratio of albumin, e.g., albumin, to paclitaxel in the nanoparticle composition is such that a sufficient amount of paclitaxel binds to, or is transported by, the cell. While the weight ratio of albumin to paclitaxel will have to be optimized for different albumin and paclitaxel combinations, generally the weight ratio of albumin, e.g., albumin, to paclitaxel (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to paclitaxel weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the weight ratio of the albumin (such as human serum albumin) and paclitaxel in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, or about 1:1 to about 1:1.

In some embodiments, the albumin allows the composition to be administered to an individual (such as human) without significant side effects. In some embodiments, the albumin (such as human serum albumin) is in an amount that is effective to reduce one or more side effects of administration of paclitaxel to a human. The term "reducing one or more side effects of administration of paclitaxel" refers to reduction, alleviation, elimination, or avoidance of one or more undesirable effects caused by paclitaxel, as well as side effects caused by delivery vehicles (such as solvents that render paclitaxel suitable for injection) used to deliver paclitaxel. In some embodiments, the one or more side effects are adverse side effects (AEs). In some embodiments, the one or more side effects are serious adverse side effects (SAEs). Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with paclitaxel can be reduced.

In some embodiments, the nanoparticle compositions described herein comprises nanoparticles comprising a taxane (such as paclitaxel) and an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) and an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) and an albumin (such as human albumin or human serum albumin), wherein the nanoparticles have an average diameter of about 130 nm. In some embodiments, the nanoparticle compositions described herein comprises nanoparticles comprising paclitaxel and human albumin (such as human serum albumin), wherein the nanoparticles have an average diameter of about 130 nm.

In some embodiments, the nanoparticle compositions described herein comprises nanoparticles comprising a taxane (such as paclitaxel) and an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) and an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) and an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel and human albumin (such as human serum albumin), wherein the nanoparticles have an average diameter of about 130 nm, wherein the weight ratio of albumin and the taxane in the composition is about 9:1.

In some embodiments, the nanoparticle compositions described herein comprises nanoparticles comprising a taxane (such as paclitaxel) coated with an albumin (such as human albumin or human serum albumin). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) coated with an albumin (such as human albumin or human serum albumin), wherein the nanoparticles have an average diameter of about 130 nm. In some embodiments, the nanoparticle compositions described herein comprises nanoparticles comprising paclitaxel coated with human albumin (such as human serum albumin), wherein the nanoparticles have an average diameter of about 130 nm.

In some embodiments, the nanoparticle compositions described herein comprises nanoparticles comprising a taxane (such as paclitaxel) coated with an albumin (such as human albumin or human serum albumin), wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel coated with human albumin (such as human serum albumin), wherein the nanoparticles have an average diameter of about 130 nm, wherein the weight ratio of albumin and the taxane in the composition is about 9:1.

In some embodiments, the nanoparticle compositions described herein comprises nanoparticles comprising a taxane (such as paclitaxel) stabilized by an albumin (such as human albumin or human serum albumin). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) stabilized by an albumin (such as human albumin or human serum albumin), wherein the nanoparticles have an average diameter of about 130 nm. In some embodiments, the nanoparticle compositions described herein comprises nanoparticles comprising paclitaxel stabilized by human albumin (such as human serum albumin), wherein the nanoparticles have an average diameter of about 130 nm.

In some embodiments, the nanoparticle compositions described herein comprises nanoparticles comprising a taxane (such as paclitaxel) stabilized by an albumin (such as human albumin or human serum albumin), wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel stabilized by human albumin (such as human serum albumin), wherein the nanoparticles have an average diameter of about 130 nm, wherein the weight ratio of albumin and the taxane in the composition is about 9:1.

In some embodiments, the nanoparticle composition comprises the albumin stabilized nanoparticle formulation of paclitaxel sold under the trademark ABRAXANE® (Nab-paclitaxel). In some embodiments, the nanoparticle composition is the albumin stabilized nanoparticle formulation of paclitaxel sold under the trademark ABRAXANE® (Nab-paclitaxel). The albumin stabilized nanoparticle formulation of paclitaxel sold under the trademark ABRAXANE® is a formulation of paclitaxel stabilized by human albumin USP, which can be dispersed in directly injectable physiological solution. When dispersed in a suitable aqueous medium such as 0.9% sodium chloride injection or 5% dextrose injection, the albumin stabilized nanoparticle formulation of paclitaxel sold under the trademark ABRAXANE® forms a stable colloidal suspension of paclitaxel. The weight ratio of human albumin and paclitaxel in the composition is about 9:1. The mean particle size of the nanoparticles in the colloidal suspension is about 130 nanometers. Since HSA is freely soluble in water, the albumin stabilized nanoparticle formulation of paclitaxel sold under the trademark ABRAXANE® can be reconstituted in a wide range of concentrations ranging from dilute (0.1 mg/ml paclitaxel) to concentrated (20 mg/ml paclitaxel), including for example about 2 mg/ml to about 8 mg/ml, about 5 mg/ml.

Methods of making nanoparticle compositions are known in the art. For example, nanoparticles containing paclitaxel and albumin (such as human serum albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579, and 7,820,788 and also in U.S. Pat. Pub. No. 2007/0082838, 2006/0263434 and PCT Application WO08/137148.

Briefly, paclitaxel is dissolved in an organic solvent, and the solution can be added to an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

Other Components in the Nanoparticle Compositions

The nanoparticles described herein can be present in a composition that includes other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596 and 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits, Medicines, and Compositions

The invention also provides kits, medicines, compositions, and unit dosage forms for use in any of the methods described herein.

Kits of the invention include one or more containers comprising paclitaxel-containing nanoparticle compositions (or unit dosage forms and/or articles of manufacture) and/or the platinum-based agent, and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) a composition comprising nanoparticles comprising paclitaxel and an albumin (such as human serum albumin), b) an effective amount of the platinum-based agent, and c) instructions for administering the nanoparticle composition and the platinum-based agents for treatment of NSCLC. The nanoparticles and the platinum-based agent can be present in separate containers or in a single container. For example, the kit may comprise one distinct composition or two or more compositions wherein one composition comprises nanoparticles and one composition comprises the platinum-based agent.

The kits of the invention are in suitable packaging. Suitable packaging include, but is not limited to, vials, bottles, jars, flexible packaging (e.g., polyethylene terephthalate, sold under the trademark MYLAR® or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the paclitaxel nanoparticle compositions and platinum-based agent (e.g. carboplatin) generally include information as to dosage, dosing schedule, and route of administration for the intended treatment. In some embodiments, the instructions indicate that a dosage between about 50 mg/m$^2$ to about 125 mg/m$^2$ of paclitaxel nanoparticle composition and the dosage between about AUC=2 to about AUC=6 of platinum-based agent (e.g. carboplatin) should be administered. In some embodiments, the instructions indicate a dosage between about 50 mg/m$^2$ to about 125 mg/m$^2$ of paclitaxel nanoparticle composition weekly administered and a dosage between about AUC=2 to about AUC=6 of platinum-based agent (e.g. carboplatin) administered once every three weeks should be used for the intended treatment. In some embodiments, the instructions indicate a dosage of about 100 mg/m$^2$ of paclitaxel nanoparticle composition weekly administered and a dosage of about AUC=6 of platinum-based agent (e.g. carboplatin) administered once every three weeks should be used for the intended treatment. In some embodiments, the instructions indicate a dosage of about 75 mg/m$^2$ of paclitaxel nanoparticle composition weekly administered and the dosage of AUC=4.5 of platinum-based agent (e.g. carboplatin) administered once every three weeks should be used for the intended treatment. In some embodiments, the instructions indicate a dosage of about 50 mg/m$^2$ of paclitaxel nanoparticle composition weekly and the dosage of about AUC=3 of platinum-based agent (e.g. carboplatin) administered once every three weeks should be used for the intended treatment. In some embodiments, the instructions indicate a dosage of between about 20 mg/m$^2$ to about 60 mg/m$^2$ (e.g., 40 mg/m$^2$) of paclitaxel nanoparticle composition administered weekly, a dosage between about AUC=2 to AUC=6 (e.g., AUC=2) of platinum-based agent (e.g. carboplatin) administered weekly, and a dosage of between about 25 Gy to about 40 Gy (e.g., about 33 Gy) fractions of thoracic radiation by either 3D conformal or intensity-modulated techniques concurrently. In some embodiments, the instructions indicate that paclitaxel nanoparticle composition and/or the platinum-based agent (e.g. carboplatin) is administered intravenously. In some embodiments, the instructions indicate that paclitaxel nanoparticle composition and the platinum-based agent (e.g. carboplatin) are administered intravenously. In some embodiments, the instructions indicate that the platinum-based agent is carboplatin.

In some embodiments, the kit provides a label denoting (i.e., indicating) that the paclitaxel nanoparticle composition and the platinum-based agent are indicated for treating individuals having one or more characteristics of (i) has diabetes, (ii) has four or more metastatic sites, and/or (iii) is at least about 70 years old. In some embodiments, the label further denotes that the paclitaxel nanoparticle composition and the platinum-based agent are indicated for treating NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

The containers may be unit doses, bulk packages (e.g., multi-dose packages) or sub-unit doses. For example, kits may be provided that contain sufficient dosages of paclitaxel as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more.

Kits may also include multiple unit doses of paclitaxel and pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. In some embodiments, there is provided a medicine (or composition or a unit dosage form) for use in treating NSCLC in conjunction with the platinum-based agent, comprising nanoparticles comprising paclitaxel and an albumin (such as human serum albumin). In some embodiments, there is provided a medicine (or composition or a unit dosage form) for use in treating NSCLC, comprising nanoparticles comprising paclitaxel and an albumin (such as human serum albumin) and the platinum-based agent.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

ADDITIONAL EXEMPLARY EMBODIMENTS

The present application in some embodiments provides a method of treating NSCLC in an individual comprising administering to the individual a) an effective amount of a composition comprising nanoparticles comprising paclitaxel and an albumin and b) an effective amount of a platinum-based agent, wherein treatment is based upon the individual having one or more characteristics of (i) having diabetes, (ii) having four or more metastatic sites, and (iii) is at least about 70 years old.

In some embodiments according to (or as applied to) any of any of the embodiments above, the treatment is based upon the individual having diabetes.

In some embodiments according to (or as applied to) any of any of the embodiments above, the treatment is based on the individual having four or more metastatic sites.

In some embodiments according to (or as applied to) any of any of the embodiments above, the treatment is based on the individual being at least about 70 years old.

In some embodiments according to (or as applied to) any of any of the embodiments above, the method comprises selecting the individual for treatment based on one or more characteristics of (i) having diabetes, (ii) having four or more metastatic sites, and (iii) is at least about 70 years old.

In some embodiments according to (or as applied to) any of any of the embodiments above, the method comprises selecting the individual for treatment based on the individual having diabetes.

In some embodiments according to (or as applied to) any of any of the embodiments above, the method comprises selecting the individual for treatment based on the individual having four or more metastatic sites.

In some embodiments according to (or as applied to) any of any of the embodiments above, the method comprises selecting the individual for treatment based on the individual being at least about 70 years old.

In some embodiments according to (or as applied to) any of any of the embodiments above, the treatment is based on the individual having squamous cell carcinoma.

In some embodiments according to (or as applied to) any of any of the embodiments above, the dose of paclitaxel in the composition comprising nanoparticles comprising paclitaxel and albumin is between about 50 mg/m$^2$ and about 125 mg/m$^2$.

In some embodiments according to (or as applied to) any of any of the embodiments above, the composition comprising nanoparticles comprising paclitaxel and albumin is administered weekly.

In some embodiments according to (or as applied to) any of any of the embodiments above, the effective amount of the platinum-based agent is between about AUC=2 and about AUC=6.

In some embodiments according to (or as applied to) any of any of the embodiments above, the platinum-based agent is administered once every three weeks.

In some embodiments according to (or as applied to) any of any of the embodiments above, the dose of paclitaxel in the composition comprising nanoparticles comprising paclitaxel and albumin is 100 mg/m$^2$ administered weekly and the effective amount of the platinum-based agent is AUC=6 administered once every three weeks.

In some embodiments according to (or as applied to) any of any of the embodiments above, the paclitaxel in the nanoparticles is coated with albumin.

In some embodiments according to (or as applied to) any of any of the embodiments above, the nanoparticles in the composition have an average diameter of no greater than about 200 nm.

In some embodiments according to (or as applied to) any of any of the embodiments above, the NSCLC is Stage IIIB NSCLC or Stage IV NSCLC.

In some embodiments according to (or as applied to) any of any of the embodiments above, the composition comprising nanoparticles comprising paclitaxel and albumin and the platinum-based agent are administered parenterally.

In some embodiments according to (or as applied to) any of any of the embodiments above, the composition comprising nanoparticles comprising paclitaxel and albumin and the platinum-based agent are administered intravenously.

In some embodiments according to (or as applied to) any of any of the embodiments above, the platinum-based agent is carboplatin.

In some embodiments according to (or as applied to) any of any of the embodiments above, the individual is human.

EXAMPLES

Example 1. A Randomized, Phase III Trial of Nab-Paclitaxel and Carboplatin Compared with Paclitaxel Dissolved in Polyoxyethylated Castor Oil and Dehydrated Alcohol, Sold Under the Trademark TAXOL® and Carboplatin as First-Line Therapy in Patients with Advanced Non-Small Cell Lung Cancer (NSCLC)

The clinical study compared disease response (using RECIST guidelines) of Nab-paclitaxel plus carboplatin (AUC=6) vs. paclitaxel dissolved in polyoxyethylated castor oil and dehydrated alcohol, sold under the trademark TAXOL® and carboplatin (AUC=6) as first-line therapy in patients with advanced NSCLC. The clinical study also compared the frequency of toxicities grades using the Common Terminology Criteria for Adverse Events (CTCAE); progression-free survival (PFS); patient survival; duration of response in responding patients; evaluated pharmacokinetic parameters; and evaluated secreted protein acidic and rich in cysteine (SPARC) and other molecular biomarkers in tumor tissue and peripheral blood and determine their possible correlation with efficacy outcomes.

Treatment Design

This was a controlled, randomized, multicenter, Phase III study designed to evaluate the safety/tolerability and anti-tumor effect of intravenously administered Nab-paclitaxel/carboplatin combination therapy compared to that of paclitaxel dissolved in polyoxyethylated castor oil and dehydrated alcohol, sold under the trademark TAXOL®/carboplatin combination therapy as first-line therapy in patients with NSCLC. Patients were randomized into one of two treatment arms.

Baseline evaluations were performed for all patients to determine study eligibility. These evaluations were completed within 28 days of randomization The following clinical evaluations were performed at baseline including: a) medical history (including specific information regarding any prior therapy and cardiac abnormality); b) serum β-hCG pregnancy test (for women of childbearing-potential only) was conducted to determine patient eligibility within 72 hours of the first administration of study drug; c) 12-lead electrocardiogram (ECG); d) collection of blood samples for evaluation of molecular biomarkers; e) computed tomography (CT) scan of chest, liver, and abdomen and any other studies required for tumor imaging; f) a nuclear medicine bone scan were performed at baseline for any patient with clinical symptoms of possible bone metastases; g) CT scan of head or brain magnetic resonance imaging (MRI) (if symptomology of brain metastasis exist); h) height, weight, and calculation of body surface area (BSA; i) physical examination and ECOG (Zubrod) performance status scale; j) concomitant medication evaluation (only medications taken within 30 days before the baseline visit were recorded); k) peripheral neuropathy assessment (physician and patient assessments); l) vital signs; m) complete blood count (CBC), differential, and platelet counts; and n) clinical chemistry panel (minimally including serum transaminases, bilirubin, alkaline phosphatases, glucose, blood urea nitrogen (BUN), and creatinine). The same mode of imaging was used at baseline and throughout the study. CT image preparation followed the specifications provided in the RECIST guidelines.

Treatment Phase Evaluations—

Patients returned within 7 days of randomization to begin Cycle 1 of study drug dosing. Visits where response assessments were not performed occurred within ±2 days of the planned visit date. Response assessments were performed every 6 weeks, at any time during the 6th week. If a dose was missed due to toxicity during a cycle, that dose was not to be made up and was to be recorded as a missed dose.

The following evaluations were performed prior to dosing or on Day 1 of each cycle including: a) physical examination (on Day 1 of each cycle or within 1 week prior to Day 1 of each cycle) and ECOG performance status scale; b) collection of blood samples for evaluation of molecular biomarkers (Day 1 of Cycles 3, 5, 7, etc.); c) weight; d) concomitant medications evaluation; e) peripheral neuropathy assessment (on Day 1 of each cycle or within 1 week prior to Day 1 of each cycle); f) vital signs; g) adverse event evaluation (each dose); h) CBC, differential, and platelet counts; and i) clinical chemistry panel (minimally including serum transaminases, bilirubin, alkaline phosphatases, glucose, BUN, and creatinine).

The following evaluations were performed weekly (Days 8 and 15) during each cycle including: a) concomitant medications evaluation; b) adverse event evaluation; and c) CBC, differential, and platelet count. CT scans of the chest, liver, and abdomen and any other studies required for tumor imaging were done every 6 week while on treatment.

End-of-Study Evaluations—

An end of study evaluation was performed when treatment was completed for whatever cause. Laboratory and clinical evaluations were performed to assess adverse events at the time treatment was ended. Patients who had not developed progressive disease prior to going off treatment had tumor imaging studies performed every 6 weeks until tumor progression was documented.

End of treatment evaluations included the following: a) physical examination and ECOG performance status scale; b) CT scan of chest, liver, and abdomen and any other studies required for tumor imaging (only if required per the defined study imaging schedule); c) weight; d) concomitant medications evaluation; e) peripheral neuropathy assessment; f) vital signs; g) adverse event evaluation; h) CBC, differential, and platelet counts; and i) clinical chemistry panel (minimally including serum transaminases, bilirubin, alkaline phosphatases, glucose, BUN, creatinine).

Adverse Event (AE) Follow-Up Evaluations—

Any AE or serious adverse event (SAE) whose onset occurred between the first dose of study drug to 30 days after the last study drug or EOS (whichever is later) was collected. AE follow-up was conducted as follows: a) non-serious AEs, other than neuropathy, were followed for 30 days after the patient's last dose of study drug; b) neuropathy was followed until improvement to Grade 1 occurred, at least 3 months had elapsed without improvement or worsening, or the patient initiated any other anticancer therapy during follow-up; and c) all SAEs (regardless of relationship to study drug) were followed until resolution.

Follow-up evaluations included studies necessary to document the resolution or persistence of any unresolved AEs and included, for example: a) physical examination and ECOG performance status scale; b) CT scan of chest, liver, and abdomen and any other studies required for tumor imaging; c) weight; d) concomitant medications evaluation; e) peripheral neuropathy assessment; f) vital signs; g) AE event evaluation; and h) CBC, differential, platelet count, and clinical chemistry panel.

Post-Study Follow-Up for Patient Survival—

Patient status continued to be evaluated post-study by telephone monthly for 6 months, and then every 3 months thereafter for 12 months (total of 18 months follow-up), to obtain post-study survival data.

Withdrawal—

Patients withdrew from this study if any of the following occurred: a) progressive disease; b) development of toxicity that was unacceptable in the opinion of the investigator; c) patient declined to continue therapy; d) if, following the 2nd dose reduction, there was a recurrence of Grade 4 neutropenia, or any other hematologic toxicity that was Grade 3 or 4, or any Grade 3 or 4 nonmyelosuppressive AE, unless, at the discretion of the investigator, there was evidence of continuing benefit to the patient that outweighed the risk of recurrent toxicity; d) initiation of other anticancer therapy; or e) in the investigator's judgment, it was in the patient's best interest to discontinue the study.

A summary of the study protocol is provided in Table 1.

TABLE 1

| | | CYCLE 1, 3, 5, etc | | | CYCLE 2, 4, 6, etc. | | | Every 6 | | | Post-study Progression/ |
|---|---|---|---|---|---|---|---|---|---|---|---|
| Assessment | Baseline | Day 1 | Day 8 | Day 15 | Day 1 | Day 8 | Day 15 | Weeks | EOS[A] | AE Follow-up[B] | Survival |
| Informed Consent | X | — | — | — | — | — | — | — | — | — | — |
| Medical History | X | — | — | — | — | — | — | — | — | — | — |
| Serum β-hCG[C] | X | — | — | — | — | — | — | — | — | — | — |
| Electrocardiogram (ECG)[D] | X | — | — | — | — | — | — | — | — | — | — |
| Consent to use diagnostic tumor biopsy for SPARC analysis | X | — | — | — | — | — | — | — | — | — | — |
| Collection of blood samples for evaluation of other molecular biomarkers[E] | X | X | — | — | — | — | — | — | — | — | — |
| PK Sampling (Arm A) | — | X | — | — | — | — | — | — | — | — | — |
| CT Scan of Chest/Liver/Abdomen[F] & any other studies required for tumor imaging | X | — | — | — | — | — | — | X[G] | X[H] | — | X |
| CT Scan of Head or Brain MRI[I] | X | — | — | — | — | — | — | — | — | — | — |
| Bone Scan[J] | X | — | — | — | — | — | — | — | — | — | — |
| BSA Calculation and Height[K] | X | — | — | — | — | — | — | — | — | — | — |
| Weight | X | X | — | — | X | — | — | — | X | X | — |
| Physical Examination[L]; ECOG status | X | X | — | — | X | — | — | — | X | X | — |
| Concomitant Medication Evaluation | X | X | X | X | X | X | X | — | X | X | — |
| Peripheral Neuropathy Assessment[M] | X | X | — | — | X | — | — | — | X | X | — |
| Vital Signs | X | X | — | — | X | — | — | — | X | X | — |
| Adverse Event Evaluation | — | X | X | X | X | X | X | — | X | X | — |
| CBC Differential, Platelet Count | X | X | X | X | X | X | X | — | X | X | — |
| Clinical Chemistry Panel | X | X | — | — | X | — | — | — | X | X | — |
| Progression/Survival Follow-up[N] | — | — | — | — | — | — | — | — | — | — | X |

[A]EOS = End of Study. When patient came off study, the indicated tests were done. Repeat studies for tumor response only if required per the defined study imaging schedule.
[B]Reporting of AEs/SAEs continued through 30 days after the patient discontinued the study drug or EOS, whichever came later. Any AEs/SAEs that began during this time were followed. If there were no AEs or SAEs ongoing at the EOS visit, follow-up was done by telephone to the patient weekly until 30 days from last dose of treatment.
[C]Pregnancy test required for women of child-bearing potential only. Serum β-hCG pregnancy test was performed to assess patient eligibility within 72 hours of the first administration of study drug.
[D]ECG was performed at baseline and at any other stage in the cycle as determined to be clinically significant by investigator
[E]Sample for molecular biomarkers were obtained within 2 weeks prior to first administration of study drug (including Day 1 of Cycle 1, prior to administering study chemotherapy). All subsequent samples were collected on Day 1 of odd numbered cycles (Cycles 3, 5, 7, etc.), prior to administration of study drug.
[F]All patients had radiographically documented measurable tumor(s) by RECIST criteria: CT scan of the thorax, abdomen, and liver were performed at baseline, every 6 weeks (at any time during the 6th week) while on-treatment, and EOS (only if required per the defined study imaging schedule). The method of assessment chosen at baseline to follow tumors should remain consistent throughout study duration.
[G]Obtained scans for response assessment every 6 weeks while on-treatment.
[H]Restaging studies were also to be done at the EOS visit only if required per the defined study imaging schedule, unless there was otherwise clear clinical evidence of progression.
[I]A CT scan of head or brain MRI was performed if symptoms of brain metastasis existed.
[J]A nuclear medicine bone scan was performed at Baseline for any patient with clinical symptoms of possible bone metastases. All areas identified on the bone scan as possible metastases, which were inconclusive, then had plain film X-rays done to verify they were indeed metastases. These confirming X-ray studies were only done at Baseline, and did not need to be repeated at subsequent bone scans. Bone scans were repeated every 12 weeks and at the time an objective response was initially documented or initially confirmed.
[K]BSA was calculated at baseline and recalculated if body weight changed by more than 10% from baseline.
[L]On Day 1 of each cycle or within 1 week prior to Day 1 of each cycle.
[M]On Day 1 of each cycle or within 1 week prior to Day 1 of each cycle. The occurrence of peripheral neuropathy was reported by the investigator per protocol as an AE or SAE.
[N]Post-study follow-ups provided patient survival. Phone follow-ups were performed monthly for 6 months and every 3 months thereafter for 12 months (total of 18 months follow-up). For patients who had not yet progressed since the start of the study, progression-free survival follow-up were performed every 6 weeks by repeating studies required for tumor imaging. Bone scans were conducted every 12 weeks if being used to document non-target lesions.

Inclusion/Exclusion Criteria

A patient was eligible for inclusion in this study only if all of the following criteria were met: 1) histologically or cytologically confirmed stage IIIB or IV NSCLC; 2) male or non-pregnant and non-lactating female, and ≥18 years of age (if a female patient is of child-bearing potential, as evidenced by regular menstrual periods, she must have a negative serum pregnancy test (β human chorionic gonadotropin) documented within 72 hours of the first administration of study drug, and if sexually active, the patient must agree to utilize contraception considered adequate and appropriate by the investigator); 3) no other current active malignancy; 4) radiographically-documented measurable disease (defined by the presence of at least one radiographically documented measurable lesion); 5) patients must have received no prior chemotherapy for the treatment of metastatic disease (adjuvant chemotherapy permitted providing cytotoxic chemotherapy was completed 12 months prior to starting the study); 6) expected survival of >12 weeks; 7) ECOG performance status 0 or 1; 8) patient had the following blood counts at baseline: a) absolute neutrophil count (ANC) ≥1.5×10$^9$ cells/L; b) platelets ≥100×10$^9$ cells/L; and c) hemoglobin (Hgb) ≥9 g/dL; and 9) patient had the following blood chemistry levels at baseline: a) aspartate aminotransferase (AST)/serum glutamic oxaloacetic transaminase (SGOT), alanine aminotransferase (ALT)/serum glutamic pyruvic transaminase (SGPT) ≤2.5× upper limit of normal range (ULN) or ≤5.0×ULN if liver metastases; b) total bilirubin ≤ULN, and c) creatinine ≤1.5 mg/dL.

A patient was ineligible for inclusion in this study if any of the following criteria applied: 1) evidence of active brain metastases, including leptomeningeal involvement (prior evidence of brain metastasis permitted only if treated and stable, off therapy, for at least 1 month); 2) the only evidence of disease was non-measurable; 3) patient had pre-existing peripheral neuropathy of Grade 2, 3, or 4 (per CTCAE); 4) patient received radiotherapy in last 4 weeks, except if to a non-target lesion only (prior radiation to a target lesion was permitted only if there had been clear progression of the lesion since radiation was completed); 5) patient had a clinically significant concurrent illness; 6) patient had received treatment with any investigational drug within the previous 4 weeks; 7) patient had a history of allergy or hypersensitivity to any of the study drugs; 8) patient had serious medical risk factors involving any of the major organ systems such that the investigator considers it unsafe for the patient to receive an experimental research drug; or 9) patient was enrolled in any other clinical protocol or investigational trial that involved administration of experimental therapy and/or therapeutic devices.

Dosages and Administration

Patients with NSCLC were randomized into one of 2 treatment arms. Treatment Arm A were assigned for administration of Nab-paclitaxel/carboplatin and Treatment Arm B were assigned for the administration of paclitaxel dissolved in polyoxyethylated castor oil and dehydrated alcohol, sold under the trademark TAXOL®/carboplatin. There were approximately 525 intent-to-treat (ITT) patients per arm.

Nab-paclitaxel or paclitaxel dissolved in polyoxyethylated castor oil and dehydrated alcohol, sold under the trademark TAXOL® was administered in this study only in combination with carboplatin, i.e., no other additional chemotherapeutic agents were administered with the study drug. Patients could not participate in any other clinical protocol or investigational trial that involved administration of experimental therapy and/or the use of investigational devices with therapeutic intent while enrolled in this study.

Supportive care, such as anti-emetic and pain medications, and erythropoietin could be administered. Concurrent treatment with bisphosphonates was allowed. G-CSF was administered according to the guidelines described herein.

Patients could continue on treatment in the absence of progressive disease and unacceptable toxicity as long as their treating physician felt it was in their best interests to do so. In general, assuming adequate tolerability of the regimen, it was encouraged that patients received at least 6 cycles of treatment to permit adequate evaluation of the treatment regimen. Patients, who stopped treatment prior to developing progressive disease, were followed without further treatment until progressive disease was documented or until the treating physician felt additional treatment was required.

Treatment Arm A (Nab-Paclitaxel/Carboplatin)

During the Treatment Phase, patients randomized to this arm intravenously received Nab-paclitaxel 100 mg/m$^2$ administered weekly (Days 1, 8 and 15 of each cycle) over approximately 30 minutes without any steroid premedication and without G-CSF prophylaxis (unless modified as described herein) followed by carboplatin at AUC=6 on Day 1 of each cycle, repeated every 3 weeks. Carboplatin was intravenously infused over 30-60 minutes after the Nab-paclitaxel infusion.

A maximum of two dose reductions were allowed from the original dose: a) 1st dose reduction: Decreased Nab-paclitaxel to 75 mg/m$^2$ and carboplatin to an AUC of 4.5 (25% reduction) and b) 2nd dose reduction: Decreased to Nab-paclitaxel to 50 mg/m$^2$ and carboplatin to an AUC of 3.0 (50% reduction).

Nab-paclitaxel dosing was not administered at the start of the study or on Day 1 of a cycle until the absolute neutrophil count returned to ≥1.5×10$^9$ cells/L and the platelet count returned to ≥100×10$^9$ cells/L. For each subsequent weekly dose of Nab-paclitaxel, patients had an ANC≥0.5×10$^9$ cells/L and platelets>50×10$^9$ cells/L. If the ANC and platelets were not adequate for that week's treatment, the dose was to be held and resumed the following week, provided the ANC was ≥0.5×10$^9$ cells/L and platelets were >50×10$^9$ cells/L. Reduce subsequent dose only if criteria below were met. Nab-paclitaxel was not administered if hepatic function parameters were out of the range that was established for entry into the study.

Treatment Arm B (Paclitaxel Dissolved in Polyoxyethylated Castor Oil and Dehydrated Alcohol, Sold Under the Trademark TAXOL®/Carboplatin)

During the Treatment Phase, patients randomized to this arm intravenously received paclitaxel dissolved in polyoxyethylated castor oil and dehydrated alcohol, sold under the trademark TAXOL® 200 mg/m$^2$ administered over 3 hours with standard premedication followed by carboplatin at AUC=6, repeated every 3 weeks (both drugs given on Day 1 of each cycle). Carboplatin was infused by IV over 30-60 minutes.

A maximum of 2 dose reductions were allowed from the original dose: a) 1st dose reduction: Decreased paclitaxel dissolved in polyoxyethylated castor oil and dehydrated alcohol, sold under the trademark TAXOL® to 150 mg/m$^2$ and carboplatin to an AUC of 4.5 (25% reduction) and b) 2nd dose reduction: Decreased to paclitaxel dissolved in polyoxyethylated castor oil and dehydrated alcohol, sold under the trademark TAXOL® 100 mg/m$^2$ and carboplatin to an AUC of 3.0 (50% reduction).

Paclitaxel dissolved in polyoxyethylated castor oil and dehydrated alcohol, sold under the trademark TAXOL® and carboplatin were not administered at the start of each cycle until the absolute neutrophil count returned to >1.5×10$^9$ cells/L and the platelet count returned to >100×10$^9$ cells/L. Neither drug was administered at the beginning of a cycle if hepatic function parameters were out of the range that was established for entry into the study.

Nab-Paclitaxel

Each single-use 50 mL vial contained 100 mg paclitaxel and human albumin (HA) as a stabilizer. Each Nab-paclitaxel vial was reconstituted by using a 50 or 60 cc sterile syringe to inject 20 mL of 0.9% Sodium Chloride Injection or equivalent into each vial over a period of not less than 1 minute (5 mg/mL suspension). The use of in-line filters was generally not necessary; if used, in-line filters with pore sizes of <15 microns (15 μm) were not used.

Paclitaxel Dissolved in Polyoxyethylated Castor Oil and Dehydrated Alcohol, Sold Under the Trademark TAXOL®

See Paclitaxel dissolved in polyoxyethylated castor oil and dehydrated alcohol, sold under the trademark TAXOL® package insert (current version of Prescribing Information is provided in the Study Manual) for description and formulation. Paclitaxel dissolved in polyoxyethylated castor oil and dehydrated alcohol, sold under the trademark TAXOL® was diluted in 0.9% Sodium Chloride Injection, USP; 5% Dextrose Injection, USP; 5% Dextrose and 0.9% Sodium Chloride Injection, USP; or 5% Dextrose in Ringer's Injection to a final concentration of 0.3 to 1.2 mg/mL. Paclitaxel dissolved in polyoxyethylated castor oil and dehydrated alcohol, sold under the trademark TAXOL® was administered through an in-line filter with a microporous membrane not greater than 0.22 microns.

Carboplatin

The chemical name for carboplatin is cis-diammine(cyclobutane-1,1-dicarboxylate-O,O')platinum(II). Carboplatin lyophilized powder was reconstituted for IV infusion using the appropriate diluent and volume as directed in the package insert. Dosing of carboplatin was based on the Calvert formula: carboplatin dose (mg)=(Target AUC)×(GFR+25). For the purposes of this protocol, the GFR is considered to be equivalent to the creatinine clearance (calculated by the method of Cockcroft and Gault, 1976). To calculate dose of carboplatin (total mg, not mg/m$^2$): mg carboplatin=(6)× (CrCl+25). For obese patients, defined as having a Body Mass Index (BMI)>30 kg/m$^2$, use lean body weight in kilograms in the above formula to calculate creatinine clearance, instead of actual body weight.

Dose Modifications (All Arms)

Rules for Dose Omission—

Day 1 dose missed: If the dose held or missed was to be given on Day 1 of the next cycle, the next cycle was not considered to start until the day the first dose was actually administered to the patient (i.e., D1-D8-D15, X-D1-D8-D15, etc.). Day 8 dose was missed: Cycle continued per protocol, with one dose not given (i.e., D1-D8-D15, D1-X-D15, D1-D8-D15, etc.). Day 15 was administered as per cycle calendar if counts and chemistries permitted. Day 15 dose missed: Cycle continued per protocol, with one dose not given (i.e., D1-D8-D15, D1-D8-X, D1-D8-D15, etc.). Day 1 was administered as per cycle calendar if counts and chemistries permitted.

Hematologic Toxicity—

Study drugs were only administered if hepatic function was within the parameters established in the eligibility criteria. Hepatic toxicity from taxanes could occur but it was uncommon. Therefore, hepatic dysfunction that occurs while the patient was on study prompted an evaluation to determine the cause, including the possibility of progressive metastatic disease and hepatotoxicity from concurrent medications. The table below provided a guideline for implementing dose reductions and growth factor treatment for hematologic toxicity for both study arms:

TABLE 2

Use of G-CSF and Dose reductions for Hematologic Toxicity

| Adverse Event | Occurrence | Action to be Taken |
|---|---|---|
| ANC <500 cells/mm$^3$ (nadir count) with neutropenic fever >38° C.<br>OR<br>Delay of next cycle due to persistent neutropenia** (ANC <1500 cells/mm$^3$)<br>OR<br>Neutropenia <500 cells/mm3 for >1 week | 1$^{st}$ Occurrence | Dose reduction to the next lower level were required for subsequent cycles once ANC is ≥1500 cells/mm$^3$. |
| | 2$^{nd}$ Occurrence | Dose reduction to the next lower level were required for subsequent cycles once ANC is ≥1500 cells/mm$^3$. |
| Thrombocytopenia Grade 3 or Grade 4* | 1$^{st}$ Occurrence | Dose reduction to next lower level; initiation of next cycle is delayed until platelet count was 100,000 cells/mm$^3$. |
| | 2$^{nd}$ Occurrence | Discontinued treatment |

*See NCI CTCAE Scale for definition of Grade 3 and Grade 4 events.
**Maximum of 7 days post scheduled Day 1 dose of next cycle.

Colony Stimulating Factor Administration—

Colony stimulating factors could be given according to institutional guidelines for the treatment of neutropenic fever or infections associated with neutropenia.

Hypersensitivity Reactions—

Minor symptoms such as flushing, skin reactions, dyspnea, hypotension, or tachycardia could require temporary interruption of the infusion. However, severe reactions, such as hypotension requiring treatment, dyspnea requiring bronchodilators, angioedema or generalized urticaria required immediate discontinuation of study drug administration and aggressive symptomatic therapy. Patients who develop severe hypersensitivity reactions to any of the study drugs were not re-challenged with the drug. Treatment with the remaining drug alone continued.

Dose Reductions for Non-Hematologic Toxicity—

Table 3 provided a guideline for dose reductions for non-hematologic toxicity.

TABLE 3

Dose Reductions for Non-hematologic Toxicity

| Adverse Event | Occurrence | Action to be Taken |
| --- | --- | --- |
| Grade 2 or 3 cutaneous toxicity | 1st Occurrence | Interrupted treatment until toxicity |
| | 2nd Occurrence | improved to Grade 0 or 1. When treatment was resumed, reduced by 1 dose level. |
| | 3rd Occurrence | Discontinued treatment |
| Grade 4 cutaneous toxicity | 1st Occurrence | Discontinued treatment |
| Grade 3 mucositis or diarrhea | 1st Occurrence | Interrupted treatment until toxicity |
| | 2nd Occurrence | improved to Grade 0 or 1. When treatment was resumed, reduced by 1 dose level. |
| | 3rd Occurrence | Discontinued treatment |
| Grade 4 mucositis or diarrhea | 1st Occurrence | Discontinued treatment |
| Any other Grade 3 or 4 non-hematologic toxicity excluding alopecia | 1st Occurrence | Interrupted treatment until toxicity |
| | 2nd Occurrence | improved to Grade 0, 1 or 2.* When treatment was resumed, reduced by 1 dose level. |
| | 3rd Occurrence | Discontinue treatment |

*This decision depended upon the type of non-hematologic toxicity seen and which course was medically most sound in the judgment of the physician investigator.

Peripheral Neuropathy—

Treatment was withheld in patients who experienced ≥Grade 3 peripheral neuropathy. Treatment could resume at the next lower dose level (see Dose Reductions above) in subsequent cycles after the peripheral neuropathy improves to ≤Grade 1. The time to resolution to Grade ≤1 was the adverse event duration used for adverse event reporting.

Cutaneous Toxicity—

Patients who developed Grade 2 or 3 cutaneous toxicity had their dose reduced by 1 dose level. If the patient continued to experience these reactions, despite dose reduction, treatment was discontinued. Patients who develop Grade 4 cutaneous toxicity had treatment discontinued.

Gastrointestinal Toxicity—

If Grade 3 mucositis or diarrhea occurred, study drug was withheld until resolution to ≤Grade 1, then reinstituted at the next lower dose level (see Dose Reductions). Patients who develop Grade 4 mucositis or diarrhea had treatment discontinued.

Other Toxicities—

If toxicities were ≤Grade 2, the toxicity was managed symptomatically if possible, and the patient re-treated without dose reduction. If toxicities were ≥Grade 3, treatment was withheld until resolution to Grade 0, 1 or 2, or baseline if baseline was greater than Grade 1, then reinstituted, if medically appropriate, at the next lower dose level (see Dose Reductions). Recurrence of a Grade 3 or 4 toxicity following 2 dose reductions necessitated discontinuation of treatment.

Dose Delays—

Patients whose next treatment was delayed for ≥3 weeks due to persistent toxicity had subsequent doses reduced by 1 dose level.

Discontinuation from Study—

If an adverse event that required dose reduction recurred after the dose had been reduced twice, the patient generally had treatment discontinued unless, at the discretion of the investigator, there was evidence of continuing benefit to the patient that outweighed the risk of recurrent toxicity.

Efficacy Endpoints

The primary efficacy endpoint was the percentage of patients who achieve an objective confirmed complete or partial response based on the blinded radiological review using RECIST response guidelines. Key secondary efficacy endpoints included a) progression tree survival (PFS); b) patient survival; c) percentage of patients with stable disease for ≥16 weeks or confirmed complete or partial response (i.e., disease control rate); d) duration of response in responding patients; and e) correlation of SPARC and other molecular biomarkers with efficacy outcomes.

Tumors were assessed in the study by imaging studies every 6 weeks during therapy (at any time during the 6th week). For patients who have not progressed by end-of-treatment, repeat imaging was performed every 6 weeks until tumor progression is documented. Secondary analyses included progression-free survival, duration of response in responding patients, disease control rate and patient survival. Safety and tolerability were monitored through reporting of adverse events and serious adverse events, laboratory abnormalities, and incidence of patients experiencing dose modifications, dose interruptions, and/or premature discontinuation of study drug. Patients were considered responders if they achieved an objective complete or partial response according to RECIST guidelines. Patients who discontinue early from the study or who are randomized but do not receive treatment were not replaced.

Measurable and Non-Measurable Lesion

The definition of a measurable lesion at baseline was dependent on the technical factors of the imaging studies that were used to evaluate the patient. The recommendations for the imaging parameters were based on the American College of Radiology (ACR) Practice Guidelines and Technical Standards. The proposal for modifying the size of measurable lesions at baseline to two (2) times the reconstruction interval of the baseline/screening studies was consistent with the RECIST definition for a measurable lesion. Lesions that could be accurately measured in at least one (1) dimension with the longest diameter (LD)≥twenty (20) mm with conventional techniques when the conventional scans were performed with a reconstruction interval of ten (10) mm or less were measurable lesions. Lesions that could be accurately measured in at least one (1) dimension with the longest diameter (LD) being two (2) times the reconstruction interval (RI) of the spiral CT scan. The minimum size of a measurable lesion is ten (10) mm. The definition for target disease did not change and was determined on the basis of the baseline scan.

All other lesions that did not meet the criteria for measurable disease as described above as well as other truly non-measurable lesions, were considered non-measurable.

Target and Non-Target Lesion Response

Response at each time point was assessed as a combination of the target and non-target responses as well as the presence of new lesions.

Up to ten (10) target lesions, a maximum of five (5) per organ, were chosen for measurement over the course of the study. The distribution of these target lesions was representative of the subject's overall disease. Target lesions were not chosen from a previously irradiated area unless lesions in those areas had documented progression. Target lesions were measurable at baseline. For any target lesion at any time point, measurements were taken and recorded unidimensionally. The longest dimension of each target lesion was measured and recorded. The longest dimension of the target lesions was summed to obtain the Sum of the Longest Diameters (SLD). The baseline SLD was used as reference to further characterize the objective tumor response of the target lesions. For the consideration of progressive disease, the nadir of the SLD for the target lesions was used as reference.

For cases where there was no target lesion identified, tumor assessment for progression was done based on non-target lesion assessments or the development of new lesions. Response (PR or CR) and SD was not assessed in subjects where target lesions were not identified at baseline.

The following conventions were applied in selecting target lesions in patients who have received prior radiation therapy: a) prior axillary radiation (i.e., prior radiation history including the term "axilla", "axillary" or other related term(s)) did not preclude the selection of measurable lesions in the chest wall or thorax as target lesions); b) prior breast (i.e., prior radiation history including the term "breast") or chest wall radiation (i.e., prior radiation history including the term "chest wall" or other related term(s)) precluded the selection of chest wall lesions as target disease for chest wall lesions ipsilateral to the site of the chest wall radiation; c) prior bone radiation (e.g., vertebral, rib, pelvis, femur, etc.) did not preclude the selection of measurable lesions in adjacent structures unless signs of radiation injury were evident (e.g., scarring); and d) prior soft tissue radiation (e.g., supraclavicular radiation, radiation of internal mammary lymph nodes, etc.) precluded the selection of measurable disease in the site of radiation unless the lesions were new since radiation was completed.

All of the sites of disease present at baseline not classified as target lesions were classified as non-target lesions. Non-target lesions were qualitatively assessed at each subsequent time point. Examples of non-target lesions included: a) all bone lesions, irrespective of the modality used to assess them; b) leptomeningeal disease; c) lymphangitis of the skin or lung; d) cystic lesions; e) irradiated lesions that have not shown progression; f) measurable lesions beyond the maximum number of 10; g) groups of lesions that are small and numerous; and h) pleural effusion/pericardial effusion/ascites.

Unequivocal new lesions were those that were not present at baseline. At each time point, the presence of new lesions was determined. New multi-focal or miliary disease of any size were considered a new lesion. Lesions that were encountered (subsequent to the baseline) in anatomic locations that were not scanned at baseline were considered new lesions and represented progressive disease. Lesions that were present, which subsequently resolved and then recurred, were considered new lesions and represented progressive disease.

Response

Response was determined according to Response Evaluation Criteria in Solid Tumors (RECIST) guidelines. Therasse P. et al. *J Natl Cancer Inst.* 2000, 92:205-216. The study employed RECIST guidelines with adjustments based on current practices of the medical community. The charter of the blinded radiological review which was conducted by Icon Medical Imaging outlines the modifications to the original RECIST guidelines.

Antitumor response was defined as the percent of patients who achieved an objective confirmed response (complete or partial response). Disease control rate (stable disease (SM for at least 16 weeks or confirmed complete response (CR) or partial response (PR)) also was reported. The primary efficacy endpoint was the percentage of patients who achieve an objective confirmed complete or partial response based on a blinded radiological assessment of response. Superiority of Nab-paclitaxel/carboplatin to paclitaxel dissolved in polyoxyethylated castor oil and dehydrated alcohol, sold under the trademark TAXOL®/carboplatin was established when the lower bound of the 95.1% confidence interval (CI) of pA/pT >1.0. In addition to the ratio of response rates ((pA/pT) i.e. (complete response+partial response+stable disease)/(true toxicity rate)) and its 95.1% CI, the following were presented for each treatment regimen: sample size, overall rate response, and 95% CI of the response rate. Treatment regimen comparison of response rates were tested using the chi-square test.

Percentage change in SLD was evaluated by the following formulae: 1) when determining complete response or partial response: ((Post value−Baseline value)/Baseline value)×100 and 2) when determining progressive disease: (Post value−Nadir value since treatment started)/(Nadir value since treatment started)×100.

The following definitions were used to evaluate response based on target lesions at each time point after baseline: Complete Response (CR): Disappearance of all target lesions. Partial Response (PR): At least a 30% decrease in the SLD of target lesions, taking as reference the baseline SLD. Stable Disease (SD): Neither sufficient shrinkage of target lesions to qualify for PR, nor sufficient increase to qualify for PD, taking as reference the nadir SLD since the treatment started. Progressive Disease (PD): At least a 20% increase in the SLD of target lesions, taking as reference the nadir SLD recorded since the treatment started, or, the presence of one or more new lesions. Unable to Evaluate (UE): A target lesion present at baseline which was not measured or which was unable to be evaluated leading to an inability to determine the status of that particular tumor for the time point in question. If the SLD cannot be determined at a time point, and the rules for PD do not apply, a response of CR, PR or SD could not be assigned for that time point and the time point response was UE. Not Applicable (NA): No target lesions were identified at baseline. Patients with no target lesions identified at baseline could not be assessed for response. These patients were assessed for progression only. Not Done (ND): Scans were not performed at this time point to evaluate the target lesions.

Each non-target lesion was qualitatively evaluated at each time point. Response of each lesion at each time point was assessed with respect to the baseline status. Progression was assessed with respect to nadir size of the non-target lesions. The overall non-target lesion response for each time point was assessed as the worst case for the non-target lesions for that particular time point. If a non-target lesion was classified as UE/ND, the non-target response was UE/ND unless progression was identified in the available non-target lesions. Response assessments were defined as follows:

Complete Response (CR): Disappearance of all non-target lesions. Stable Disease (SD): The persistence of one or more non-target lesions not qualifying for CR or PD. Progressive Disease (PD): The "unequivocal progression" of existing non-target lesion(s) or appearance of one or more new lesion(s) was considered progressive disease. If PD for the subject was to be assessed for a time point based solely on the progression of non-target lesion(s), then additional criteria are required to be fulfilled. In this instance, the lesion(s) upon which the assessment of PD was being made must be retrospectively assessed from baseline (or the nadir) and compared to the time point in question. PD of non-target lesion(s) in this instance was assessed when the SLD of the lesion(s) had increased by 20% or greater and the lesion(s) measured greater than or equal to 10 mm in longest dimension (LD) at the time of progression. If the nontarget lesion(s) did not meet the quantitative criteria as described, they were not assessed as having progressed. For pleural fluid, ascites, pericardial effusions and other fluid collections, progression was assessed in an otherwise stable or responding subject when the increase in the fluid was estimated to be greater than 500 cc, and was not attributable to a benign cause identified radiographically. Unable to Evaluate (UE): Any non-target lesion present at baseline which was not measured or was unable to be evaluated leading to an inability to determine the status of that particular tumor for the time point in question. Not Applicable (NA): No non-target lesions were identified at baseline. Not Done (ND): Scans were not performed at this time point to evaluate the non-target lesions.

Disease control rate (SD for ≥16 weeks or confirmed CR or PR) was analyzed in the same manner as objective response.

Progression Free Survival

The final analysis for PFS was conducted once 70% of patients had an event of disease progression or death (for any cause). This was equivalent to 735 events which provides 85% power with a two-sided Type 1 error of 0.049 to detect a Nab-paclitaxel/carboplatin to paclitaxel dissolved in polyoxyethylated castor oil and dehydrated alcohol, sold under the trademark TAXOL®/carboplatin hazard ratio (HRA/T) of 0.80.

PFS was analyzed using Kaplan-Meier methods. PFS was defined as the time from the day of randomization to the start of disease progression or death (for any cause), whichever occurs first, based on the blinded radiological review assessment of response. PFS for patients who achieved an objective confirmed complete or partial response was presented as a measure of duration of response.

Patients who did not have disease progression or have not died were censored at the last known time that the patient was progression free. In the event that palliative radiotherapy or surgery at lesion sites occurs, the patient was censored at the last assessment without documented progression prior to the date of radiotherapy or surgery. In follow-up, patients who began new anti-cancer therapy (other than radiotherapy) prior to documented progression were censored at the last assessment where the patient was documented as progression free.

To assess the impact on PFS of response assessments not occurring at the regularly scheduled assessment times, the frequency of these unscheduled/off-scheduled assessments was presented for each treatment regimen. In addition, a confirmatory sensitivity analysis was performed where patients with events and censorings that occur at a time other than the regularly scheduled assessment, had PFS time based on the date of the next regularly scheduled assessment rather than the actual off-schedule date. To assess the impact of a single missed response assessment prior to a visit with documented disease progression, the frequency of missed response assessments was presented by treatment regimen. In addition, two confirmatory sensitivity analyses were conducted. In the first sensitivity analysis, these patients were censored at the last visit where the patient was documented to be progression free. In the second sensitivity analysis, these patients were considered to have progressed at the time of the missed response assessment.

The Nab-paclitaxel/carboplatin to paclitaxel dissolved in polyoxyethylated castor oil and dehydrated alcohol, sold under the trademark TAXOL®/carboplatin hazard ratio (HRA/T) and its 95.1% CI for PFS were evaluated. The following also were evaluated for each treatment regimen: sample size, number and percentage of patients with disease progression or death, median PFS, and a 95% CI for the median PFS. The Kaplan-Meier curve for PFS was evaluated for each treatment regimen and differences in the curves were tested using the log-rank test.

Patient Survival

The final analysis for patient survival was conducted once 70% of patients had died. This was equivalent to 735 deaths which provides 85% power with a two-sided Type 1 error of 0.049 to detect a Nab-paclitaxel/carboplatin to paclitaxel dissolved in polyoxyethylated castor oil and dehydrated alcohol, sold under the trademark TAXOL®/carboplatin hazard ratio (HRA/T) of 0.80. Patient survival was defined as the time from the day of randomization to patient death (for any cause). Patient survival was analyzed in a similar manner to PFS.

Safety/Tolerability Endpoints

The safety/tolerability endpoints were the incidence of treatment-emergent AEs and SAEs, laboratory abnormalities, and incidence of patients experiencing dose modifications, dose interruptions, and/or premature discontinuation of study drug.

AEs occurring during the study were graded according to the NCI Common Terminology Criteria for Adverse Events v3.0 (CTCAE) (see http://ctep.cancer.gov/reporting/ctc.html), where applicable. AEs that were not included on the toxicity scale were designated as Grade 1=mild, Grade 2=moderate, Grade 3=severe, Grade 4=life-threatening, and Grade 5=death. AEs that were determined not to be possibly, probably, or definitely related to study drug did not require further evaluation but were recorded. Study medications could be interrupted for an AE at the discretion of the investigator. Patients requiring toxicity management were assessed and evaluated at least weekly as indicated by the severity of the event.

According to the NCI CTCAE system of adverse event grading, laboratory values of Grade 3 or 4 were described as "severe" or "life-threatening." For example, a neutrophils count <500/mm3 would meet laboratory criteria as Grade 4 ("life-threatening"). This description was not always synonymous with the assessment of the "serious" criteria of an AE as "life threatening". Definition of AE and SAE are provided herein.

In order for AEs to be considered serious by "life-threatening" criteria, it was medically judged as possessing "an immediate risk of death from the event as it occurred," not because of the theoretical potential for life-threatening consequences. In the case of a neutrophil count <500/mm$^3$, the AE would be captured as an AE of Grade 4 neutropenia, but it was not automatically considered a SAE unless the investigational physician determined this represented an immediately life-threatening event for the patient. Specifically, uncomplicated Grade 4 neutropenia was not reported as a SAE. Neutropenia associated with fever, infection, or hospitalization was reported as a SAE.

Difference between Nab-paclitaxel/carboplatin and paclitaxel dissolved in polyoxyethylated castor oil and dehydrated alcohol, sold under the trademark TAXOL®/carboplatin were compared using the Cochran-Mantel-Haenszel test.

Patients in the treated population were followed for the development of AEs from study drug initiation through the end of study or 30 days after the end of treatment, whichever was longer. Only patients with clear documentation that no study drug was administered could be excluded from the treated population.

Peripheral neuropathy (PN) (sensory or motor) was reported by grade according to the NCI CTCAE. When the grade of the PN changes (i.e., increases or decreases), the stop date on the existing AE should be entered and a new AE started, reflecting the new grade.

Pharmacokinetic Endpoints

PK measurements of Nab-paclitaxel were taken around the 0.25, 3.5, and 24 hours post-infusion-end time points for patients randomized to receive Nab-paclitaxel/carboplatin in Russia, Ukraine, the United States, and Canada (approximately 100 patients). The pharmacokinetic parameters were the maximum plasma drug concentration ($C_{max}$), the area under the plasma concentration versus time curve (AUC and $AUC_{inf}$), the half-life of the apparent terminal portion of the concentration versus time curve ($T_{1/2}$), the total body clearance (CL), and the volume of distribution ($V_z$).

A sparse pharmacokinetic (PK) sampling method coupled with three-compartment model analysis was used to determine the PK parameters. The AUC is an important indicator of drug availability or the total amount of metabolite present.

To assess the relationship between drug exposure and safety, the correlation of nadir ANC with PK parameter estimates (e.g. absolute AUCinf) was evaluated using a linear regression analysis with an effect for PK parameter in the model. Transformation of nadir ANC data was considered if these data were non-normally distributed. To assess the relationship between drug exposure and efficacy, the correlation of objective confirmed response (based on blinded radiological review) with PK parameter estimates was evaluated using a logistic regression analysis with an effect for the PK parameter in the model. To assess the relationship between drug exposure and biomarkers, the correlation of each biomarker with PK parameter estimates was evaluated using a logistic regression analysis with an effect for the PK parameter in the model for biomarkers with binary outcomes and was evaluated using a linear regression analysis with an effect for PK parameter in the model for biomarkers with a continuous outcomes.

Laboratory Assessments

Hematology Parameters—

To investigate the maximal degree of myelosuppression, the CTCAE grade for WBC, ANC, platelet count, and hemoglobin concentration were summarized by the most severe grade for the first cycle of therapy and by the most severe grade anytime during therapy for each treatment regimen; testing of treatment regimen differences were performed using the CMH test. The incidence of patients with CTCAE hematology values of Grade 3 or 4 that occurred after the first dose of study drug was presented for each group. Data for patients with Grade 3 or 4 hematology values were listed.

Clinical Chemistry—

Liver and renal functions were summarized using the CTCAE for ALT, AST, total bilirubin, and creatinine. The number and percentage of patients who have each CTCAE grade were summarized by the most severe grade for the first cycle of therapy and by the most severe grade anytime during therapy for each treatment regimen; testing of treatment regimen differences was performed using the CMH test. The incidence of patients with CTCAE chemistry values of Grade 3 or 4 that occurred after the first dose of study drug was presented for each group. Data for patients with Grade 3 or 4 chemistry values were listed.

Evaluation of Molecular Biomarkers

Tumor biomarkers (mRNA and DNA) were studied to assess prognostic utility in identifying responders and non-responders in both treatment arms. Molecular biomarkers were assessed on archival paraffin-embedded (PE) tumor tissue of patients entered into the trial. Blood samples for the evaluation of molecular biomarkers were collected within two weeks prior to starting treatment, and then every other cycle (Day 1 of Cycles 3, 5, 7, etc.). If patients participated in both the pharmacokinetic sampling and the optional biomarker blood collection, the baseline blood draw for the biomarkers was performed at least 2 days prior to Day 1 in order to reduce the amount of blood drawn with each venipuncture. Approximately 25 mL of blood was collected at each sampling point for molecular biomarker evaluations.

These biomarkers included both RNA and DNA analysis performed using PCR based quantitative assays. For DNA biomarkers, loss of heterozygosity (LOH) of single-nucleotide polymorphism (SNP), Kras mutation, and methylation of promoter region of tumor-related genes were examined for both tumor tissue and blood. The expression of molecular biomarkers such as SPARC in PE tumor tissues were assessed for mRNA expression and specific epigenetic (promoter gene methylation) status to determine its potential clinicopathological utility related to treatment with Nab-paclitaxel. The objective was to assess specific tumor-related genes for up and down regulation and to identify specific gene expression patterns or specific biomarkers that relate to treatment response and disease outcome. In addition, PE tissue sections were obtained from tumor biopsy for immunohistochemistry (IHC) to assess SPARC and for molecular tumor biomarker validation. Tissues were collected from both randomized arms of the trial. Tumor tissue that was available from biopsy was used. Additional procedures will not be performed for the purpose of obtaining tumor tissue for molecular biomarker analyses.

In addition, blood biomarkers that have shown prognostic utility in monitoring patients during treatment [circulating tumor cells (CTC) and circulating DNA (cDNA)] were assayed. These assays may provide an alternative approach to better predict metastatic disease recurrence, disease response, and aid in the disease management of lung cancer patients. For the testing of these biomarkers, patients were requested to provide an additional volume of blood (approx. 25 mL) at baseline and on Day 1 of every other cycle thereafter, at the time of routine sampling for blood counts and chemistries (see schedule of events).

Tumor samples were collected from patients treated on this study to obtain preliminary data on a potential correlation between SPARC expression and response to combined therapy with Nab-paclitaxel/Carboplatin or paclitaxel dissolved in polyoxyethylated castor oil and dehydrated alcohol, sold under the trademark TAXOL®/Carboplatin. In those cases where tumor samples from patients treated on this study were available, tumor samples were submitted to a central laboratory for SPARC analysis. Samples were run blinded to the treatment assignment and to the response the patient had to treatment.

The correlation of SPARC and other molecular biomarkers with efficacy outcomes was analyzed. The following analyses were performed for each treatment regimen. Descriptive statistics were used to summarize biomarkers for responders versus non-responders. Continuous measures were summarized by sample size, mean, median, S.D., minimum, and maximum values. Categorical measures were summarized by number and percentage of patients in each category. To assess relationship between objective tumor response and biomarkers, a logistic regression analysis was performed with an effect for biomarker in the model. Relationship with disease control was analyzed in a similar manner. To assess the relationship of PFS with biomarkers, a Cox regression analysis was used with an effect for biomarker in the model. In addition, for SPARC and other biomarkers with binary measures, PFS was summarized by median PFS time (including 95% CI) for each biomarker category along with the hazard ratio (including 95% CI). The Kaplan-Meier curve for PFS was presented graphically for each biomarker category and differences in the curves were tested using the log-rank test.

Results

Baseline and histologic characteristics were well balanced in the two arms. Dose intensity of paclitaxel was higher in the Nab-paclitaxel/Carboplatin v. paclitaxel dissolved in polyoxyethylated castor oil and dehydrated alcohol, sold under the trademark TAXOL®/Carboplatin arm (82 vs. 65 mg/m$^2$/wk). Nab-paclitaxel/Carboplatin overall response rate (ORR) was superior to paclitaxel dissolved in polyoxyethylated castor oil and dehydrated alcohol, sold under the trademark TAXOL®/Carboplatin both by independent radiologic review (IRR) (33% vs. 25%, P=0.005), a 31% improvement, and by investigator review (37% vs. 30%, P=0.008), a 26% improvement. Analysis by histology revealed significantly improved ORR for Nab-paclitaxel/Carboplatin vs. paclitaxel dissolved in polyoxyethylated castor oil and dehydrated alcohol, sold under the trademark TAXOL®/Carboplatin in squamous cell carcinoma patients (41% vs. 24%, P<0.001, IRR), a 67% improvement, and Nab-paclitaxel/Carboplatin was as effective as paclitaxel dissolved in polyoxyethylated castor oil and dehydrated alcohol, sold under the trademark TAXOL®/Carboplatin in nonsquamous cell carcinoma patients (ORR 26% vs. 25%). Nab-paclitaxel/Carboplatin was well tolerated, with significantly improved safety profile vs. paclitaxel dissolved in polyoxyethylated castor oil and dehydrated alcohol, sold under the trademark TAXOL®/Carboplatin despite the higher cumulative paclitaxel dose delivered (1442 mg/m$^2$ vs. 1131 mg/m$^2$) without premedication:

| Statistically significant events | Nab-paclitaxel/ Carboplatin n = 514 | Taxol/ Carboplatin n = 524 | P-value |
|---|---|---|---|
| G ≥3 Nonhematologic, n (%) | | | |
| Neuropathy | 15 (3) | 56 (11) | <0.001 |
| Myalgia | 1 (<1) | 10 (2) | 0.011 |
| Arthralgia | 0 | 8 (2) | 0.008 |
| G 4 Hematologic, n (%) | | | |
| Neutropenia | 49 (11) | 98 (22) | <0.001 |
| Thrombocytopenia | 23 (5) | 5 (1) | 0.001 |
| Anemia | 21 (5) | 4 (1) | 0.001 |

Nab-paclitaxel/Carboplatin significantly improved ORR and safety profile vs. paclitaxel dissolved in polyoxyethylated castor oil and dehydrated alcohol, sold under the trademark TAXOL®/Carboplatin as first-line therapy for advanced NSCLC. Nab-paclitaxel/Carboplatin was especially active in the difficult to treat squamous cell carcinoma subset, which may in part be attributed to increased intratumoral Nab-paclitaxel/Carboplatin delivered via the gp60-CAV1 pathway in squamous carcinoma cells (Yoo et al. Lung Cancer. 2003 42:195-202) with aberrant CAV1 overexpression.

Example 2: Treatment of Lung Cancer

This example provides results from a phase 3 trial which studied the efficacy of Nab-paclitaxel or nab-P i.e., the albumin stabilized nanoparticle formulation of paclitaxel sold under the trademark ABRAXANE® vs. paclitaxel dissolved in polyoxyethylated castor oil and dehydrated alcohol, sold under the trademark TAXOL® (P) in combination with carboplatin (nab-PC v. PC) in advanced non-small cell lung cancer (NSCLC) of all histologic types.

Methods: First-line Stage IIIB or IV NSCLC pts (ECOG 0/1) were randomized to C AUC6 q3w and either nab-P 100 mg/m$^2$ weekly without premedication (n=521) or P 200 mg/m$^2$ once every three weeks with premedication (n=531). Primary endpoint: ORR by independent radiologic review (IRR).

Results: Baseline and histologic characteristics were well balanced. Dose intensity of paclitaxel was higher in nab-PC vs. PC (82 vs. 65 mg/m$^2$/wk). nab-PC was superior to PC both by IRR (33% vs. 25%, P=0.005), a 31% improvement (1.313 response ratio (RR), 95% CI: 1.082, 1.593), and by investigator review (37% vs. 30%, P=0.008), a 26% improvement (1.259 RR, CI: 1.060, 1.496). Histologic analysis showed significantly improved ORR for nab-PC vs. PC in squamous cell carcinoma (SQC) pts (41% vs. 24%, P<0.001, IRR), a 67% improvement (1.669 RR, CI: 1.262, 2.208). nab-PC was as effective as PC in non-SQC pts (ORR 26% vs. 25%). nab-PC was well tolerated, with significantly improved safety profile vs. PC despite higher paclitaxel dose delivered (1338 vs. 1100 mg/m$^2$).

| Statistically significant events | nab-PC n = 514 | PC n = 524 | P-value |
|---|---|---|---|
| G ≥3 Nonhematologic, n (%) | | | |
| Neuropathy | 15 (3) | 56 (11) | <0.001 |
| Myalgia | 1 (<1) | 10 (2) | 0.011 |
| Arthralgia | 0 | 8 (2) | 0.008 |
| G 4 Hematologic, n (%) | | | |
| Neutropenia | 49 (11) | 98 (22) | <0.001 |
| Thrombocytopenia | 23 (5) | 5 (1) | 0.001 |
| Anemia | 21 (5) | 4 (1) | 0.001 |

Conclusions: nab-PC significantly improved ORR and safety profile vs. PC as first-line therapy for advanced NSCLC. nab-PC was especially active in the SQC subset, which may in part be attributed to the aberrant CAV1 overexpression in squamous carcinoma cells (Yoo 2003) and the high intratumoral accumulation of nab-P via the gp60-CAV1 pathway.

Example 3: Nab-Paclitaxel in Combination with Carboplatin as First-Line Therapy in Diabetic Patients with Advanced Non-Small Cell Lung Cancer (NSCLC)

Diabetes and other age-related comorbidities frequently occur together in patients with NSCLC and may affect treatment tolerability. In a phase III trial, nab paclitaxel (nab-P, 130 nm albumin-bound paclitaxel particles)+carboplatin (C) significantly improved the primary endpoint of overall response rate (ORR) from 25% to 33% (P=0.005) with a trend toward improved overall survival (OS) and progression-free survival (PFS) vs. solvent-based paclitaxel (sb-P)+carboplatin in patients with advanced NSCLC. This exploratory analysis examined efficacy and safety outcomes in diabetic patients.

Patients with untreated stage 111B/IV NSCLC were randomized 1:1 to carboplatin AUC 6 on day 1 and either nab paclitaxel 100 mg/m$^2$ on days 1, 8, 15 or solvent-based paclitaxel 200 mg/m$^2$ day 1 every 21 days. Overall response rate and progression-free survival were determined by blinded centralized review. P values for overall response rate based on chi-square and those for overall survival and progression-free survival were based on log-rank. Multiple sensitivity analyses were performed to confirm treatment differences.

31 patients in the nab-paclitaxel/carboplatin and 30 patients in the solvent-based paclitaxel/carboplatin arms were included in this analysis. Similar to the intent-to-treat (ITT) population, most diabetic patients were male (75%), white (62%), with ECOG performance status of 1 (79%), and stage IV disease (85%). In these patients, overall response rate for nab-paclitaxel/carboplatin vs. solvent-based paclitaxel/carboplatin was 52% vs. 27% (response rate ratio 1.935, P=0.046), median progression-free survival was 10.9 vs. 4.9 months (HR 0.416, P=0.016), and median overall survival was 17.5 vs. 11.1 months (HR 0.553, P=0.057). The percentage of patients experiencing ≥1 adverse effect was similar between the diabetic and intent-to-treat populations. Metformin was concomitantly used in 26% and 30% of diabetic patients in the nab-paclitaxel/carboplatin vs. solvent-based paclitaxel/carboplatin arms, respectively. Among diabetic patients, the most common grade 3/4 adverse effects in the nab-paclitaxel/carboplatin vs. solvent-based paclitaxel/carboplatin arms were neutropenia (53% vs. 55%), anemia (23% vs. 10%), peripheral neuropathy (7% vs. 23%), thrombocytopenia (20% vs. 7%), and fatigue (7% vs. 10%); differences were not significant.

In this analysis, nab-Paclitaxel (nab-PIC) demonstrated promising activity and was well tolerated in diabetic patients with advanced NSCLC. These findings warrant further study in a larger patient population with diabetes.

Example 4: Nab-Paclitaxel in Combination with Carboplatin as First-Line Therapy in Patients with Advanced Non-Small Cell Lung Cancer (NSCLC): Analysis of Prognostic Factors Identification of prognostic is critical for appropriate selection of patients and chemotherapy regimen. In a phase 3 trial, nab-paclitaxel (nab-P, 130 nm albumin-bound paclitaxel particles)+carboplatin (C) vs. solvent-based paclitaxel (sb-P)+carboplatin significantly improved overall response rate (primary endpoint 33% vs. 25%, P=0.005), with a trend toward improved overall survival and progression free survival in patients with advanced NSCLC. This exploratory analysis examined prognostic factors and clinical outcomes with nab-paclitaxel/carboplatin.

Patients with untreated stage IIIB/IV NSCLC and an ECOG performance status of 0/1 were randomized 1:1 to carboplatin AUC 6 day 1 and either nab-paclitaxel 100 mg/m$^2$ on days 1, 8, 15 (n=51) or solvent-based paclitaxel 200 mg/m$^2$ day 1 (n=531) every 21 days. Overall response rate and progression free survival were assessed by blinded centralized review. P values for overall response rate based on chi-square and those for overall survival and progression free survival based on log-rank test.

The hazard ratio/risk ratio favored nab-paclitaxel/carboplatin for overall response rate, progression free survival, and overall survival for most factors analyzed. Significant quantitative treatment-by-prognostic factors interactions were noted for a few key factors with respect to outcomes. Comparative treatment effect was maintained in patients without those factors. In patients with ≥4 metastatic sites, significant treatment differences favoring nab-paclitaxel/carboplatin were noted for overall response rate (response rate ratio [RRR] 3.40; P=0.003) and overall survival (hazard ratio [HR] 0.562; P=0.009), and trended in favor of nab-paclitaxel/carboplatin for progression free survival (HR 0.735; P=NS). In patients with diabetes, significant treatment differences favoring nab-paclitaxel/carboplatin were noted for progression free survival (HR 0.416; P=0.016) and overall response rate (RRR 1.94; P=0.046), and trended in favor of nab-paclitaxel/carboplatin for overall survival (HR 0.553; P=0.057). In patients with squamous NSCLC, significant treatment differences favoring nab-paclitaxel/carboplatin were noted for overall response rate (RRR 1.68; P<0.001) and trended in favor of nab-paclitaxel/carboplatin for overall survival (HR 0.890; P=NS). In patients ≥70 years, significant treatment differences favoring nab-paclitaxel/carboplatin were noted for overall survival (HR 0.583; P=0.009) and overall response rate (RRR 1.39; P=0.013) and trended in favor of nab-paclitaxel/carboplatin for progression free survival (HR 0.687; P=NS). No significant treatment differences significantly favoring solvent-based paclitaxel/carboplatin were observed.

A trend toward improved outcomes was noted with nab-paclitaxel/carboplatin vs. solvent-based paclitaxel/carboplatin in most prognostic factors analyzed. Squamous NSCLC, diabetes, age ≥70 years, and ≥4 metastatic sites were prognostic of improved outcomes with nab-paclitaxel/carboplatin vs. solvent-based paclitaxel/carboplatin.

Example 5: Safety and Efficacy of Weekly Nab-Paclitaxel in Combination with Carboplatin as First-Line Therapy in Elderly Patients with Advanced Non-Small Cell Lung Cancer (NSCLC)

The safety and efficacy of carboplatin with either nab-paclitaxel 100 mg/m$^2$ weekly (nab-PIC) or solvent-based paclitaxel 200 mg/m$^2$ every 3 weeks (sb-P/C) was evaluated in elderly (≥70 years old) vs. younger patients with advanced non-small cell lung cancer (NSCLC) enrolled in the phase III CA031 trial.

Fifteen percent of intent-to-treat (ITT) patients (156/1,052) were elderly (nab-paclitaxel/carboplatin, n=73; solvent-based paclitaxel/carboplatin, n=81; 2 were not treated). The majority of elderly patients was male (72%), Caucasian (71%), with baseline Eastern Cooperative Oncology Group (ECOG) performance status of 1 (73%) and stage IV disease (83%). The median number of cycles administered was 5.0 with nab-paclitaxel/carboplatin vs. 6.0 with solvent-based paclitaxel/carboplatin. Baseline characteristics were generally well balanced between the treatment arms in the elderly population; however, the nab-paclitaxel/carboplatin arm had more patients with squamous histology (47% vs. 37%) and more previous smokers (47% vs. 39%).

In elderly patients, independent radiologic assessment revealed a higher overall response rate (confirmed complete or partial responses) with nab-paclitaxel/carboplatin vs. solvent-based paclitaxel/carboplatin (34% vs. 24%; response rate ratio [RRR]=1.385; P=0.196). In patients <70 years old, a significant improvement in ORR was observed with nab-paclitaxel/carboplatin vs. solvent-based paclitaxel/carboplatin (32% vs. 25%; RRR=1.300; P=0.013). No significant interaction (P=0.0814) between age and the treatment effect on overall response rate was noted.

In elderly patients, a nonsignificant trend toward improved progression free survival (8.0 months with nab-paclitaxel/carboplatin vs. 6.8 months with solvent-based paclitaxel/carboplatin; hazard ratio [HR] 0.687; P=0.134) and a significant improvement in median overall survival (19.9 months with nab-paclitaxel/carboplatin vs. 10.4 months with solvent-based paclitaxel/carboplatin; HR 0.583; P=0.009) were observed with nab-paclitaxel/carboplatin vs. solvent-based paclitaxel/carboplatin. No differences were observed in progression free survival or overall survival in patients <70 years old. A significant (P=0.018) interaction between age and the treatment effect on overall survival was observed.

TABLE 4

Outcomes of Select Populations From the CA031 Trial

| Treatment | ITT | | Nonelderly <70 Years | | Elderly ≥70 Years | |
|---|---|---|---|---|---|---|
| | nab-P/C | sb-P/C | nab-P/C | sb-P/C | nab-P/C | sb-P/C |
| n | 514 | 524 | 447 | 449 | 74 | 82 |
| ORR, % | 33 | 25 | 32 | 25 | 34 | 24 |
| Response rate ratio | 1.313 | | 1.300 | | 1.385 | |
| 95% CI | 1.082-1.593 | | 1.055-1.603 | | 0.843-2.227 | |
| P value | 0.005 | | 0.013 | | 0.196 | |
| Median PFS in months | 6.3 | 5.8 | 6.0 | 5.8 | 8.0 | 6.8 |
| HR | 0.902 | | 0.903 | | 0.687 | |
| 95% CI | 0.767-1.060 | | 0.759-1.074 | | 0.420-1.123 | |
| P value | 0.214 | | 0.256 | | 0.134 | |
| Median OS in months | 12.1 | 11.2 | 11.4 | 11.3 | 19.9 | 10.4 |
| HR | 0.922 | | 0.999 | | 0.583 | |
| 95% CI | 0.797-1.066 | | 0.855-1.167 | | 0.388-0.875 | |
| P value | 0.271 | | 0.988 | | 0.009 | |

Abbreviations in Table 4: CI, confidence interval; HR, hazard ratio; ITT, intent-to-treat; nab-P/C, nab-paclitaxel + carboplatin; ORR, overall response rate; OS, overall survival; PFS, progression-free survival; sb-P/C, solvent-based paclitaxel + carboplatin; P values for ITT based on chi-square test; all other P values based on chi-square test for ORR, stratified log-rank for OS and PFS.

Despite a higher weekly dose intensity with nab-paclitaxel/carboplatin vs. solvent-based paclitaxel/carboplatin, elderly patients receiving nab-paclitaxel/carboplatin experienced significantly less all-grade sensory neuropathy (P=0.001), neutropenia (P=0.015), and arthralgia (P=0.029) vs. those receiving solvent-based paclitaxel/carboplatin but more anemia (P=0.007). A similar trend was observed in patients <70 years old. Fewer elderly patients in the nab-paclitaxel/carboplatin arm vs. solvent-based paclitaxel/carboplatin arm experienced grade 3/4 neutropenia (55% vs. 73%, respectively; P=0.018). Rates of grade 3/4 neutropenia remained high from cycle 2 through cycle 6 in elderly patients who received solvent-based paclitaxel/carboplatin, whereas rates peaked in cycle 3 and then progressively declined in patients receiving nab-paclitaxel/carboplatin. In elderly patients, rates of grade 3/4 neuropathy were significantly lower (P=0.007), and neuropathy occurred later during treatment (48 vs. 24.5 days, P=0.002) with nab-paclitaxel/carboplatin vs. solvent-based paclitaxel/carboplatin. In the nab-paclitaxel/carboplatin vs. solvent-based paclitaxel/carboplatin arms, respectively, 55% vs. 37% had a taxane dose reduction, primarily due to neutropenia, thrombocytopenia, anemia, or sensory neuropathy. At the time of the data cutoff for the final analyses, all elderly patients except one in the nab-paclitaxel/carboplatin arm had discontinued therapy; the most common reason for discontinuation was progressive disease. Compliance with the Functional Assessment of Cancer Therapy (FACT)-Taxane questionnaire was high (99%), and most patients provided follow-up assessments (90%). Significant treatment effects favoring the nab paclitaxel/carboplatin arm were noted in patient-reported neuropathy (P<0.001), pain in hands/feet (P<0.001), hearing loss (P=0.022), and edema (P=0.004).

TABLE 5

Adverse Events Grade ≥3 in ITT and Select Populations from the CA031 Trial

| | ITT | | Nonelderly <70 Years | | Elderly ≥Years | |
|---|---|---|---|---|---|---|
| | nab-P/C | sb-P/C | nab-P/C | sb-P/C | nab-P/C | sb-P/C |
| n | 514 | 524 | 441 | 443 | 73 | 81 |
| Anemia, % | 27 | 7[a] | 28 | 6[a] | 23 | 10[a] |
| Neutropenia, % | 47[b] | 58 | 45 | 55 | 54[b] | 74 |
| Thrombocytopenia, % | 18 | 9[a] | 18 | 8[a] | 23 | 14 |
| Sensory neuropathy, % | 3[b] | 12 | 2[b] | 9 | 7[b] | 23 |
| Anorexia, % | 2 | <1 | 2 | <1 | 1 | 0 |

Abbreviations in Table 5: CI, confidence interval; HR, hazard ratio; ITT, intent-to-treat; nab-P/C, nab-paclitaxel + carboplatin; ORR, overall response rate; OS, overall survival; PFS, progression-free survival; sb-P/C, solvent-based paclitaxel + carboplatin.
[a]P < 0.05 in favor of sb-P/C for all grades.
[b]P < 0.05 in favor of nab-P/C for all grades.
P values base on Cochran-Mantel-Haenszel test for all grades In elderly patients with advanced NSCLC of all histologies, first-line nab paclitaxel/carboplatin therapy yielded a trend toward increased overall response rate and progression free survival and significantly improved overall survival compared with solvent-based paclitaxel/carboplatin, with an improved tolerability profile.

Lung cancer is primarily a disease of the elderly, and the median age at diagnosis is 71 years (Howlader N, Noone A, Krapcho M, et al (eds). SEER Cancer Statistics Review, 1975-2008. National Cancer Institute; Bethesda, Md. Disclosed at world wide web at seer.cancer.gov/csr/1975_2008/results_single/sect_01_table.11_2 pgs.pdf. Accessed 8 Aug. 2012). Elderly patients are often underrepresented in clinical trials, and treatment is challenging because of the number of preexisting comorbidities, increased incidence of polypharmacy, and increased risk of toxicity from chemotherapy (Quiox E. (2011) "Optimal pharmacotherapeutic strategies for elderly patients with advanced non-small cell lung cancer." Drugs Aging. 28: 885-894; Gridelli C. (2002) "Does chemotherapy have a role as palliative therapy for unfit or elderly patients with non-small cell lung cancer?" Lung Cancer. 28:S45-S50). The results of this analysis support the efficacy and safety findings from the full, randomized, international, phase III CA031 trial comparing nab-paclitaxel/carboplatin vs. solvent-based paclitaxel/carboplatin in patients with advanced NSCLC (Socinski M A, Bondarenko I, Karaseva N A, et al. (2012) "Weekly nab-paclitaxel in combination with carboplatin versus solvent-based paclitaxel plus carboplatin as first-line therapy in patients with advanced non-small-cell lung cancer: final results of a phase III trial." J Clin Oncol. 30:2055-2062) and suggest that nab-paclitaxel/carboplatin should be considered among first-line treatment options for elderly patients with advanced NSCLC.

Among elderly patients in this analysis, first-line therapy with nab-paclitaxel/carboplatin vs. solvent-based paclitaxel/carboplatin was associated with improved tolerability as well as better disease and symptom control. These factors may have allowed patients to stay on treatment longer and subsequently receive second-line treatment, which may have contributed to the improvement in overall survival compared with solvent-based paclitaxel/carboplatin therapy. The adverse event profile in elderly patients mirrors that described for the study's intent-to-treat population (Socinski M A, Bondarenko I, Karaseva N A, et al. (2012) "Weekly nab-paclitaxel in combination with carboplatin versus solvent-based paclitaxel plus carboplatin as first-line therapy in patients with advanced non-small-cell lung cancer: final results of a phase III trial." *J Clin Oncol.* 30:2055-2062) and for patients <70 years old. This is particularly promising in terms of the rate of neuropathy in the elderly population because neuropathy has historically been dose limiting in taxane-based regimens (Mielke S, Sparreboom A, Mross K. (2006) "Peripheral neuropathy: a persisting challenge in paclitaxel-based regimes." *Eur J Cancer.* 42:24-30). In elderly patients receiving nab-paclitaxel/carboplatin, grade ≥3 neutropenia decreased after cycle 3, which may have allowed for higher dose delivery and intensity and may have contributed to the apparent survival advantage.

Although the sample size of the subset of elderly patients is relatively small (15% of the overall trial population), the combination of nab-paclitaxel/carboplatin looks particularly promising when compared in context with historical data for platinum-based doublets in elderly patients with NSCLC (Quoix E, Zalcman G, Oster J P, et al. (2011) "Carboplatin and weekly paclitaxel doublet chemotherapy compared with monotherapy in elderly patients with advanced non-small-cell lung cancer: IFCT-0501 randomized, phase 3 trial." *Lancet.* 378:1079-1088; Kudoh S, Takeda K, Nakagawa K, et al. (2006) "Phase III study of docetaxel compared with vinorelbine in elderly patients with advanced non-small-cell lung cancer: results of the West Japan Thoracic Oncology Group Trial (WJTOG 9904). *J Clin Oncol.* 24:3657-3663; Belani C P, Fossella F. (2005) "Elderly subgroup analysis of a randomized phase III study of docetaxel plus platinum combinations versus vinorelbine plus cisplatin for first-line treatment of advanced non-small cell lung carcinoma (TAX 326)." *Cancer.* 104:2766-2774; Lilenbaum R C, Herndon J E 2nd, List M A, et al. (2005) Single-agent versus combination chemotherapy in advanced non-small-cell lung cancer: the Cancer and Leukemia Group B (study 9730)." *J Clin Oncol.* 23: 190-196) and warrants further evaluation in larger studies. A phase III trial (IFCT-0501) of solvent-based paclitaxel/carboplatin vs. vinorelbine or gemcitabine monotherapy in elderly patients (70-89 years with ECOG performance status 0-2) demonstrated improved survival with platinum-based doublet chemotherapy (median overall survival: 10.3 vs. 6.2 months; HR 0.64; P<0.0001); however, toxic effects were also more frequently observed with doublet chemotherapy (grade 3/4 neutropenia, 48.4% vs. 12.4%) (Quoix E, Zalcman G, Oster J P, et al. (2011) "Carboplatin and weekly paclitaxel doublet chemotherapy compared with monotherapy in elderly patients with advanced non-small-cell lung cancer: IFCT-0501 randomized, phase 3 trial." *Lancet.* 378:1079-1088).

Although cross-study comparisons must be made with caution, the median overall survival among elderly patients receiving solvent-based paclitaxel/carboplatin in CA031 was similar to that in IFCT-0501 (10.4 months) and significantly greater among those receiving nab-paclitaxel/carboplatin (19.9 months; P=0.009); this supports the use of doublet chemotherapy in elderly patients with NSCLC. Single-agent therapies or platinum-based doublets are recommended as first-line therapy in elderly patients with advanced NSCLC (National Comprehensive Cancer Network. NCCN Clinical Practice Guidelines in Oncology: Non-Small Cell Lung Cancer. V 3.2012), and taxane-based doublets have demonstrated encouraging efficacy and tolerable safety profiles in this population.

Possible limitations of this study include: post-hoc analysis with a small sample size, more patients with squamous histology and more previous smokers in the nab-paclitaxel/carboplatin arm compared with the solvent-based paclitaxel/carboplatin arm, which could have led to better prognosis for nab-paclitaxel/carboplatin-treated patients. Trial selected for fit patients (ECOG performance status of 0 or 1), while patients in the clinic are frequently less fit (ECOG performance status of 2) and therefore, may experience less efficacy and/or decreased tolerability in a real-world setting.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of treating non-small cell lung cancer (NSCLC) in an individual in need thereof, comprising administering a) an effective amount of a composition comprising nanoparticles comprising paclitaxel and an albumin and b) an effective amount of a platinum-based agent to the individual, wherein the individual was diagnosed with diabetes prior to the administration step, wherein the individual is selected for treatment based on having diabetes, and wherein the individual does not have pre-existing peripheral neuropathy of Grade 2, 3, or 4.

2. The method of claim 1, wherein the treatment is further based on the individual being at least about 70 years old.

3. The method of claim 1, wherein the dose of paclitaxel in the composition comprising nanoparticles comprising paclitaxel and albumin is between about 50 mg/m$^2$ and about 125 mg/m$^2$.

4. The method of claim 1, wherein the composition comprising nanoparticles comprising paclitaxel and albumin is administered weekly.

5. The method of claim 1, wherein the platinum-based agent is administered once every three weeks.

6. The method of claim 1, wherein paclitaxel in the nanoparticles is coated with albumin.

7. The method of claim 1, wherein the nanoparticles in the composition have an average diameter of no greater than about 200 nm.

8. The method of claim 1, wherein the NSCLC is Stage IIIB NSCLC or Stage IV NSCLC.

9. The method of claim 1, wherein the composition comprising nanoparticles comprising paclitaxel and albumin and the platinum-based agent are administered parenterally.

10. The method of claim 1, wherein the composition comprising nanoparticles comprising paclitaxel and albumin and the platinum-based agent are administered intravenously.

11. The method of claim 1, wherein the platinum-based agent is carboplatin.

12. The method of claim 1, wherein the individual is human.

* * * * *